(12) United States Patent
Hamamoto et al.

(10) Patent No.: US 8,338,607 B2
(45) Date of Patent: Dec. 25, 2012

(54) CYCLIC AMINE COMPOUNDS AND AGENTS FOR PEST CONTROL

(75) Inventors: Isami Hamamoto, Odawara (JP); Jun Takahashi, Odawara (JP); Makio Yano, Odawara (JP); Masahiro Kawaguchi, Odawara (JP); Daisuke Hanai, Aizuwakamatsu (JP); Takao Iwasa, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 845 days.

(21) Appl. No.: 12/083,127

(22) PCT Filed: Oct. 6, 2006

(86) PCT No.: PCT/JP2006/320126
§ 371 (c)(1),
(2), (4) Date: Jun. 13, 2008

(87) PCT Pub. No.: WO2007/040280
PCT Pub. Date: Apr. 12, 2007

(65) Prior Publication Data
US 2009/0259046 A1  Oct. 15, 2009

(30) Foreign Application Priority Data

| Oct. 6, 2005 | (JP) | 2005-294126 |
|---|---|---|
| Oct. 6, 2005 | (JP) | 2005-294127 |
| Oct. 12, 2005 | (JP) | 2005-297803 |
| Oct. 12, 2005 | (JP) | 2005-297804 |
| Jan. 25, 2006 | (JP) | 2006-016877 |
| Jun. 30, 2006 | (JP) | 2006-182314 |

(51) Int. Cl.
C07D 401/00 (2006.01)
C07D 401/14 (2006.01)
C07D 401/02 (2006.01)
A01P 7/04 (2006.01)

(52) U.S. Cl. .......... 546/255; 546/256; 544/238

(58) Field of Classification Search .......... None
See application file for complete search history.

(56) References Cited

U.S. PATENT DOCUMENTS

| 4,451,473 A | 5/1984 | Nador et al. | |
|---|---|---|---|
| 4,968,704 A * | 11/1990 | Cross et al. | 514/318 |
| 4,985,063 A | 1/1991 | Fischer et al. | |
| 5,001,125 A * | 3/1991 | Stokbroekx et al. | 514/252.02 |
| 5,057,528 A * | 10/1991 | Cross et al. | 514/352 |
| 5,364,865 A | 11/1994 | Diana | |
| 5,500,423 A * | 3/1996 | Glamkowski et al. | 514/228.2 |
| 5,571,815 A | 11/1996 | Schaper et al. | |
| 5,723,450 A | 3/1998 | Reuschling et al. | |
| 5,801,173 A | 9/1998 | Lohray et al. | |
| 5,859,024 A | 1/1999 | Hotson et al. | |
| 5,912,254 A | 6/1999 | Bishop et al. | |
| 5,919,782 A | 7/1999 | Lobray et al. | |
| 5,922,732 A | 7/1999 | Urch et al. | |
| 5,935,953 A | 8/1999 | Kuhar et al. | |
| 5,968,947 A | 10/1999 | Urch et al. | |
| 6,174,894 B1 | 1/2001 | Urch et al. | |
| 6,177,442 B1 | 1/2001 | Urch et al. | |
| 6,750,228 B1 * | 6/2004 | Barta et al. | 514/316 |
| 7,199,147 B2 | 4/2007 | Imazaki et al. | |
| 2004/0138286 A1 | 7/2004 | Imakazi et al. | |
| 2004/0147555 A1 | 7/2004 | Fujimoto et al. | |
| 2008/0045569 A1 | 2/2008 | Hamamoto et al. | |
| 2008/0319003 A1 | 12/2008 | Hamamoto et al. | |
| 2009/0099200 A1 * | 4/2009 | Li et al. | 514/254.02 |
| 2009/0118296 A1 * | 5/2009 | Black et al. | 514/252.02 |
| 2009/0143443 A1 | 6/2009 | Hamamoto et al. | |

FOREIGN PATENT DOCUMENTS

| EP | 0605031 | 7/1994 |
|---|---|---|
| EP | 1457490 | 9/2004 |
| JP | 58-49383 | 3/1983 |
| JP | 02-111773 | 4/1990 |
| JP | 6-211839 | 8/1994 |
| JP | 7-506347 | 7/1995 |
| JP | 9-502446 | 3/1997 |
| JP | 2001-081071 | 3/2001 |
| JP | 2001-504476 | 4/2001 |
| JP | 2001-506989 | 5/2001 |
| JP | 2003-40773 | 2/2003 |
| JP | 2003-137865 | 5/2003 |
| JP | 2006/320126 | 10/2006 |
| TW | 200642591 | 12/2006 |
| WO | WO 97/28128 | 8/1997 |

(Continued)

OTHER PUBLICATIONS

Korean Notice of Allowance, issued Dec. 1, 2010 during the prosecution of Korean Application No. 2008-7007883.

(Continued)

*Primary Examiner* — Janet Andres
*Assistant Examiner* — Timothy R Rozof
(74) *Attorney, Agent, or Firm* — Kenyon & Kenyon LLP

(57) ABSTRACT

Agents for pest control comprising cyclic amine compounds represented by the formula (1)

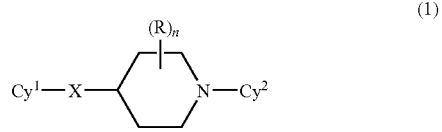

or salts thereof or N-oxides thereof as an active ingredient, wherein $Cy^1$ represents an unsubstituted or substituted 5-membered heterocycle or unsubstituted or substituted group represented by the formula (a) below,

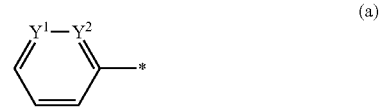

wherein $Y^1$ and $Y^2$ each independently represents nitrogen or carbon and symbol * represents the bonding positions.

4 Claims, No Drawings

FOREIGN PATENT DOCUMENTS

| | | |
|---|---|---|
| WO | WO 97/41120 | 11/1997 |
| WO | 98/22462 | 5/1998 |
| WO | 01/38325 | 5/2001 |
| WO | WO 02/81448 | 10/2002 |
| WO | WO 02/89803 | 11/2002 |
| WO | WO 02/089803 | 11/2002 |
| WO | 02/100833 | 12/2002 |
| WO | 03/097604 | 11/2003 |
| WO | WO 2004033463 A1 * | 4/2004 |
| WO | WO 2004/099160 | 11/2004 |
| WO | 2005/014578 | 2/2005 |
| WO | WO 2005/036961 | 4/2005 |
| WO | 2005/095380 | 10/2005 |
| WO | WO 2006/075004 A2 | 7/2006 |

OTHER PUBLICATIONS

European Search Report, European Patent Application No. EP 06 81 1460, dated Jul. 22, 2010.

Taiwanese Preliminary Examination Report, Taiwanese Patent Application No. 095137297, dated Aug. 25, 2009 (English-language translation provided).

Indian Examination Report, issued Jan. 14, 2011 during prosecution of Indian Application No. 1308/KOLNP/2008.

Office Action issued Oct. 22, 2010 for U.S. Appl. No. 12/083,137, filed Jan. 21, 2011.

Japanese Patent Office, International Search Report (translated) and Written Opinion dated Nov. 7, 2006, from related International Patent Application No. PCT/JP2006/320126, filed on Oct. 6, 2006 (in Japanese).

Patent Abstracts of Japan for JP 2001-081070 published Mar. 27, 2001.

Cooper, R. D. G., et al., "A Chiral Synthesis of D-Homoserine and it's Application of the Synthesis of Nocardicin A," *Tetrahedron Letters*, 1978, No. 26., p. 2243-2246.

Albert, Jeffrey S., et al., "Design, Synthesis, and SAR of Tachykinin Antagonists: Modulation of Balance in NK1/NK2 Receptor Antagonist Activity," *Journal of Medicinal Chemistry*, 2002, vol. 45, No. 18, p. 3972-3983.

Eichler, Eva, et al., "1,8-Naphthyridines. Part 1. Synthesis of Some Trifluoromethyl-1,8-naphthyridine Derivatives," *Journal of Heterocyclic Chemistry*, vol. 13, No. 1, Feb. 1976, p. 41-42.

Lowe, John A., et al., "Aza-Tricyclic Substance P Antagonists," *Journal of Medical Chemistry*, vol. 37, No. 18, Sep. 2, 1994, p. 2831-2840.

Ek, Fredrik, et al., "Aromatic Allylation via Diazotization: Metal-Free C-C Bond Formation," *Journal of Organic Chemistry*, vol. 67, 2002, p. 6376-6381.

Kim, Deog-II, et al., "Synthesis and Pharmacology of Site Specific Cocaine Abuse Treatment Agents: 8-Substituted Isotrope (3-Azabicycic[3.2.1]octane) Dopamine Uptake," *Journal of Medicinal Chemistry*, vol. 46, No. 8, Apr. 10, 2003, p. 1456-1464.

Ferguson, John R., et al., "Efficient New Syntheses of (+)- And (−)-Anatoxin-a, Revised Configuration of Resolved 9-Methyl-9azabicyclo[4.2.1]nonan-2-one," *Tetrahedron Letters*, vol. 36, No. 48, 1995, p. 8867-8870.

Comins, Daniel L., et al., "Reduction of N-Acyl-2,3-dihydro-4-pyridones to N-Acyl-4-piperidones Using Zinc/Acetic Acid," *Journal of Organic Chemistry*, vol. 66, 2001, p. 2181-2182.

Montska, Thomas A., et al., "2.2-Trichloroethyl Chlorofomate: A General Reagent for Demethylation of Tertiary Methylamines," *Tetrahedron Letters*, No. 14, 1974, p. 1325-1327.

Comins, Daniel L., et al., Addition of Grignard Reagents to 1-Acyl-4-Methoxypyridinium Salts. An Approach to the Synthesis of Quinolizidinones,: *Tetrahedron Letters*, vol. 27, No. 38, 1986, p. 4549-4552.

Taylor, Edward C., et al., A Convenient Synthesis of 1-Aryl-4-Piperidones,: *International Journal of Methods in Synthetic Organic Chemistry*, No. 8, 1981, p. 606-608.

Boswell, Robert F., et al., "Synthesis of Some N-Carboxylic Acid Derivatives of 3-Phenoxypyrrolidines, 4-Phenoxypiperidines, and 3-Phenoxynortropanes with Muscle Relaxant and Anticonvulsant Activities," *Journal of Medicinal Chemistry*, vol. 17, No. 9, 1974, p. 1000-1008.

Idoux, John P., et al., "Aromatic Fluoroalkoxylation via Direct Aromatic Nucleophilic Substitution," Direct Aromatic Nucleophilic Substitution, *Journal of Organic Chemistry*, vol. 48, No. 21, Oct. 21, 1983, p. 3771-3773.

Gupton, John T., et al., "Regioselective Fluoroalkoxylation and Polyfluoroalkoxylation of Activated Polyhalobenzenes," *Synthetic Communications*, vol. 14, No. 7, 1984, p. 621-629.

Gonzalez, Concepcion, et al., "Chapter 6: Synthesis of Phenols," *The Chemistry of Phenols*, Part 1, 2003, p. 395.489.

McCarthy, James R., et al., "Stereospecific Syntheses of the Four Diastereomeric 2-Amino-5-phenoxycyclopentanols," *Journal of Organic Chemistry*, vol. 50, No. 17, Aug. 23, 1985, p. 3095-3103.

Garner, G.V., et al., "Synthesis of Heterocyclic Compounds, Part XXIV. Cyclisation Studies with ortho-Substituted Arylcarbene and Arylnitrene Precursors," *J. Chem. Soc.*, 1971, p. 3693-3701.

Thomas A. Magee, et al., "Insecticidal Substituted 2-Butanone O-(Methylaminocarbonlyl)oximes," *Journal of Agricultural and Food Chemistry*, 1977, 25, 1376-1382.

Kurtz, et al., "Novel Insecticidal Oxathiolane and Oxathiane Oxime Carbamates," *Journal of Agricultural and Food Chemistry*, 1987, 35, p. 106-114.

Henrick et al., "Ovicidal Activity and its Relation to Chemistry Structure for the Two-spotted Spider Mite (*Tetranychus urticae* Koch) in a New Class of Miticides Containing the Cyclopropyl Group," *Journal of Agricultural and Food Chemistry*, 1976, vol. 24, No. 5, p. 1023-1029.

Dekeyser et al., "Synthesis and Miticidal and Insecticidal Activities of 4-(2-Flurooethyl)—5,6-dihydro—4H-1,3,4—oxadiazines," *Journal of Agricultural and Food Chemistry*, 1993, 41, p. 1329-1331.

Plimmer, Jack R., et al., "Pesticide" Encyclopedia of Agrochemicals, vols. 1-3, Wiley: Hoboken, 2003 p. 1199.

Varma et al., "A Facile One-Pot Synthesis of 2,5-Disubstituted Oxazoles Using Iodobenzene Diaceteate," *J. Heterocyclic Chem.*, vol. 35, pp. 1533-1534, Nov.-Dec. 1998.

Office Action issued in U.S. Appl. No. 12/333,227 dated Feb. 23, 2010.

Office Action issued in U.S. Appl. No. 12/142,637 dated Feb. 25, 2010.

Lohray et al., "Novel Euglycemic and hypolipidemic agents. 4. pyridyl- and quinolinyl-containing thiazolidinediones," *J. Med. Chem*, 1999, vol. 42, pp. 2569-2581.

Chemical abstracts, Lohray et al., "Novel Euglycemic and hypolipidemic agents. 4. pyridyl- and quinolinyl-containing thiazolidinediones,", XP002573019, Database accession No. 1999:384967.

Chemical abstracts, Lohray et al., "Thiazolidinedione compounds having antidiabetic, hypolipidemic, antihypertensive properties, process for their preparation and pharmaceutical compositions," XP002573018, Database accession No. 1999: 430613, pp. 1-2.

International Search Report, International Application No. PCT/JP2005/006887, dated Jun. 21, 2005.

Supplementary Search Report, European Application No. EP 05 72 8646 dated Mar. 26, 2010.

Indian Examination Report, Indian Patent Application No. 2652/KOLNP/2006, dated Jun. 22, 2010.

Office Action, U.S. Appl. No. 12/333,227, dated Jul. 19, 2010.

Office Action, U.S. Appl. No. 12/142,637, dated Aug. 2, 2010.

Search Report, European Patent Application No. 06 81 1453, dated Aug. 3, 2010.

EP Office Action issued for 05728646.0, mailed Jun. 9, 2011, 5 pages.

Israel Office Action with English translation, mailed Jul. 24, 2011, 3 pages.

* cited by examiner

CYCLIC AMINE COMPOUNDS AND AGENTS FOR PEST CONTROL

FIELD OF THE INVENTION

The present invention relates to novel cyclic amine compounds and agents for pest control which contain these cyclic amine compounds or the like as active ingredients.

Priority is claimed on Japanese Patent Application No. 2005-294126, filed Oct. 6, 2005, Japanese Patent Application No. 2005-294127, filed Oct. 6, 2005, Japanese Patent Application No. 2005-297803, filed Oct. 12, 2005, Japanese Patent Application No. 2005-297804, filed Oct. 12, 2005, Japanese Patent Application No. 2006-016877, filed Jan. 25, 2006, and Japanese Patent Application No. 2006-182314, filed Jun. 30, 2006, the contents of which are incorporated herein by reference.

DESCRIPTION OF THE RELATED ART

Although many compounds which have insecticidal/acaricidal activities are conventionally known, there were problems such as insufficient effect thereof, limitation of use thereof because of drug resistance problems, occurrence of phytotoxicity or contamination in plant bodies, or strong toxicity against mammalians, fish, or the like.

The compounds represented by the formula below are known to have insecticidal/acaricidal activities.

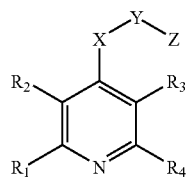

In the formula, X represents O, S, NH, NR, or NOR; Y represents a bond (crosslink) or the like; Z represents C3 to C8-cycloalkyl or the like; and $CH_2$ in these hydrocarbon rings in this case may be substituted with $NR_5$ ($R_5$ is phenyl or substituted phenyl). Known specific examples of such compounds include the compound represented by the formula below (refer to Patent document 1).

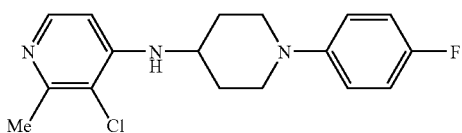

However, the structures of such compounds are limited to 4-aminopyridine derivatives and 4-hydroxypyridine derivatives and no compounds with other structures are specifically disclosed.

[Patent document 1] Published Japanese translation No. Hei 09-502446 of PCT International Publication

DISCLOSURE OF THE INVENTION

Problems to be Solved by the Invention

An object of the present invention is to provide agents for pest control, which can be synthesized industrially favorably, which have excellent bioactivities, which are problem-free in terms of safety, and which have the compounds with novel backbones as active ingredients.

Means for Solving the Problem

As a result of intensive research in order to solve the above problems, the present inventors discovered that novel cyclic amine compounds with a specific structure have excellent insecticidal/acaricidal activities to complete the present invention. In other words, the present invention firstly provides agents for pest control which are characterized by containing cyclic amine compounds represented by the formula (1), salts thereof, or N-oxides thereof, as active ingredients.

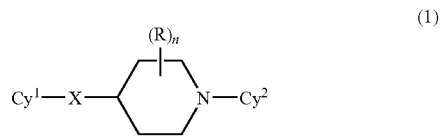

In the formula, $Cy^1$ represents an unsubstituted or substituted 5-membered heterocycle or unsubstituted or substituted group represented by the formula (a) below.

[In the formula, $Y^1$ and $Y^2$ each independently represents nitrogen or carbon and the symbol (*) represents the bonding positions.]

X represents oxygen, sulfur, sulfinyl, sulfonyl, unsubstituted or substituted nitrogen.

Each R may bond to form a ring and R which does not bond to form a ring represents a hydroxyl, halogen, unsubstituted or substituted amino, nitro, or an organic group.

n is an integer from 0 to 9 and each R may be the same or different when n is 2 or more.

$Cy^2$ represents unsubstituted or substituted cyclic hydrocarbon or unsubstituted or substituted heterocycle with a proviso that $Cy^2$ is pyridin-2-yl, which is substituted with at least one or more cyano, when $Cy^1$ is an unsubstituted or substituted phenyl and $Cy^2$ is pyridin-2-yl.

The present invention secondly provides cyclic amine compounds represented by the formula (2), salts thereof, or N-oxides thereof.

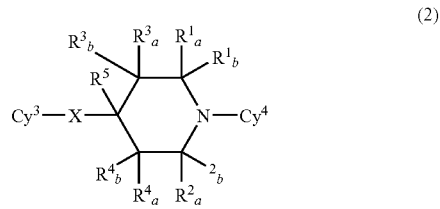

In the formula, $Cy^3$ represents any one of the formulae (b) to (h) below.

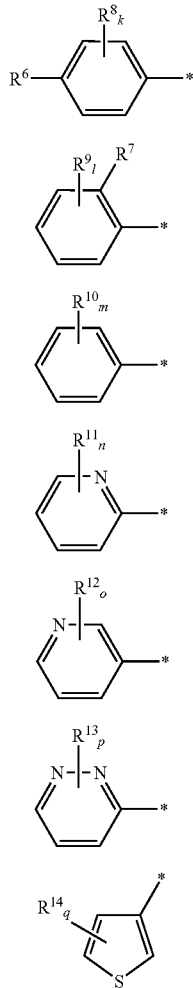

In the formula, $R^6$ represents haloalkyl or haloalkoxy.

$R^7$ represents unsubstituted or substituted alkoxy, unsubstituted or substituted alkoxycarbonyl, unsubstituted or substituted alkoxyalkyl, or the functional group represented by the formula (1) below.

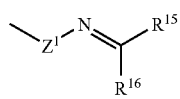

[In the formula, $R^{15}$ and $R^{16}$ each independently represents hydrogen, unsubstituted or substituted hydrocarbon, unsubstituted or substituted heterocyclic group, unsubstituted or substituted amino, hydrocarbonoxy, or hydrocarbonthio. $R^{15}$ and $R^{16}$ may bond to form a ring, in that case, both two groups in the pair represent functional groups, which may integrate to form a ring, and $Z^1$ represents oxygen or unsubstituted or substituted nitrogen.]

$R^8$ to $R^{14}$ each independently represents hydroxyl, thiol, halogen, nitro, formyl, cyano, haloalkyl, haloalkoxy, haloalkenyl, alkyl, (optionally substituted with $G^1$), alkoxy (optionally substituted with $G^1$), alkylcarbonyl, alkoxycarbonyl, alkyl, alkenyloxy, alknyloxy, aryl (optionally substituted with $G^1$), or the functional group represented by the formula (1).

$G^1$ represents hydroxyl, halogen, unsubstituted or substituted amino, nitro, or an organic group.

k, l, n and o each independently represents any one of an integer from 0 to 4 and each $R^8$, $R^9$, $R^{10}$, $R^{11}$, and $R^{12}$ may be the same or different when k, l, n, and o are 2 or more.

m is any one of an integer from 0 to 5 and each $R^{10}$ may be the same or different when m is 2 or more.

p and q each independently represents any one of an integer from 0 to 3 and each $R^{13}$ and each $R^{14}$ may be the same or different when p and q are 2 or more.

X represents oxygen, sulfur, sulfinyl, sulfonyl, or unsubstituted or substituted nitrogen.

$R^1{}_a$ and $R^2{}_a$, $R^1{}_a$ and $R^4{}_a$, $R^2{}_a$ and $R^3{}_a$, or $R^3{}_a$ and $R^4{}_a$ may form saturated rings together and $R^1{}_a$, $R^1{}_b$, $R^1{}_a$, $R^2{}_b$, $R^3{}_a$, $R^3{}_b$, $R^4{}_a$, $R^4{}_b$, and $R^5$ which do not form saturated rings together each independently represents a hydrogen, hydroxyl, halogen, unsubstituted or substituted amino, nitro, or an organic group.

$Cy^4$ represents pyridin-2-yl substituted with one or more cyano, pyridin-3-yl, pyridazin-3-yl, pyrazinyl, thiazol-2-yl, pyrimidin-2-yl, 1,3,4-thiadiazol-2-yl, or phenyl which are optionally substituted with $G^2$ when $Cy^3$ is a functional group represented by the formulae (c), (g), or (h), pyridin-2-yl substituted with one or more cyano, pyridin-3-yl, pyridazin-3-yl, pyrazinyl, thiazol-2-yl, pyrimidin-2-yl, or 1,3,4-thiadiazol-2-yl which are optionally substituted with $G^2$ when $Cy^3$ is a functional group represented by the formulae (b), (e), or (f), and pyridin-2-yl substituted with one or more cyano, pyrazinyl, or 1,3,4-thiadiazol-2-yl which are optionally substituted with $G^2$ when $Cy^3$ is a functional group represented by the formula (d).

$G^2$ represents hydroxyl, halogen, cyano, nitro, formyl, alkyl (optionally substituted with $G^3$), alkoxy (optionally substituted with $G^3$), haloalkyl, haloalkoxy, alkylthiocarbonyl, alkylsulfonylamino, haloalkylsulfonylamino, bis(alkylsulfonyl)amino, bis(haloalkylsulfonyl)amino, alkoxycarbonyl, aryl (optionally substituted with $G^1$), a 5 to 6-membered heterocyclic group (which contain at least one heteroatom out of oxygen, nitrogen, and sulfur), the group represented by the formulae (j) to (l).

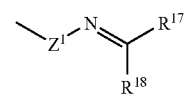

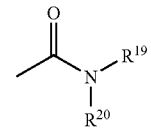

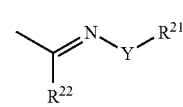

In the formulae (j), (k), and (l), $R^{17}$ and $R^{18}$ each independently represents hydrogen, unsubstituted or substituted hydrocarbon, unsubstituted or substituted heterocyclic group, unsubstituted or substituted amino, hydrocarbonoxy, or hydrocarbonthio. $R^{19}$ and $R^{22}$ each independently represents hydrogen, unsubstituted or substituted hydrocarbon, unsubstituted or substituted heterocyclic group, or unsubstituted or substituted amino. $R^{20}$ represents hydrogen or unsubstituted or substituted hydrocarbon. $R^{21}$ represents hydrogen, unsubstituted or substituted hydrocarbon, or unsubstituted or substituted heterocyclic group. Y and Z each independently represents oxygen or unsubstituted or substituted nitrogen. $R^{17}$ and $R^{18}$, $R^{19}$ and $R^{20}$, and $R^{21}$ and $R^{22}$ may bond to form rings and in that case, both two groups in the pair represent functional groups, which may integrate to form a ring.

$G^3$ represents hydroxyl, cyano, alkoxy, alkoxyalkoxy, or trialkylsilyloxy.

Effects of the Invention

According to the present invention, it is possible to provide agents for pest control with excellent bioactivities especially in terms of insecticidal/acaricidal activities and high safety and furthermore, it is possible to provide cyclic amine compounds with a novel structure, salts thereof, or N-oxides thereof.

PREFERRED EMBODIMENTS OF THE INVENTION

The present invention will be described in detail below.

I. Agents for Pest Control Containing Cyclic Amine Compounds Represented by the Formula (1), Salts Thereof, or N-oxides Thereof as Active Ingredients The agents for pest control of the present invention are characterized by containing cyclic amine compounds represented by the formula (1), salts thereof, or N-oxides thereof, as active ingredients. In the formula (1), $Cy^1$ is an unsubstituted or substituted 5-membered heterocyclic group or an unsubstituted or substituted functional group represented by the formula (a).

The 5-membered heterocyclic group is not particularly limited as long as it is a 5-membered heterocycle having one or more heteroatoms in the ring and it may be saturated or unsaturated. Specific examples thereof include pyrrolidin-2-yl, pyrrolidin-3-yl, furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, and 1,2,4-triazol-5-yl and thiophen-3-yl is preferable.

The formula (a) represents phenyl, pyridin-2-yl, pyridin-3-yl, or pyridazin-3-yl which are unsubstituted or substituted and unsubstituted or substituted phenyl is preferable.

Specific examples of the substituents of $Cy^1$ include hydroxyl; thiol; halogen such as fluorine, chlorine, bromine, and iodine; cyano; nitro; formyl; unsubstituted or substituted amino such as amino, methylamino, benzylamino, anilino, dimethylamino, diethylamino, and phenylethylamino; alkyl (preferably $C_{1-6}$ alkyl) such as methyl, ethyl, n-propyl, isopropyl, n-butyl, sbutyl, isobutyl, t-butyl, n-pentyl, and n-hexyl; alkenyl such as vinyl, allyl, and 2-methoxyethenyl; alkynyl such as ethynyl, 1-propynyl, 2-phenylethynyl, and propargyl; alkoxy (preferably $C_{1-6}$ alkoxy) such as methoxy, ethoxy, propoxy, isopropoxy, n-butoxy, sec-butoxy, isobutoxy, and t-butoxy; alkenyloxy such as vinyloxy and allyloxy; alkynyloxy such as ethynyloxy and propargyloxy; aryloxy such as phenoxy and benzyloxy; heteroaryloxy such as 2-pyridyloxy; haloalkyl (preferably $C_{1-6}$ haloalkyl) such as chloromethyl, fluoromethyl, bromomethyl, dichloromethyl, difluoromethyl, dibromomethyl, trichloromethyl, trifluoromethyl, bromodifluoromethyl, 1,1,1-trifluoroethyl, 1-chloroethyl, 2-chloroethyl, 1-bromoethyl, and 2-bromoethyl, pentafluoroethyl; haloalkoxy (preferably $C_{1-6}$ haloalkoxy) such as fluoromethoxy, chloromethoxy, bromomethoxy, difluoromethoxy, dichloromethoxy, dibromomethoxy, trifluoromethoxy, trichloromethoxy, tribromomethoxy, 1,1,1-trifluoroethoxy, pentafluoroethoxy, and heptafluoroisopropoxy; alkylthiocarbonyl (preferably $C_{1-6}$ alkylthiocarbonyl) such as methylthiocarbonyl, ethylthiocarbonyl, propylthiocarbonyl, isopropylcarbonyl, n-butylthiocarbonyl, isobutylthiocarbonyl, s-butylthiocarbonyl, and t-butylthiocarbonyl; alkylsulfonylamino (preferably $C_{1-6}$ alkylsulfonylamino) such as methylsulfonylamino, ethylsulfonylamino, n-propylsulfonylamino, isopropylsulfonylamino, n-butylsulfonylamino, and t-butylsulfonylamino; arylsulfonylamino (preferably $C_{6-12}$ arylsulfonylamino) such as phenylsulfonylamino; heteroarylsulfonylamino (preferably $C_{3-12}$ heteroarylsulfonylamino) such as piperadinylsulfonylamino; alkylcarbonylamino (preferably $C_{1-6}$ alkylcarbonylamino) such as methylcarbonylamino, ethylcarbonylamino, n-propylcarbonylamino, and isopropylcarbonylamino; alkoxycarbonylamino (preferably $C_{1-6}$ alkoxycarbonylamino) such as methoxycarbonylamino, ethoxycarbonylamino, n-propoxycarbonylamino, and isopropoxycarbonylamino; haloalkylsulfonylamino (preferably $C_{1-6}$ haloalkylsulfonylamino) such as fluoromethylsulfonylamino, chloromethylsulfonylamino, bromomethylsulfonylamino, difluoromethylsulfonylamino, dichloromethylsulfonylamino, difluoroethylsulfonylamino, trifluoromethylsulfonylamino, 1,1,1-trifluoroethylsulfonylamino, and pentafluoromethylsulfonylamino; bis(alkylsulfonyl)amino (preferably bis($C_{1-6}$ alkylsulfonyl)amino) such as bis(methylsulfonyl)amino, bis(ethylsulfonyl)amino, (ethylsulfonyl) (methylsulfonyl)amino, bis(propylsulfonyl) amino, bis(isopropylsulfonyl)amino, bis(n-butylsulfonyl) amino, and bis(t-butylsulfonyl)amino; bis(haloalkylsulfonyl) amino (preferably bis($C_{1-6}$ haloalkylsulfonyl)amino) such as bis(fluoromethylsulfonyl)amino, bis(chloromethylsulfonyl) amino, bis(bromomethylsulfonyl)amino, bis(difluoromethylsulfonyl)amino, bis(dichloromethylsulfonyl)amino, bis(difluoroethylsulfonyl)amino, bis(trifluoromethylsulfonyl) amino, bis(1,1,1-trifluoroethylsulfonyl)amino, and bis (pentafluoroethylsulfonyl)amino; unsubstituted or substituted hydrazinomethoxycarbonyl such as hydrazino, N'-phenylhydrazino, and N'-methoxycarbonylhydrazino; alkoxycarbonyl (preferably $C_{1-6}$ alkoxycarbonyl) such as ethoxycarbonyl, propoxycarbonyl, isopropoxycarbonyl, n-butoxycarbonyl, and t-butoxycarbonyl; aryl (preferably $C_{6-12}$ aryl) such as phenyl, 1-naphthyl, and 2-naphthyl; aralkyl (preferably $C_{7-20}$ aralkyl) such as benzyl, and phenethyl; unsaturated 5-membered heterocycle such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, and 1,2,4-triazol-5-yl; unsaturated 5-membered heterocycle alkyl such as 5-phenyl-5-trifluoromethyl-isoxazolin-3-yl, 2-furfurylmethyl, 3-thienylmethyl, 1-methyl-3-pyrazolomethyl; unsaturated 6-membered heterocycle such as pyridin-2-yl, pyridin-3-yl, pyridin-4-yl, pyridazin-3-yl, pyridazin-4-yl, pyrazin-2-yl, pyrimidin-2-yl, pyrimidin-4-yl, pyrimidin-5-yl, 1,3,5-triazin-2-yl, and 1,2,4-triazin-3-yl; unsaturated 6-membered heterocycle alkyl such as 2-pyridylmethyl, 3-pyridylmethyl, 6-chlor-3-pyridylmethyl, and 2-pyrimidylmethyl; saturated heterocyclic group such as tetrahydrofuran-2-yl, tetrahydrapyran-4-yl, piperidin-3-yl, pyrrolidin-2-yl, morpholino, piperidino, and N-methylpiperazinyl; saturated heterocyclic alkyl group such as 2-tetrahydrafuranylmethyl, 3-piperazylmethyl, N-methyl-3-pyrrolidylmethyl, and morpholinomethyl; N-unsubstituted- or N-substituted iminoalkyl such as N-dimethylaminoiminomethyl, 1-N-phenyliminoethyl, N-hydroxyiminomethyl, and N-methoxyiminomethyl; N-unsubstituted- or N-substituted hydrazinocarbonyl such as N'-methylhydrazinocarbonyl, N'-phenylhydrazinocarbonyl, and hydrazinocarbonyl; N-unsubstituted- or N-substituted aminocarbonyl such as aminocarbonyl, dimethylaminocarbonyl, and N-phenyl-N-methylaminocarbonyl; N-unsubstituted- or N-substituted hydrazino such as hydrazino, N'-acetylhydrazino, N'-methylhydrazino, N'-phenylhydrazino, N'-methoxycarbonylhydrazino, and N'-2-propylidenehydrazino; alkylthio such as methylthio, ethylthio, and t-butylthio; alkenylthio such as vinylthio and allylthio; alkynylthio such as ethynylthio and propargylthio; arylthio such as phenylthio, and 4-chlorophenylthio; heteroarylthio such as 2-pyridylthio; aralkylthio such as benzylthio and phenethylthio; alkylsulfonyl such as methylsulfonyl, ethylsulfonyl, and t-butylsulfonyl; alkenylsulfonyl such as allylsulfonyl; alkynylsulfonyl such as propargylsulfonyl; arylsulfonyl such as phenylsulfonyl; heteroarylsulfonyl such as 2-pyridylsulfonyl and 3-pyridylsulfonyl; aralkylsulfonyl such as benzylsulfonyl; and functional groups represented by the formula (i). By associating two or more substituents listed above by substituting one substituent onto another, the resulting substituent can be used in a similar manner as a new substituent.

Specific examples of hydrocarbons in the formula (1) include alkyl such as methyl, ethyl, isopropyl, n-propyl, n-hexyl, and n-octyl; alkenyl such as vinyl, allyl, 1-propenyl, and 2-phenylethenyl; alkynyl such as ethynyl and propargyl; and aromatic hydrocarbon such as phenyl, 1-naphthyl, and 9-anthracel. Specific examples of heterocyclic groups include unsaturated 5-membered heterocycle such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, and 1,2,4-triazol-5-yl; unsaturated 5-membered heterocycle alkyl such as 5-phenyl-5-trifluoromethylisoxazolin-3-yl, 2-furfurylmethyl, 3-thienylmethyl, and 1-methyl-3-pyrazolomethyl; unsaturated 6-membered heterocycle such as pyridin-2-yl, pyridin-3-yl, pyridin-4-yl, pyridazin-3-yl, pyridazin-4-yl, pyrazin-2-yl, pyrimidin-2-yl, pyrimidin-4-yl, pyrimidin-5-yl, 1,3,5-triazin-2-yl, and 1,2,4-triazin-3-yl; unsaturated 6-membered heterocycle alkyl such as 2-pyridylmethyl, 3-pyridylmethyl, and 6-chlor-3-pyridylmethyl; and saturated heterocycle such as tetrahydrofuran-2-yl, tetrahydrapyran-4-yl, piperidin-3-yl, pyrrolidin-2-yl, morpholino, piperidino, and N-methylpiperazinyl; saturated heterocycle alkyl such as 2-tetrahydrafuranylmethyl, 3-piperazylmethyl, N-methyl-3-pyrrolidylmethyl, and morpholinomethyl. Specific examples of hydrocarbonoxy and hydrocarbonthio include methoxy, ethoxy, isopropoxy, phenoxy, benzyloxy, 2-pyridyloxy, methylthio, ethylthio, phenylthio, benzylthio, and 2-pyridylthio. Specific examples of substituents of functional groups present in $R^6$ and $R^7$ include the same as those shown as specific examples of the substituents of $Cy^1$. Specific examples of functional groups represented by the formula (i) include the functional groups represented by the formulae below.

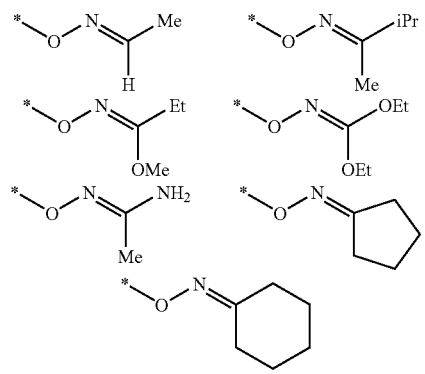

$Y^1$ and $Y^2$ each independently represents nitrogen or carbon.

X represents oxygen; sulfur; unsubstituted nitrogen or nitrogen substituted with the same substituents as those listed as specific examples of the substituents of $Cy^1$; sulfinyl; or sulfonyl and oxygen is particularly preferable.

Each R may form saturated rings together and the bonding of those at second and sixth positions and at third and fifth positions of the piperidine ring to form saturated rings is preferable and the number of atoms at the cross-linking site, which forms the saturated ring, is preferably 2 or 3. In addition, elements which constitute the cross-linking site of the saturated ring are not particularly limited as long as they are within a chemically acceptable range and specific examples thereof include carbon, oxygen, sulfur, nitrogen, or silicon and the saturated rings can be constituted by combining 2 or more of these elements within a chemically acceptable range. Moreover, each atom can have hydrogen or substituents within the chemically acceptable range thereon and $R^1_a$ and $R^2_a$, $R^1_a$ and $R^4_a$, $R^2_a$ and $R^3_a$, or $R^3_a$ and $R^4_a$ may bind oxygen, sulfur, or nitrogen via a double bond within a chemically acceptable range to form carbonyl, thiocarbonyl, imino, or the like.

R which does not form the aforementioned saturated rings together each independently represents hydrogen, halogen, unsubstituted or substituted amino, nitro, hydroxyl, or an organic group. Specific examples of the organic group include cyano; formyl; alkyl, alkoxycarbonyl, alkoxy, haloalkyl, haloalkoxy, alkylthiocarbonyl, alkylsulfonylamino, haloalkylsulfonylamino, bis(alkylsulfonyl)amino, bis(haloalkylsulfonyl)amino, alkoxycarbonyl, and aryl. Alkyl, alkoxycarbonyl, and alkoxy are preferable as the organic group and $C_{1-6}$ alkyl, $C_{1-6}$ alkoxycarbonyl, and $C_{1-6}$ alkoxy are more preferable. Specific examples thereof include the same as those shown as a part of specific examples of the substituents of $Cy^1$.

n is an integer from 0 to 9 and each R may be the same or different when n is 2 or more.

Moreover, each R may bond to form a ring and the number of atoms at the cross-linking site, which forms the saturated ring, is preferably 2 or 3.

$Cy^2$ represents unsubstituted or substituted cyclic hydrocarbon, or unsubstituted or substituted heterocycle. Specific examples thereof include aromatic hydrocarbons such as phenyl, naphthyl-1-yl, and naphthyl-2-yl; and heteroaromatic rings such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol- 5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, 1,2,4-triazol-5-yl, pyridin-2-yl, pyridin-3-yl, pyridin-4-yl, pyridazin-3-yl, pyridazin-4-yl, pyrazin-2-yl, pyrimidin-2-yl, pyrimidin-4-yl, pyrimidin-5-yl, 1,3,5-triazin-2-yl, and 1,2,4-triazin-3-yl; and pyridazin-3-yl is preferable. Specific examples of the non-aromatic rings include cycloalkyl such as cyclopropyl, cyclobutyl, and cyclopentyl; and saturated heterocycle such as piperidino, 2-piperidyl, 3-piperidyl, 4-piperidyl, 2-tetrahydrofuranyl, 3-tetrahydrofuranyl, 2-tetrahydropyranyl, 3-tetrahydropyranyl, 4-tetrahydropyranyl, 2-pyrrolidinyl, 3-pyrrolidinyl, 2-piperidinyl, 3-piperidinyl, 4-piperidinyl, 2-piperazinyl, 3-piperazinyl, and 4-piperazinyl and pyridazin-3-yl is particularly preferable.

Specific examples of the substituents of $Cy^2$ include substituents the same as the specific examples of the substituents of $Cy^1$. It is with a proviso that $Cy^2$ is a pyridin-2-yl which is substituted with one or more cyano when $Cy^1$ is an unsubstituted or substituted phenyl and $Cy^2$ is an substituted pyridin-2-yl. $Cy^2$ does not include unsubstituted pyridin-2-yl, when $Cy^1$ is an unsubstituted or substituted phenyl. The pyridin-2-yl which is substituted with one cyano may have a substituent other than cyano.

II. Novel Cyclic Amine Compounds Represented by the Formula (2)

In the novel cyclic amine compounds represented by the formula (2) (which may hereinafter be referred to as the "compound (2)"), $Cy^3$ is a functional group represented by any one of the formulae (b) to (h).

In the formula (b), specific examples of $R^6$ include substituents the same as a part of the specific examples of the substituents of $Cy^1$.

Specific examples of $R^7$ in formula (c) include alkoxy (particularly preferably $C_{1-6}$ alkoxy) and alkoxycarbonyl (particularly preferably $C_{1-6}$ alkoxycarbonyl) which are the same as part of the specific examples of the substituents of $Cy^1$, a functional group represented by the formula (1), which is the same as above; and alkoxyalkyl (particularly preferably $C_{1-6}$ alkoxy $C_{1-6}$ alkyl) such as methoxymethyl, ethoxymethyl, propoxymethyl, 1-methoxyethyl, 2-methoxyethyl, 1-ethoxyethyl, 2-ethoxyethyl, 1-propoxyethyl, 2-propoxyethyl, 1-methoxypropyl, 2-methoxypropyl, and 3-methoxypropyl.

Specific examples of $R^8$ to $R^{14}$ include those the same as part of the specific examples of the substituents of $Cy^1$.

Specific examples of $G^1$, which may be a substituent of a part of $R^8$ to $R^{14}$, include those the same as part of the specific examples of the substituents of $Cy^1$.

Specific examples of the substituents of nitrogen include those the same as the specific examples of the substituents of $Cy^1$ when X is optionally substituted nitrogen.

Moreover, $R^1{}_a$ and $R^2{}_a$, $R^1{}_a$ and $R^4{}_a$, $R^2{}_a$ and $R^3{}_a$, or $R^3{}_a$ and $R^4{}_a$ may form saturated rings together and it is preferable that $R^1{}_a$ and $R^2{}_a$ or $R^3{}_a$ and $R^4{}_a$ come together to form a ring when forming saturated rings and the number of atoms at the cross-linking site, which forms the saturated ring, is preferably 2 or 3. In addition, elements which constitute the cross-linking site of the saturated ring are not particularly limited as long as they are within a chemically acceptable range and specific examples thereof include carbon, oxygen, sulfur, nitrogen, or silicon and the saturated rings can be constituted by combining 2 or more of these elements within a chemically acceptable range. Moreover, each atom can have hydrogen or substituents within the chemically acceptable range thereon and $R^1{}_a$ and $R^2{}_a$, $R^1{}_a$ and $R^4{}_a$, $R^2{}_a$ and $R^3{}_a$, or $R^3{}_a$ and $R^4{}_a$ may bind oxygen, sulfur, or nitrogen via a double bond within a chemically acceptable range to form carbonyl, thiocarbonyl, imino, or the like.

$R^1{}_a$, $R^1{}_b$, $R^2{}_a$, $R^2{}_b$, $R^3{}_a$, $R^3{}_b$, $R^4{}_a$, $R^4{}_b$, and $R^5$ which do not form the aforementioned saturated rings together each independently represents hydrogen, halogen, unsubstituted or substituted amino, nitro, hydroxyl, or an organic group. The organic group represents functional groups generally which contain carbon and the specific examples thereof include cyano; formyl; alkyl; alkoxycarbonyl; alkoxy; haloalkyl, haloalkoxy; alkylthiocarbonyl; alkylsulfonylamino; haloalkylsulfonylamino; bis(alkylsulfonyl)amino; bis(haloalkylsulfonyl)amino; alkoxycarbonyl; and aryl. Alkyl, alkoxycarbonyl, and alkoxy are preferable as the organic group and $C_{1-6}$ alkyl, $C_{1-6}$ alkoxycarbonyl, and $C_{1-6}$ alkoxy are more preferable. Furthermore, specific examples thereof include the same as those shown as a part of specific examples of the substituents of $Cy^1$.

A part of specific examples of $G^2$ in $Cy^4$ include those the same as part of the specific examples of the substituents of $Cy^1$. Specific examples of hydrocarbons commonly present in $R^{17}$ to $R^{22}$ in the formulae (j) to (l) in $G^2$ include alkyl such as methyl, ethyl, isopropyl, n-propyl, n-hexyl, and n-octyl; alkenyl such as vinyl, allyl, 1-propenyl, and 2-phenylethenyl; alkynyl such as ethynyl and propargyl; and aromatic hydrocarbon such as phenyl, 1-naphthyl, and 9-anthracel.

Specific examples of heterocyclic groups commonly present in $R^{17}$, $R^{18}$, $R^{19}$, $R^{21}$, and $R^{22}$ include unsaturated 5-membered heterocycle such as furan-2-yl, furan-3-yl, thiophen-2-yl, thiophen-3-yl, pyrrol-2-yl, pyrrol-3-yl, oxazol-2-yl, oxazol-4-yl, oxazol-5-yl, thiazol-2-yl, thiazol-4-yl, thiazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, pyrazol-3-yl, pyrazol-4-yl, pyrazol-5-yl, 1,3,4-oxadiazol-2-yl, 1,3,4-thiadiazol-2-yl, 1,2,3-triazol-4-yl, 1,2,4-triazol-3-yl, 1,2,4-triazol-5-yl, 5-phenyl-5-trifluoromethyl-isoxazolin-3-yl; unsaturated 5-membered heterocycle alkyl such as 2-furfurylmethyl, 3-thienylmethyl, and 1-methyl-3-pyrazolomethyl; unsaturated 6-membered heterocycle such as pyridin-2-yl, pyridin-3-yl, pyridin-4-yl, pyridazin-3-yl, pyridazin-4-yl, pyrazin-2-yl, pyrimidin-2-yl, pyrimidin-4-yl, pyrimidin-5-yl, 1,3,5-triazin-2-yl, 1,2,4-triazin-3-yl; unsaturated 6-membered heterocycle alkyl such as 2-pyridylmethyl, 3-pyridylmethyl, 6-chlor-3-pyridylmethyl, and 2-pyrimidylmethyl; and saturated heterocycle such as tetrahydrofuran-2-yl, tetrahydrapyran-4-yl, piperidin-3-yl, pyrrolidin-2-yl, morpholino, piperidino, N-methylpiperazinyl; saturated heterocycle alkyl such as 2-tetrahydrafuranylmethyl, 3-piperazylmethyl, N-methyl-3-pyrrolidylmethyl, and morpholinomethyl. Specific examples of hydrocarbonoxy and hydrocarbonthio commonly present in $R^{17}$ and $R^{18}$ include methoxy, ethoxy, isopropoxy, phenoxy, benzyloxy, 2-pyridyloxy, methylthio, ethylthio, phenylthio, benzylthio, and 2-pyridylthio. Specific examples of substituents of functional groups present in $R^{17}$ to $R^{22}$ include the same as those shown as specific examples of the substituents of $Cy^1$. Y and Z each independently represent oxygen, or unsubstituted or substituted nitrogen and specific examples of a substituent on nitrogen include the same as those shown as specific examples of the substituents of $Cy^1$.

Specific examples of $G^3$ as a substituent of alkyl and alkoxy in $G^2$ include hydroxyl; cyano; alkoxy (preferably $C_{1-6}$ alkoxy) the same as the specific examples of the substituents of $Cy^1$; alkoxyalkoxy (preferably $C_{1-6}$ alkoxy $C_{1-6}$ alkoxy) such as methoxymethoxy, ethoxymethoxy, and propoxy-ethoxy; and trialkylsilyloxy (preferably tri-$C_{1-6}$ alkylsilyloxy) such as trimethylsilyloxy, triisopropylsilyloxy, and diisopropylmethylsilyloxy.

Specific examples of the formulae (j) to (l) include the formulae shown below.

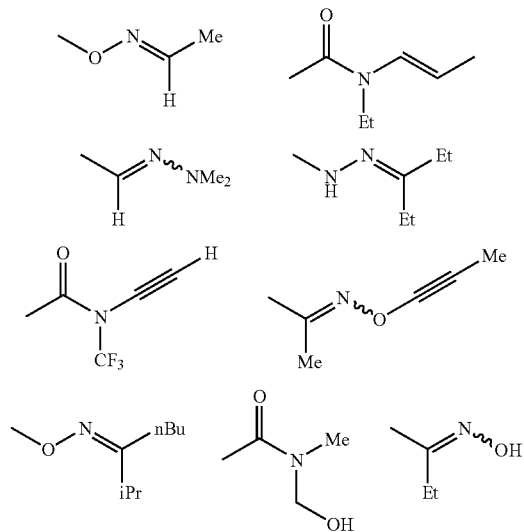

As N-oxides of the compounds represented by the formulae (1) and (2), the compounds where nitrogen in the cyclic amine parts or nitrogen in the nitrogen-containing heterocycle of the compounds represented by the formulae (1) and (2) is oxidized, or the like can be shown as examples.

Moreover, examples of salts of the compounds represented by the formulae (1) and (2) include salts of inorganic acids such as hydrochloride salts, nitrate salts, sulfate salts, and phosphate salts; and salts of organic acids such as acetate salts, lactate salts, propionate salts, and benzoate salts.

III. (Production Method)

The production method of the compounds (1) and (2) will be described next.

It should be noted that although the description is provided below by taking the compound (2) as an example, the compound (1) can also be produced in a similar way as that of the compound (2).

1) When X is Oxygen or Optionally Oxidized Sulfur

The compound (2) can be obtained by, for example, subjecting the compound represented by the formula (3) (hereinafter referred to as the "compound (3)) to general deprotection and coupling as shown below.

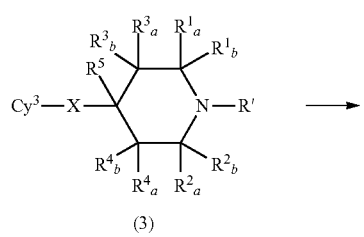

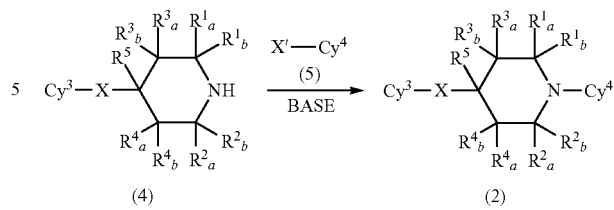

(In the formula, $Cy^3$, $Cy^4$, X, $R^1_a$, $R^1_b$, $R^2_a$, $R^2_b$, $R^3_a$, $R^3_b$, $R^4_a$, $R^4_b$, and $R^5$ are the same as above. X' represents a leaving group such as halogen and R' represents a protecting group.)

The compound (3), which is an intermediate during the production, can be produced by general reaction as described next.

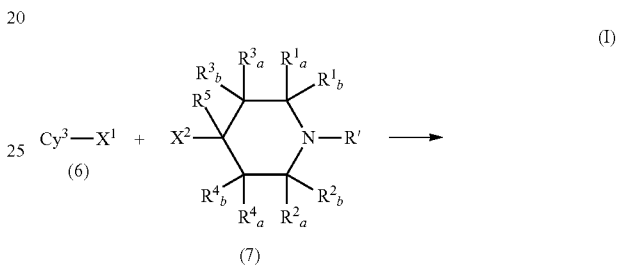

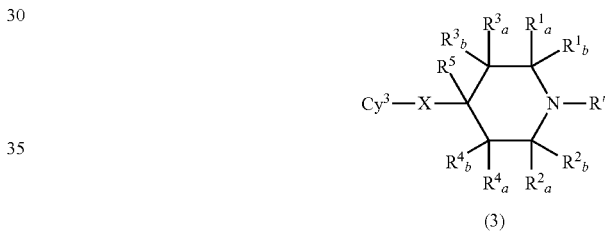

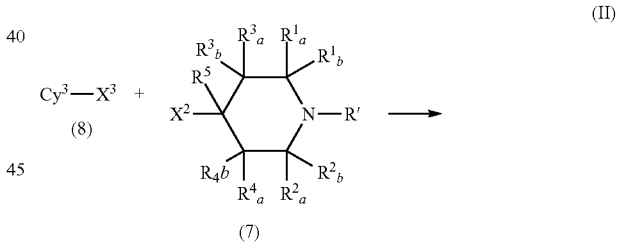

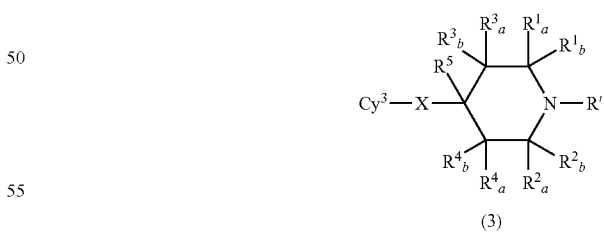

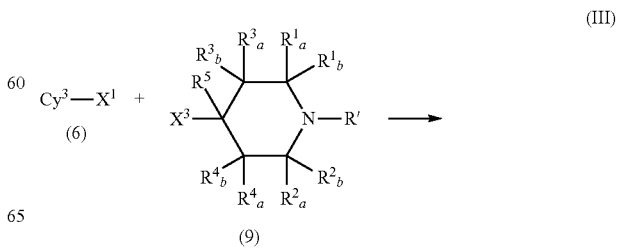

-continued

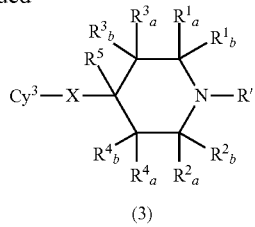
(3)

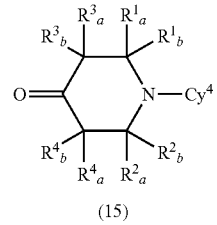
(15)

(In the formula, $Cy^3$, X, $R^1_a$, $R^1_b$, $R^2_a$, $R^2_b$, $R^3_a$, $R^3_b$, $R^4_a$, $R^4_b$, $R^5$ and R' are the same as above. $X^1$ and $X^2$ each independently represents hydroxyl or mercapto and $X^3$ represents a leaving group such as halogen.)

Moreover, the compound (2) can also be produced by the general method shown below.

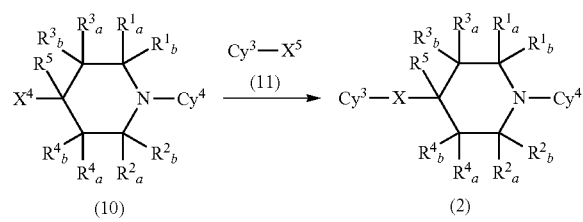

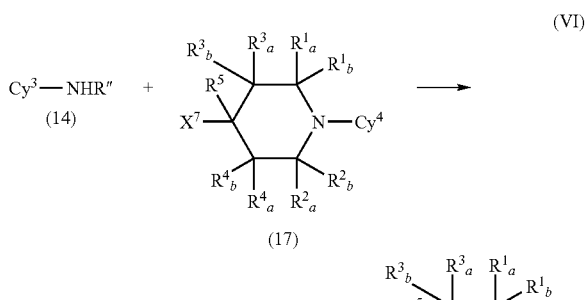
(16)

(In the formula, $Cy^3$, $Cy^4$, $R^1_a$, $R^1_b$, $R^2_a$, $R^2_b$, $R^3_a$, $R^3_b$, $R^4_a$, $R^4_b$ and $R^5$ are the same as above. R" represents a substituent on nitrogen such as hydrogen, trifluoroacetyl, or trifluoromethylsulfonyl.)

The compound (16) which is a compound of the present invention can also be produced by the general reaction as shown in the below reaction formula (VI).

(In the formula, $Cy^3$, $Cy^4$, X, $R^1_a$, $R^1_b$, $R^2_a$, $R^2_b$, $R^3_a$, $R^3_b$, $R^4_a$, $R^4_b$, and $R^5$ are the same as above. $X^4$ represents a leaving group such as halogen and $X^5$ represents hydroxyl or mercapto.)

The compound (10), which will be a raw material, can be produced by the general reaction shown in the below reaction formula (IV).

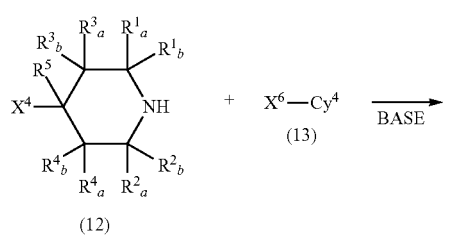

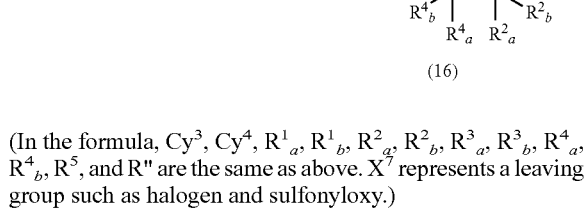
(17)

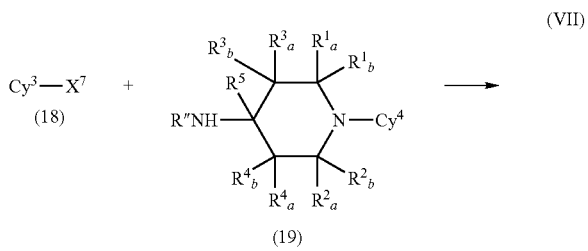
(16)

(In the formula, $Cy^3$, $Cy^4$, $R^1_a$, $R^1_b$, $R^2_a$, $R^2_b$, $R^3_a$, $R^3_b$, $R^4_a$, $R^4_b$, $R^5$, and R" are the same as above. $X^7$ represents a leaving group such as halogen and sulfonyloxy.)

The compound (16) which is a compound of the present invention can also be produced by the general coupling reaction as shown in the below reaction formula (VII).

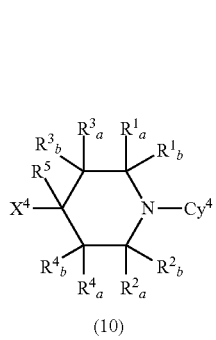
(10)

(In the formula, $Cy^4$, $X^4$, $R^1_a$, $R^1_b$, $R^2_a$, $R^2_b$, $R^3_a$, $R^3_b$, $R^4_a$, $R^4_b$, and $R^5$ are the same as above. $X^6$ represents a leaving group such as halogen.)

2) When X is Optionally Substituted Nitrogen

The compounds represented by the formula (16) (hereinafter referred to as the "compound (16)") can be produced by the general method as shown in the below reaction formula (V).

-continued

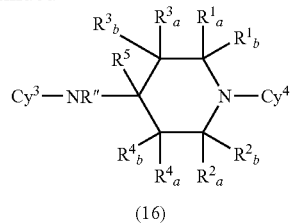

(16)

(In the formula, $Cy^3$, $Cy^4$, $R^1_a$, $R^1_b$, $R^2_a$, $R^2_b$, $R^3_a$, $R^3_b$, $R^4_a$, $R^4_b$, $R^5$, R" and $X^7$ are the same as above.)

IV. Agents for Pest Control Characterized by Containing the Cyclic Amine Compounds Represented by the Formula (1) or (2), Salts Thereof, or N-Oxides Thereof, as Active Ingredients The compounds of the present invention (the compounds represented by the formulae (1) and (2), salts thereof, or N-oxides thereof) have excellent adulticidal, nymphicidal, larvicidal, or ovicidal activities and can be used for controlling pests in agriculture, sanitary insects, stored grain pest insects, clothes pests, household pests, or the like. Representative examples thereof include the following.

Pests which belong to the order of Lepidoptera such as *Spodoptera litura*, *Mamestra brassicae*, *Agrotis ipsilon*, green caterpillars, *Autographa nigrisigna*, *Plutella xylostella*, *Adoxophyes honmai*, *Homona magnanima*, *Carposina sasakii*, *Grapholita molesta*, *Phyllocnistis citrella*, *Caloptilia theivora*, *Phyllonorycter ringoniella*, *Lymantria dispar*, *Euproctis pseudoconspersa*, *Chilo suppressalis*, *Cnaphalocrocis medinalis*, *Ostrinia nubilalis*, *Hyphantria cunea*, *Cadra cautella*, genus *Heliothis*, genus *Helicoverpa*, genus *Agrothis*, *Tinea translucens*, *Cydia pomonella*, and *Pectinophora gossypiella*;

pests which belong to the order of Hemiptera such as *Myzus persicae*, *Aphis gossypii*, *Lipaphis erysimi*, *Rhopalosiphum padi*, *Riptortus clavatus*, *Nezara antennata*, *Unaspis yanonensis*, *Pseudococcus comstocki*, *Trialeurodes vaporariorum*, *Bemisia tabaci*, *Bemisia argentifolii*, *Psyllapyrisuga*, *Stephanitis nashi*, *Nilaparuata lugens*, *Laodelphax stratella*, *Sogatella furcifera*, and *Nephotettix cincticeps*;

pests which belong to the order of Coleoptera such as *Phyllotreta striolata*, *Aulacophora femoralis*, *Leptinotarsa decemlineata*, *Lissorhoptrus oryzophilus*, *Sitophilis zeamais*, *Callosobruchus chinensis*, *Popilliajaponica*, *Anomala rufocuprea*, genus *Diabrotica*, *Lasioderma serricorne*, *Lyctus brunneus*, *Monochamus alternatus*, *Anoplophora malasiaca*, genus *Agriotis*, *Epilachna vigintioctopunctata*, *Tenebroides mauritanicus*, and *Anthonomus grandis*;

pests which belong to the order of Diptera such as *Musca domestica*, *Calliphora lata*, *Boettcherisca peregrine*, *Zeugodacus cucurbitae*, *Bactrocera dorsalis*, *Delia platura*, *Agromyza oryzae*, *Drosophila melanogaster*, *Stomoxys calcitrans*, *Culex tritaeniorhynchus*, *Aedes aegypti*, and *Anopheles sinensis*;

pests which belong to the order of Thysanoptera such as *Thrips palmi* and *Scirtothrips dorsalis*;

pests which belong to the order of Hymenoptera such as *Monomorium pharaonis*, *Vespa simillima xanthoptera*, and *Athalia rosae ruficornis*;

pests which belong to the order of Orthoptera such as *Locusta migratoria*, *Blattella germanica*, *Periplaneta americana*, and *Periplaneta fuliginosa*;

pests which belong to the order of Isoptera such as *Coptotermes formosanus* and *Reticulitermes speratus speratus*;

pests which belong to the order of Siphonaptera such as *Pulex irritans* and *Ctenocephalides felis felis*;

pests which belong to the order of Phthiraptera such as *Pediculus humanus*; Acarina such as *Tetranychus urticae*, *Tetranychus cinnabarinus*, *Tetranychus kanzawai*, *Panonychus citri*, *Panonychus ulmi*, *Aculopspelekassi*, *Aculus schlechtendali*, *Polyphagotarsonemus latus*, genus *Brevipalpus*, genus *Eotetranichus*, *Rhizoglyphus robini*, *Tyrophagus putrescentiae*, *Dermatophagoides farinae*, *Boophilus microplus*, and *Haemaphysalis longicornis*; and plant parasitic nematodes such as *Meloidogyne incognita*, *Pratylenchus* spp., *Heterodera glycines*, *Aphelenchoides besseyi*, and *Bursaphelenchus xylophilus*.

Pests to which the present invention is preferably applied are pests which belong to the order of Lepidoptera, pests which belong to the order of Hemiptera, Acarina, pests which belong to the order of Thysanoptera, and pests which belong to the order of Coleoptera, and particularly preferably Acarina.

Moreover, drugs which are also effective for pests or *Acarnia* that are of resistant lineage are desired because in recent years, resistance to organophosphorus pesticides, carbamate pesticides, or acaricides developed among many pests such as *Plutella xylostella*, Delphacidae, Deltocephalidae, and Aphididae has caused problems because of insufficient effects of these drugs. The compounds of the present invention are drugs having excellent insecticidal and acaricidal effects not only on those of sensitive lineages but also on pests of lineages resistant to organophosphorus pesticides, carbamate pesticides, and pyrethroid pesticides, and on *Acarnia* of lineages resistant to acaricides.

The compounds of the present invention are drugs that show less herbicide injuries, have lower toxicity to fish and warm-blooded animals, and with higher safety.

The compounds of the present invention can also be used as an antifoulant to prevent aquatic organisms attaching to objects which contact water such as ship bottoms and fishing nets.

Moreover, some of the compounds of the present invention exhibit microbiocidal activities, herbicidal activities, or plant-growth regulating activities. Furthermore, some intermediates of the compounds of the present invention exhibit insecticidal/acaricidal activities.

Although the compounds of the present invention are, needless to say, sufficiently effective even when used solely, they can also be used by mixing or combining with one or more of other agents for pest control, germicides, insecticides/acaricides, herbicides, plant growth regulators, synergists, fertilizers, soil conditioners, animal feed, or the like.

Representative examples of active ingredients of germicides, acaricides, plant growth regulators, or the like which can be used by mixing or combining with the compounds of the present invention are shown below.

Germicides:

captan, folpet, thiuram, ziram, zineb, maneb, mancozeb, propineb, polycarbamate, chlorothalonin, quintozene, captafol, iprodione, procymidone, fluoroimide, mepronil, flutolanil, pencycuron, oxycarboxin, fosetyl-aluminum, propamocarb, triadirnefon, triadimenol, propiconazole, diclobutrazol, bitertanol, hexaconazole, myclobutanil, flusilazole, etaconazole, fluotrimazole, flutriafen, penconazole, diniconazole, cyproconazole, fenarimol, triflumizole, prochloraz, imazalil, pefurazoate, tridemorph, fenpropimorph, triforine, buthiobate, pyrifenox, anirazine, polyoxins, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentinacetate, triphenyltin hydroxide, diethofencarb, chinomethionat, binapacryl, lecithin, baking soda, dithianon, dinocap, fenaminosulf, diclomezine, guazatine, dodine, IBP, edifenphos, mepanipyrim, fermzone, trichlamide, methasulfocarb, fluazinam, ethoquinolac, dimethomorph, pyroquilon, tecloftalam, phthalide, phenazine oxide, thiabendazole, tricyclazole, vinclozolin, cymoxanil, cyclobutanil, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole, and carpropamid;

Insecticides/acaricides:
organophosphorus and carbamate pesticides:

fenthion, fenitrothion, diazinon, chlorpyrifos, ESP, vamidothion, phenthoate, dimethoate, formothion, malathion, trichlorphon, thiometon, phosmet, dichlorvos, acephate, EPBP, methyl parathion, oxydemeton methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb, cartap, thiocyclam, bensultap, and the like; pyrethroid pesticides:

permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, and acrinathrin;

Benzoylurea and other Pesticides:

diflubenzuron, chlorfluazuron, hexaflumuron, triflumuron, flufenoxuron, flucycloxuron, buprofezin, pyriproxyfen, methoprene, benzoepin, diafenthiuron, imidacloprid, fipronil, nicotine sulfate, rotenone, metaldehyde, acetamiprid, chlorfenapyr, nitenpyram, thiacloprid, clothianidin, thiamethoxam, dinotefuran, indoxacarb, pymetrozine, spinosad, emamectin, pyridalyl, tebufenozide, chromafenozide, methoxyfenozide, tolfenpyrad, machine oil, microbial pesticides such as BT and entomopathogenic viruses;

Nematicides:
fenamiphos, fosthiazate, cadusafos, and the like;

Acaricides:
chlorobenzilate, phenisobromolate, dicofol, amitraz, BPPS, benzomate, hexythiazox, fenbutatin oxide, polynactin, chinomethionat, CPCBS, tetradifon, avermectin, milbemectin, clofentezine, cyhexatin, pyridaben, fenpyroximate, tebufenpyrad, pyrimidifen, fenothiocarb, dienochlor, fluacrypyrim, acequinocyl, bifenazate, etoxazole, spirodiclofen, fenazaquin, and the like; plant growth regulators:

gibberellins (for example, gibberellin A3, gibberellin A4, or gibberellin A7), IAA, NAA, or the like.

Agents for pest control of the present invention contain one or more compounds of the present invention as an active ingredient.

Although the compounds of the present invention can be used as they are without adding any other components as agents for pest control, they can be formulated for use. In other words, by mixing at least one of the compounds of the present invention with solid, liquid, or gaseous carriers, or by impregnating at least one of the compounds of the present invention in substrates such as porous ceramic plates and nonwoven fabrics, and by adding surfactants or other adjuvants where necessary, the compounds are formulated, with the objective to use as agrochemicals, into the form which general agrochemicals may adopt and can be used.

Examples of agrochemical formulations include wettable powder, granule, dusting powder, emulsion, water-soluble powder, suspending agent, granulated wettable powder, floable, aerosol, transpiration agent by heating, fumigant, poison bait, microcapsule, or the like.

As additives and carriers, vegetable powders such as soy flour and wheat flour; fine mineral powder such as diatomaceous earth, apatite, gypsum, talc, bentonite, pyrophyllite, and clay; and organic and inorganic compounds such as sodium benzoate, urea, and sodium sulfate are used when solid formulation is required. When liquid form of formulation is required, petroleum fractions such as kerosene, xylene, and solvent naphtha, and cyclohexane, cyclohexanone, dimethylformamide, dimethyl sulfoxide, alcohol, acetone, methyl isobutyl ketone, mineral oil, vegetable oil, water, or the like are used as a solvent. As gaseous carriers used in propellant, butane (gas), LPG, dimethyl ether, and carbon dioxide gas can be used.

As a substrate of poison bait, bait components such as grain powder, vegetable oil, sugar, and crystalline cellulose; antioxidants such as dibutylhydroxytoluene and nordihydroguaiaretic acid; preservatives such as dehydroacetic acid; agents for preventing accidental ingestion by children or pets such as *capsicum* powder; and pest-insect attracting scents such as cheese scents and onion scents can be used.

Additionally, in order to achieve homogenous and stable forms in these formulations, it is also possible to add surfactants if necessary. Although surfactants are not particularly limited, examples thereof include, for instance, nonionic surfactants such as alkyl ether where polyoxyethylene is added, higher fatty acid ester where polyoxyethylene is added, sorbitan higher fatty acid ester where polyoxyethylene is added, and tristyryl phenyl ether where polyoxyethylene is added; sulfate ester salt of alkyl phenyl ether where polyoxyethylene is added, alkyl naphthalene sulfonate salt, polycarboxylate salt, lignin sulfonate salt, formaldehyde condensate of alkyl naphthalene sulfonate, and isobutylene-maleic anhydride copolymer.

When the compounds of the present invention are used as agents for pest control in agriculture, the amount of active ingredient in the formulation is 0.01 to 90 weight % and particularly preferably 0.05 to 85 weight % and wettable powder, emulsion, suspending agents, floable agents, water-soluble powder, granulated wettable powder which are diluted to predetermined concentrations with water, and dusting powder and granules as they are, are applied onto plants or soil.

In addition, when the compounds of the present invention are used as agents for pest control in quarantine purposes, emulsion, wettable powder, floable agents, and the like are applied by diluting to predetermined concentrations with water and oil solution, aerosol, poison bait, anti-acarid sheet, and the like are applied as they are.

When the compounds of the present invention are used as agents for pest control in controlling ectoparasites of livestock such as cattle and pigs or of pets such as dogs and cats, formulations using the compounds of the present invention are used in known methods in the field of veterinary medicine. As such methods, examples thereof include a method for administering in forms such as tablets, capsules, immersion liquid, feedstuff mix, suppository, and injection (intramuscular, subcutaneous, intravenous, intraperitoneal, or the like) when systemic control is required and a method for administering by spraying, pouring-on, or spotting-on oily- or aqueous liquid formulations or a method for mounting objects, which are resin formulations shaped into collars, ear tags, or the like, when non-systemic control is required. In this case, the proportion is normally used where 0.01 to 1000 mg of the compounds of the present invention are applied per 1 kg of host animal.

EXAMPLE

Next, the present invention will be described in further detail by using Examples. However, the present invention is not limited to the Examples below in any aspects.

Production Example 1

Production of 8β-[2-isopropylideneaminooxy-4-(trifluoromethyl)phenoxy]-3-(5-cyano-pyridin-2-yl)-3-azabicyclo[3.2.1]octane (E)

Step 1

Production of 8β-hydroxy-3-(5-cyano-pyridin-2-yl)-3-azabicyclo[3.2.1]octane (A)

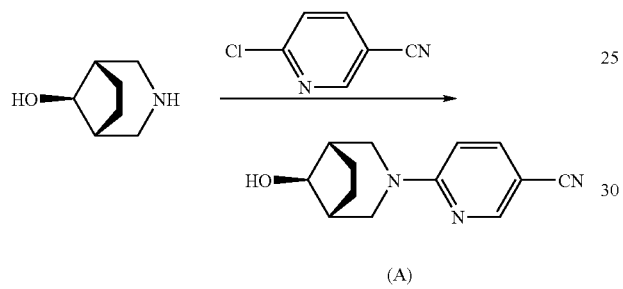

5 ml of acetonitrile suspension containing 0.15 g of 3-azabicyclo[3.2.1]octa-8-ol, 0.65 g of potassium carbonate, and 0.33 g of 2-chloro-5-cyanopyridine was refluxed with heating overnight. After being cooled to room temperature, the mixture was poured into water and extracted with ethyl acetate. Organic layer was washed with saline and dried with anhydrous magnesium sulfate. 0.16 g of a crude compound (A) was obtained by evaporating solvents under reduced pressure and this compound was directly used in the next step.

Step 2

Production of 8β-[2-methoxymethoxy-4-(trifluoromethyl)phenoxy]-3-(5-cyano-pyridine-2-yl)-3-azabicyclo[3.2.1]octane (B)

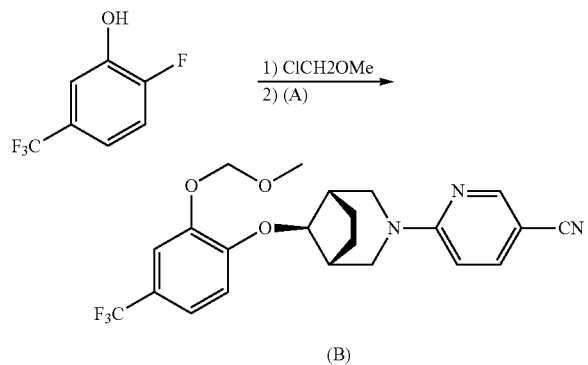

0.14 g of 60% sodium hydride was added to 10 ml of dimethylformamide (DMF) solution containing 0.58 g of 4-fluoro-3-hydroxybenzotrifluoride with ice-cooling. After stirring the mixture for 30 minutes at room temperature, 0.28 g of chloromethyl ether was added dropwise thereto with ice-cooling. After completing the addition, the reaction solution was heated to room temperature and stirred for 30 minutes and then further heated to 80° C. and stirred for 30 minutes. 0.49 g of the compound (A) and 0.13 g of 60% sodium hydride were added to the reaction mixture at 80° C. and the resulting mixture was stirred for 30 minutes and then heated to 80° C. and was further stirred for 2 hours. The reaction mixture was cooled to room temperature, poured into water, and extracted with ethyl acetate. After being washed with water and dried with anhydrous magnesium sulfate, the organic layer was filtered and evaporated under reduces pressure. The concentrate was purified by silica gel column chromatography (eluant: mixed solvent of n-hexane and ethyl acetate) to obtain 0.82 g of the target compound (B).

$^1$H-NMR(CDCl$_3$, δppm):1.55-1.63(m, 2H), 2.02-2.05(m, 2H), 2.60(brs, 2H), 3.13(d, 2H), 3.52(s, 3H), 4.22(d, 2H), 4.63(s, 1H), 5.20(s, 2H), 6.58(d, 1H), 7.03(d, 1H), 7.26(d, 1H), 7.37(s, 1H), 7.62(d, 1H), 8.41(s, 1H)Step 3

Production of 8β-[2-hydroxy-4-(trifluoromethyl)phenoxy]-3-(5-cyano-pyridine-2-yl)-3-azabicyclo[3.2.1]octane (C)

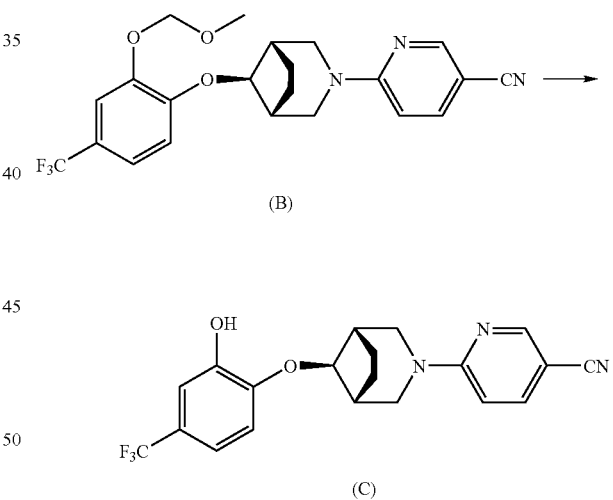

10 ml of 10% hydrochloric acid was added to 10 ml of tetrahydrofuran (THF) solution containing 0.82 g of the compound (B) at room temperature. The mixture was refluxed with heating for 30 minutes, poured into water, and extracted with ethyl acetate. The organic layer was washed with saline and dried with anhydrous magnesium sulfate. 0.74 g of the target compound (C) was obtained by evaporating the solvents under reduced pressure. This compound was directly used in the next step without purification.

$^1$H-NMR(CDCl$_3$, δppm):1.62-1.75(m, 2H), 1.91-1.98(m, 2H), 2.65(brs, 2H), 3.17(d, 2H), 4.26(d, 2H), 4.66(s, 1H), 5.63(s, 1H), 6.60(d, 1H), 6.98(d, 1H), 7.13(d, 1H), 7.16(s, 1H), 7.63(d, 1H), 8.42(s, 1H)

Step 4

Production of 8β-[2-isopropylideneaminooxy-4-(trifluoromethyl)phenoxy]-3-(5-cyano-pyridine-2-yl)-3-azabicyclo[3.2.1]octane (E)

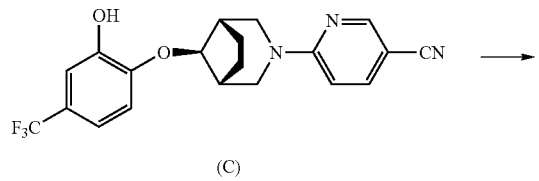

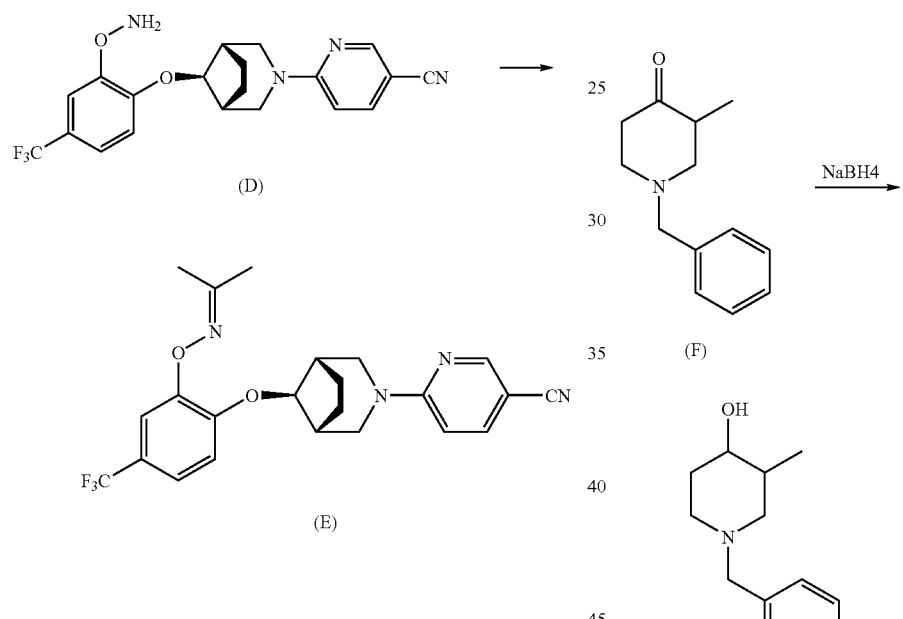

0.76 g of a compound (D) was synthesized by the method described in Japanese Patent Application Laid-Open No. 2001-81071 using 0.74 g of the compound (C).

$^1$H-NMR(CDCl$_3$, δppm):1.55-1.68(m, 2H), 1.99-2.04(m, 2H), 2.59(brs, 2H), 3.13(d, 2H), 4.22(d, 2H), 4.60(s, 1H), 6.00(brs, 2H), 6.59(d, 1H), 6.98(d, 1H), 7.20(d, 1H), 7.60(d, 2H), 8.01(s, 1H), 8.41(s, 1H)

3 ml of acetone and 1 drop of concentrated hydrochloric acid were added to 3 ml of ethanol solution containing 0.76 g of the compound (D) and the entire mixture was stirred for 1 hour at room temperature. The mixture was poured into water and extracted with ethyl acetate. After being washed with water and dried with anhydrous magnesium sulfate, the organic layer was filtered and then vacuum-concentrated. The concentrate was purified by silica gel column chromatography (eluant: mixed solvent of n-hexane and ethyl acetate) to obtain 0.45 g of the target compound (E). Melting temperature: 120-122° C.

Production Example 2

Production of cis-3-methyl-4-[2-propoxy-4-(trifluoromethyl)phenoxy]-1-[6-(trifluoromethyl)-pyridazin-3-yl]piperidine and trans-3-methyl-4-[2-propoxy-4-(trifluoromethyl)phenoxy]-1-[6-(trifluoromethyl)-pyridazin-3-yl]piperidine Step 1

Production of trans-1-benzyl-3-methyl-4-[2-propoxy-4-(trifluoromethyl)phenoxy]piperidine (H$_{trans}$) and cis-1-benzyl-3-methyl-4-[2-propoxy-4-(trifluoromethyl)phenoxy]piperidine (H$_{cis}$)

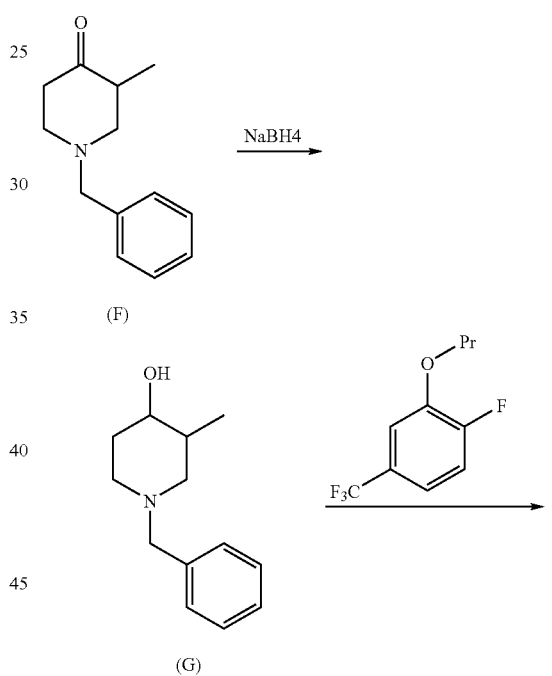

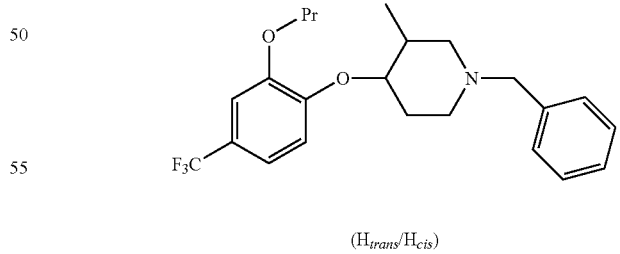

(H$_{trans}$/H$_{cis}$)

0.47 g of sodium borohydride was added to 40 ml of ethanol solution containing 2.53 g of N-benzyl-3-methyl-4-piperidinone (F) with ice-cooling. The mixture was stirred for 2 hours at room temperature and then neutralized with 10% hydrochloric acid with ice-cooling. The resulting mixture was extracted with methylene chloride and the organic layer was dried with anhydrous magnesium sulfate. 2.27 g of a crude compound (G) was obtained by evaporating the solvents under reduced pressure. This compound was directly used in the next reaction.

0.66 g of 4-fluoro-3-propoxybenzotrifluoride was added to 15 ml of DMF containing 1 g of the crude compound (G). The mixture was heated to 80° C. and 0.29 g of 60% sodium hydride was added thereto and the resulting mixture was kept heated for 5 hours at 100° C. The mixture was cooled to room temperature, poured into water, and then extracted with ethyl acetate. After being washed with water and dried with anhydrous magnesium sulfate, the organic layer was filtered and vacuum-concentrated. The concentrate was purified by silica gel column chromatography (eluant: mixed solvent of n-hexane and ethyl acetate) to obtain 0.35 g of a trans isomer ($H_{trans}$) and 0.21 g of a cis isomer ($H_{cis}$) as first and second fractions, respectively.

Step 2

Production of cis-3-methyl-4-[2-propoxy-4-(trifluoromethyl)phenoxy]-1-[6-(trifluoromethyl)-pyridazin-3-yl]piperidine ($J_{cis}$) and trans-3-methyl-4-[2-propoxy-4-(trifluoromethyl)phenoxy]-1-[6-(trifluoromethyl)-pyridazin-3-yl]piperidine ($J_{trans}$)

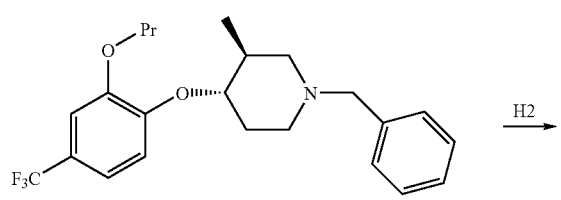

($H_{trans}$)

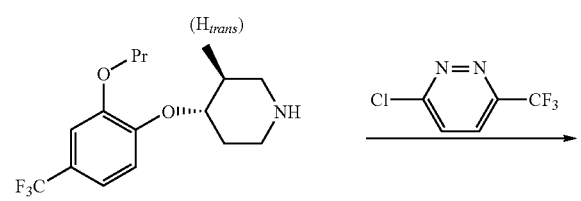

(I)

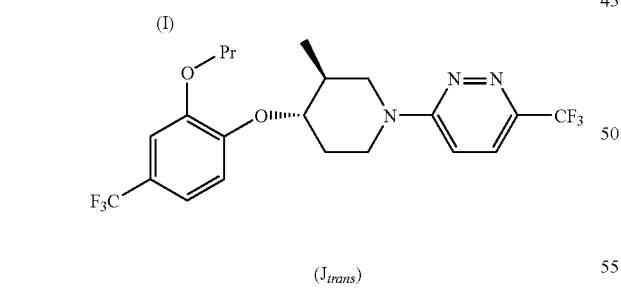

($J_{trans}$)

0.1 g of 20% palladium hydroxide-carbon was added to 4 ml of ethanol solution containing 0.35 g of the trans isomer ($H_{trans}$). This suspension was heated to 60° C. and stirred for 1 day and night under hydrogen atmosphere (hydrogen pressure: $1.01 \times 10^5$ Pa). After cooling the mixture to room temperature, 8 ml of ethanol and 0.1 g of 20% palladium hydroxide-carbon were added thereto. This suspension was heated to 60° C. and stirred for 9 hours under hydrogen atmosphere (hydrogen pressure: $1.01 \times 10^5$ Pa). The mixture was cooled to room temperature and then subjected to celite filtration. 0.22 g of a crude compound (I) was obtained by evaporating the filtrate under reduced pressure. This compound was directly used in the next reaction.

0.14 g of 3-chloro-6-(trifluoromethyl)pyridazine, 0.28 g of potassium carbonate, and 10 mg of tetra-n-butylammonium iodide were added to 2 ml acetonitrile solution containing 0.22 g of the crude compound (I) and the mixture was refluxed with heating for 1 hour at 120° C. The mixture was cooled to room temperature, poured into water, and then extracted with ethyl acetate. After being washed with water, and dried with anhydrous magnesium sulfate, the organic layer was filtered and vacuum-concentrated. The concentrate was purified by silica gel column chromatography (eluant: mixed solvent of n-hexane and ethyl acetate) to obtain 0.2 g of the target compound ($J_{trans}$).

Viscous Oil $^1$H-NMR data of this compound are as follows.

$^1$H-NMR(CDCl$_3$, δppm):1.04(t, 3H), 1.14(d, 3H), 1.77-1.88(m, 3H), 2.11-2.19(m, 2H), 3.20(dd, 1H), 3.45-3.54(m, 1H), 3.98(t, 2H), 4.16-4.31(m, 3H), 6.97(twod's, 1H×2), 7.10 (s, 1H), 7.13(d, 1H), 7.46(d, 1H)

0.16 g of the target compound ($J_{cis}$) was obtained from 0.21 g of the cis isomer ($H_{cis}$) by a similar process. Viscous oil $^1$H-NMR data of this compound are as follows.

$^1$H-NMR(CDCl$_3$, δppm):1.06(t, 3H), 1.11(d, 3H), 1.74-1.91(m, 3H), 2.05-2.13(m, 2H), 3.48(dd, 1H), 3.57-3.66(m, 1H), 3.98(t, 2H), 4.09-4.19(m, 2H), 4.56-4.58(m, 1H), 6.97 (twod's, 1H×2), 7.10(s, 1H), 7.16(d, 1H), 7.46(d, 1H)

Production Example 3

Production of 3α-(5-trifluoromethyl-2-pyridyloxy)-8-(5-trifluoromethyl-pyridine-2-yl)-8-azabicyclo[3.2.1]octane (N)

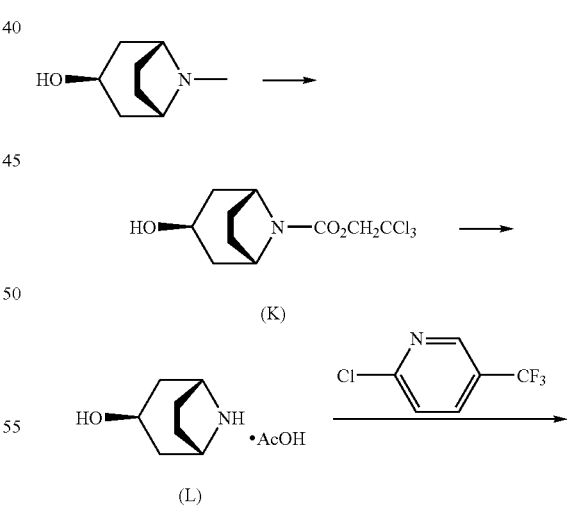

(K)

(L)

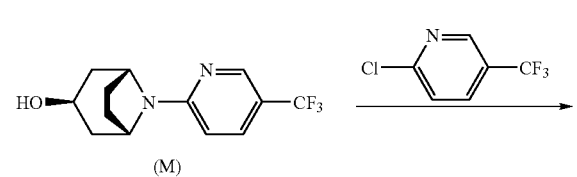

(M)

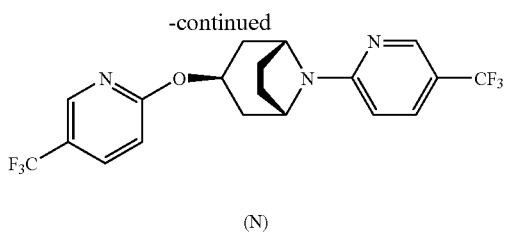

(N)

23.3 g of 2,2,2-trichloroethyl chloroformate ester was added to 150 ml of the benzene suspension containing 14.1 g of tropine and 1.4 g of potassium carbonate at room temperature and the entire mixture was refluxed for 3.5 hours. After being cooled to room temperature, the reaction mixture was poured into water and extracted with ethyl acetate. The organic layer was washed with saline and dried with anhydrous magnesium sulfate. 30.1 g of an oily carbonate (K) was obtained by evaporating the solvents under reduced pressure and this carbonate was used directly in the next reaction.

Next, 65 g of zinc powder was added to 250 ml of the acetate solution of this carbonate (K). After being stirred for 5 minutes, the mixture was heated at 80° C. for 1 hour. After being cooled to room temperature, the mixture was subjected to celite filtration. 15.5 g of a crude product of the compound (L) was obtained by vacuum-concentrating the filtrate.

150 ml of acetonitrile suspension containing 5.64 g of the crude product of the compound (L) obtained as above, 41.5 g of potassium carbonate, and 8.2 g of 2-chloro-5-trifluoromethylpyridine was refluxed for 3.5 hours. After being cooled to room temperature, the reaction mixture was poured into water and extracted with ethyl acetate. The organic layer was washed with saline and dried with anhydrous magnesium sulfate. 3.5 g of the compound (M) was obtained as crystals by evaporating the solvents under reduced pressure.

$^1$H-NMR(CDCl$_3$, δ ppm):1.42(d, 1H), 1.77(d, 2H), 2.05-2.20(m, 4H), 2.32-2.39(m, 2H), 4.09(brs, 1H), 4.53(brs, 2H), 6.52(d, 1H), 7.58(dd, 1H), 8.38(d, 1H)

32 mg of 60% sodium hydride was added to 3 ml of DMF solution containing 0.21 g of the compound (M) with ice-cooling and the entire mixture was stirred for 40 minutes. Subsequently, 0.17 g of 2-chloro-5-trifluoromethylpyridine was added to this mixture and the resulting mixture was heated to 100° C. and was stirred overnight with heating. After cooling to room temperature, the reaction mixture was poured into ice-cold water and extracted with ethyl acetate. After being washed with water and dried with anhydrous magnesium sulfate, the organic layer was filtered and then vacuum-concentrated. The residue was purified by column chromatography (developing solution: mixed solvent of n-hexane and ethyl acetate) to obtain the target compound (N). Melting temperature: 104-105° C.

$^1$H-NMR(CDCl$_3$, δppm):1.25(s, 1H), 1.55(s, 1H), 1.95-2.33(m, 6H), 4.58(brs, 2H), 5.37(t, 1H), 6.55(d, 1H), 6.80(d, 1H), 7.61(dd, 1H), 7.78(dd, 1H), 8.41(s, 2H), Examples of the compounds of the present invention produced by the method according to the above Examples are shown in the Table below including the compounds produced in the above Examples. Note that in the Table below, R$^1$ and R$^2$ show substituents including substituents associated by two or more substituents so that the Table is simplified. Also, the description "vis" shows that the compound is a viscous oil and the description "amor" shows that the compound is amorphous. Moreover, nD21.8-1.5008 means that the refractive index at 21.8° C. is 1.5008 (the same also applies to others). In addition, the description "cPr" means cyclopropyl, the description "cHex" means cyclohexyl (the same also applies to others), the description "Ac" means acetyl, the description "nPr" means normal propyl, the description "iPr" means isopropyl, the description "nBu" means normal butyl, the description "iBu" means isobutyl, and the description "tBu" means tertiary butyl, and the description "TMS" means trimethylsilyl and the description "THF" means tetrahydrofuranyl.

TABLES 1-3

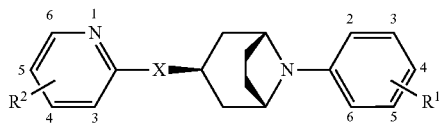

| Compound No. | R$^2$ | X | R$^1$ | Physical constant [ ]: Melting point ° C. |
|---|---|---|---|---|
| 1-1 | 5-CF$_3$ | O | 2-OnPr-4-CF$_3$ | [90-92] |
| 1-2 | 5-CF$_3$ | O | 2-CHO-4-CF$_3$ | [122-123] |
| 1-3 | 5-CF$_3$ | O | 2-CH$_2$OH-4-CF$_3$ | vis |
| 1-4 | 5-CF$_3$ | O | 2-CH$_2$OCH(OMe)Me-4-CF$_3$ | [82-85] |
| 1-5 | 5-CF$_3$ | O | 2-CH$_2$OEt-4-CF$_3$ | vis |
| 1-6 | 5-CF$_3$ | O | 2-Cl-4-CF$_3$ | [92-93] |
| 1-7 | 5-CF$_3$ | O | 2-C(O)OiPr-4-CF$_3$ | vis |
| 1-8 | 5-CF$_3$ | O | 2,6-(NO$_2$)$_2$-4-CF$_3$ | vis |
| 1-9 | 5-CF$_3$ | O | 2-C(O)NHCH(Me)CH$_2$OH-4-CF$_3$ | amor |
| 1-10 | 5-CF$_3$ | O | 2-CH=NOEt-4-CF$_3$ | vis |
| 1-11 | 5-CF$_3$ | O | (E)-2-CH=NOiPr-4-CF$_3$ | [79-80] |
| 1-12 | 5-CF$_3$ | O | 2-CH=NO-propargyl-4-CF$_3$ | [84-86] |
| 1-13 | 5-CF$_3$ | O | 2-(5-Me-oxazoline-2-yl)-4-CF$_3$ | vis |
| 1-14 | 3-Cl-5-CF$_3$ | O | 2-CH$_2$OEt-4-CF$_3$ | vis |
| 1-15 | 5-CF$_3$ | O | 2-OMe-4-CF$_3$ | [127-130] |
| 1-16 | 5-CF$_3$ | O | (Z)-2-CH=NOiPr-4-CF$_3$ | vis |
| 1-17 | 5-CF$_3$ | O | 2-C(O)OEt-4-CF$_3$ | vis |
| 1-18 | 5-CF$_3$ | O | 2-C(O)OtBu-4-CF$_3$ | [95-98] |

TABLES 1-3-continued

| Compound No. | R² | X | R¹ | Physical constant [ ]: Melting point ° C. |
|---|---|---|---|---|
| 1-19 | 3-Cl-5-CF₃ | O | 2-C(O)OiPr-4-CF₃ | vis |
| 1-20 | 5-CF₃ | O | 6-Cl-2-C(O)OiPr-4-CF₃ | vis |
| 1-21 | 5-CF₃ | O | 2-CH=NOMe-4-CF₃ | vis |
| 1-22 | 5-CF₃ | O | 2-CH=NOMe-4-CF₃ | vis |
| 1-23 | 5-CF₃ | O | 2-C(O)OCH₂cPr-4-CF₃ | vis |
| 1-24 | 5-CF₃ | O | 2-C(O)OCH₂CF₃-4-CF₃ | vis |
| 1-25 | 5-CF₃ | O | 2-C(O)OiBu-4-CF₃ | vis |
| 1-26 | 5-CF₃ | O | 2-C(O)OnPr-4-CF₃ | vis |
| 1-27 | 5-CF₃ | O | 2-CH(OH)CH₂CH(Me)₂-4-CF₃ | amor |
| 1-28 | 5-CF₃ | O | 2-C(O)OCH(Me)CH=CH₂-4-CF₃ | vis |
| 1-29 | 5-CF₃ | O | 2-C(O)OcPen-4-CF₃ | vis |
| 1-30 | 5-CF₃ | O | 2-C(O)ON=C(Me)₂-4-CF₃ | vis |
| 1-31 | 5-CF₃ | O | 2-OCH₂cPr-4-CF₃ | [88-90] |
| 1-32 | 5-CF₃ | O | 2-OEt-4-CF₃ | [102-105] |
| 1-33 | 5-CF₃ | O | 2-C(O)OCH₂CHF₂-4-CF₃ | vis |
| 1-34 | 5-CF₃ | O | 2-OnBu-4-CF₃ | [90-92] |
| 1-35 | 5-CF₃ | O | 2-OnPr-4-CN | [107-110] |
| 1-36 | 5-CF₃ | O | 2-C(O)OCH₂OMe-4-CF₃ | vis |
| 1-37 | 5-CF₃ | O | 2-C(O)OCH₂tBu-4-CF₃ | [100-102] |
| 1-38 | 5-CF₃ | O | 2-C(O)N(Me)₂-4-CF₃ | vis |
| 1-39 | 5-CF₃ | O | 2-C(O)OCH(Me)CH(Me)₂-4-CF₃ | vis |
| 1-40 | 5-CF₃ | O | 2-C(O)OCH(Et)₂-4-CF₃ | vis |
| 1-41 | 5-CF₃ | O | 2-C(O)O(THF-3-yl)-4-CF₃ | vis |
| 1-42 | 5-CF₃ | NH | 2-C(O)OiPr-4-CF₃ | vis |
| 1-43 | 5-CF₃ | O | 2-C(O)O(CH₂)₂OMe-4-CF₃ | vis |
| 1-44 | 5-CF₃ | O | 2-C(O)OCH(Me)CH₂OMe-4-CF₃ | vis |
| 1-45 | 5-CF₃ | O | 2-C(O)OCH(CN)Me-4-CF₃ | vis |
| 1-46 | 5-CF₃ | O | 2-C(O)OCH(Cl)Et-4-CF₃ | vis |
| 1-47 | 5-CF₃ | O | 2-C(O)SiPr-4-CF₃ | vis |
| 1-48 | 5-CF₃ | O | 2-OBn-4-CF₃ | [98-102] |
| 1-49 | 5-CF₃ | O | 2-OH-4-CF₃ | [130-131] |
| 1-50 | 5-CF₃ | O | 2-OCH₂CH(Me)OMe-4-CF₃ | [116-120] |
| 1-51 | 5-CN | O | 2-C(O)OiPr-4-CF₃ | [124-126] |
| 1-52 | 5-CF₃ | O | 2-CH(OTMS)CH₂CN-4-CF₃ | [131-133] |
| 1-53 | 5-CF₃ | O | 2-CH(OH)CH₂CN-4-CF₃ | [24-25] |
| 1-54 | 5-CN | O | 2-OnPr-4-CF₃ | [141-142] |
| 1-55 | 5-CF₃ | O | 2-OCH₂cPr-4-C₃F₇ | nD22.2-1.4942 |
| 1-56 | 3-Me | O | 4-Ph | |
| 1-57 | 3-F | O | 3,4,5,6-F₄ | |
| 1-58 | 5-CN | S | 2-CN | |
| 1-59 | 5-NO₂ | S | 3-CF₃ | |
| 1-60 | 5-CHO | S | 4-iPr | |
| 1-61 | 4-OMe | S | 3,5-Me₂ | |
| 1-62 | 4-cPr | S | 3-NO₂ | |
| 1-63 | 5-OcHex | SO₂ | 3-Br | |
| 1-64 | 3-CH₂CH₂cPr | SO₂ | 3-cPr | |
| 1-65 | 4-OCH₂cPr | SO₂ | 4-OcPr | |
| 1-66 | 4-OCH=CH₂ | SO₂ | 2-CH₂cPr | |
| 1-67 | 5-OCF₃ | SO₂ | 2-OCH₂cPr | |
| 1-68 | 4-OCH=CHCH₂CF₃ | NH | 4-OCH=CH₂ | |
| 1-69 | 4-CO₂Et | NH | 2-OCH₂Cl | |
| 1-70 | 6-F | NH | 2-OCH=CBr₂ | |
| 1-71 | 6-CN | NMe | 3-NO₂ | |
| 1-72 | 6-NO₂ | NAc | 4-OCF₃ | |
| 1-73 | 6-OcPr | NMe | 4-CN | |

TABLE 4

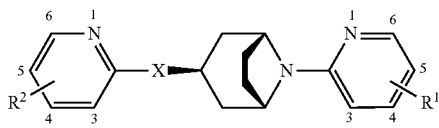

| Compound No. | R² | X | R¹ | Physical constant [ ]: Melting point °C. |
|---|---|---|---|---|
| 2-1 | 5-CF₃ | O | 4-CF₃-6-Cl | nD22.1-1.5134 |
| 2-2 | 4-CF₃-6-Cl | O | 5-CF₃ | vis |
| 2-3 | 5-CF₃ | O | 5-CF₃ | [104-105] |
| 2-4 | 5-CF₃-6-OnPr | O | 5-CF₃ | [90-93] |
| 2-5 | 5-CF₃ | S | 4-cPr | |
| 2-6 | 3-Me | S | 3-OcPr | |
| 2-7 | 3-F | S | 3,5-Me₂ | |
| 2-8 | 5-CN | S | 4-CF₃ | |
| 2-9 | 5-NO₂ | SO₂ | 5-CO₂Et | |
| 2-10 | 5-CHO | SO₂ | 4-CH=CF₂ | |
| 2-11 | 4-OMe | SO₂ | 5-CH=Cme₂ | |
| 2-12 | 4-cPr | SO₂ | 3-OCH₂CH₂cPr | |
| 2-13 | 5-OcHex | NH | 4-CH₂cPr | |
| 2-14 | 3-CH₂CH₂cPr | NH | 3-Oet-4-cPr | |
| 2-15 | 4-OCH₂cPr | Nme | 4-CHO | |
| 2-16 | 6-Me | Nme | 5-NO₂ | |

TABLE 5

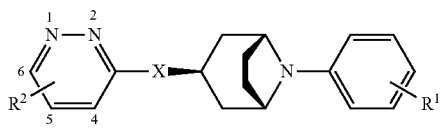

| Compound No. | R² | X | R¹ | Physical constant [ ]: Melting point °C. |
|---|---|---|---|---|
| 3-1 | 6-CF₃ | O | 2-C(O)OiPr-4-CF₃ | [154-157] |
| 3-2 | 6-CF₃ | O | 2-CH₂OEt-5-CF₃ | nD22.2-1.4996 |
| 3-3 | 4-CF₃ | O | 2-Me | |
| 3-4 | 5-CF₃ | O | 3-Cl | |
| 3-5 | 4-Br | S | 4-CF₃ | |
| 3-6 | 5-Me | S | 3-NO₂ | |
| 3-7 | 6-CF₃ | S | 3-CO₂Me | |
| 3-8 | 6-CF₃ | SO₂ | 4-tBu | |
| 3-9 | 4-cPr | SO₂ | 3-cPr | |
| 3-10 | 6-CF₃ | NH | 4-OcHex | |
| 3-11 | 6-OCH₂CH₂cPr | NH | 4-Nme₂ | |
| 3-12 | 5-CH=Cme₂ | NH | 3-iPr | |
| 3-13 | 6-CF₃ | Nme | 4-OCF₃ | |
| 3-14 | 4-NO₂ | Nme | 2-CN | |
| 3-15 | 5-CHO | Nac | 4-CHO | |

TABLES 6-9

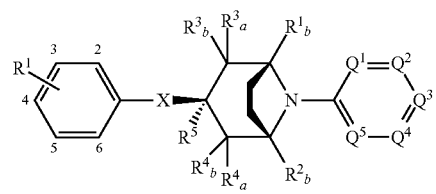

| Compound No. | R¹ | Q¹ | Q² | Q³ | Q⁴ | Q⁵ | X | Physical constant [ ]: Melting point °C. | Remark |
|---|---|---|---|---|---|---|---|---|---|
| 4-1 | 2-OnPr-4-CF₃ | N | N | C—CF₃ | CH | CH | O | [197-199] | |
| 4-2 | 2-OnPr-4-CF₃ | N | CH | C—Me | CH | N | O | [175-176] | |
| 4-3 | 2-OnPr-4-CF₃ | N | C—Cl | N | CH | C—Me | O | [128-132] | |
| 4-4 | 2-OnPr-4-CF₃ | N | C—Cl | C—Me | CH | N | O | [83-189] | |
| 4-5 | 2-OnPr-4-CF₃ | N | CH | C—CF₃ | CH | N | O | [152-155] | |
| 4-6 | 2-OnPr-4-CF₃ | N | N | C—CF₃ | CH | CH | O | amor | R³ᵦ = R⁵ᵦ = Me |
| 4-7 | 2-OCH₂CH(Me)OMe-4-CF₃ | N | N | C—CF₃ | CH | CH | O | [181-185] | |
| 4-8 | 2-OCH₂cPr-4-CF₃ | N | N | C—CN | CH | CH | O | [213-215] | |
| 4-9 | 2-OCH₂cPr-4-CF₃ | N | N | C—CF₃ | CH | CH | O | [204-206] | |
| 4-10 | 2-CO₂iPr-4-CF₃ | N | N | C—CN | CH | CH | O | [219-221] | |
| 4-11 | 2-OnBu-4-CF₃ | N | N | C—CF₃ | CH | CH | O | [197-199] | |
| 4-12 | 2-OiBu-4-CF₃ | N | N | C—CF₃ | CH | CH | O | [223-224] | |
| 4-13 | 2-Oet-4-CF₃ | N | N | C—CF₃ | CH | CH | O | [192-194] | |
| 4-14 | 2-CO₂iPr-4-CF₃ | N | N | C—CF₃ | CH | CH | O | [201-203] | |
| 4-15 | 2-OCH₂CH(F)Me-4-CF₃ | N | N | C—CN | CH | CH | O | [214-218] | |
| 4-16 | 2-OCH₂CH(F)Me-4-CF₃ | N | N | C—CF₃ | CH | CH | O | [197-200] | |
| 4-17 | 2-OCH₂cPr-4-CF₃ | CH | N | C—Cl | CH | CH | O | [148-150] | |
| 4-18 | 2-OCH₂cPr-4-CF₃ | CH | N | C—CN | CH | CH | O | [126-128] | |
| 4-19 | 2-OnPr-4-CF₃ | N | N | C—CF₃ | CH | CH | O | [214-216] | sulfate |
| 4-20 | 2-OnPr-4-CF₃ | N | N | C—CF₃ | CH | CH | O | [220up] | borate |
| 4-21 | 4-CF₃ | N | N | C—CF₃ | CH | CH | O | [187-188] | |
| 4-22 | 2-OnPr-4-CF₃ | CH | N | C—Cl | CH | CH | O | [149-150] | |
| 4-23 | 4-CF₃ | C—OnPr | N | C—CF₃ | CH | CH | O | nD21.9-1.5132 vis | |
| 4-24 | 2-CH₂Oet-4-CF₃ | N | N | C—CF₃ | CH | CH | O | | |
| 4-25 | 4-CF₃ | CH | CH | N | CH | CH | O | | |
| 4-26 | 2,6-Me₂ | CH | CH | Cme | N | CBr | CH | O | |
| 4-27 | 4-Ome | N | N | Cme | CH | CH | S | | |
| 4-28 | 3-NO₂ | N | N | C—CF₃ | CH | CH | S | | |
| 4-29 | 2-F | N | N | C—CF₃ | CH | CH | S | | |
| 4-30 | 3-CHO | N | N | C—CN | CH | CH | S | | |

TABLES 6-9-continued

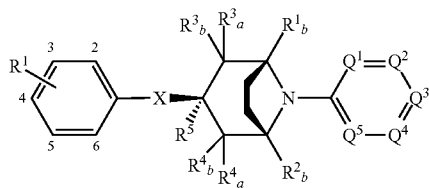

| Compound No. | R¹ | Q¹ | Q² | Q³ | Q⁴ | Q⁵ | X | Physical constant [ ]: Melting point °C. Remark |
|---|---|---|---|---|---|---|---|---|
| 4-31 | 3-OiPr | N | N | C—CF₃ | CH | CH | S | |
| 4-32 | 4-Me | CH | N | C—Cl | CH | CH | S | |
| 4-33 | 4-cPr | CH | N | C—CN | CH | CH | S | |
| 4-34 | 3-OcPr | N | N | C—CF₃ | CH | CH | S | |
| 4-35 | 4-CH₂cPr | N | N | C—CF₃ | CH | CH | SO₂ | |
| 4-36 | 2-OCH₂CH₂cPr | N | N | C—CF₃ | CH | CH | SO₂ | |
| 4-37 | 3-OCH=Cme₂ | N | N | C—CF₃ | CH | CH | SO₂ | |
| 4-38 | 4-OCF₃ | N | N | C—CF₃ | CH | CH | SO₂ | |
| 4-39 | 4-OCF₃ | N | N | C—CN | CH | CH | SO₂ | |
| 4-40 | 3-CO₂Me | N | N | C—CF₃ | CH | CH | SO₂ | |
| 4-41 | 3-Me | CH | N | C—Cl | CH | CH | NH | |
| 4-42 | 4-tBu | CH | N | C—CN | CH | CH | NH | |
| 4-43 | 2-CH=CHMe | N | N | C—CF₃ | CH | CH | NH | |
| 4-44 | 2-OCH₂cPr-4-CF₃ | N | N | C—CF₃ | CH | CH | NH | |
| 4-45 | 2-OCH₂cPr-4-CF₃ | N | N | C—CF₃ | CH | CH | NH | |
| 4-46 | 2-CO₂iPr-4-CF₃ | N | N | C—CN | CH | CH | NH | |
| 4-47 | 2-OnBu-4-CF₃ | N | N | C—CF₃ | CH | CH | Nme | |
| 4-48 | 2-OiBu-4-CF₃ | CH | N | C—Cl | CH | CH | Net | |
| 4-49 | 2-Oet-4-CF₃ | CH | N | C—CN | CH | CH | Nac | |
| 4-50 | 2-CO₂iPr-4-CF₃ | N | N | C—CF₃ | CH | CH | Nac | |
| 4-51 | 2-OnPr-4-CF₃ | N | CH | C—CN | CH | CH | O | [124-125] |
| 4-52 | 2-OCH₂cPr-4-CF₃ | N | CH | C—CN | CH | CH | O | [129-131] |
| 4-53 | 2-OCH₂CHFMe-4-CF₃ | N | CH | C—CN | CH | CH | O | [105-109] |
| 4-54 | 2-OCH₂CH₂Ome-4-CF₃ | N | CH | C—CN | CH | CH | O | nD24.7-1.5697 |
| 4-55 | 2-CO₂iPr-4-CF₃ | N | CH | C—CN | CH | CH | O | [133-135] |
| 4-56 | 2-OCH₂iPr-4-CF₃ | N | CH | C—CN | CH | CH | O | [139-141] |
| 4-57 | 2-OCH₂C(Me)=CH₂-4-CF₃ | N | CH | C—CN | CH | CH | O | [90-93] |
| 4-58 | 2-OCH₂CH(Me)Ome-4-CF₃ | N | CH | C—CN | CH | CH | O | [114-118] |
| 4-59 | 2-ON=C(Me)₂-4-CF₃ | N | CH | C—CN | CH | CH | O | [125-128] |
| 4-60 | 2-OnPr-4-OCF₃ | N | CH | C—CF₃ | CH | CH | NH | [89-90] |
| 4-61 | 2-Ome-4-OCF₃ | N | CH | C—CF₃ | CH | CH | NH | [114-116] |
| 4-62 | 2-OnPr-4-CF₃ | N | CH | C—CF₃ | CH | CH | NH | [96-97] |
| 4-63 | 2-Me-3-CF₃ | N | CH | C—CF₃ | CH | CH | NH | [124-125] |
| 4-64 | 2-OnPr-4-CF₃ | CH | CH | C—CF₃ | CH | CH | O | vis |
| 4-65 | 2-OnPr-4-CF₃ | C—Cl | CH | C—CF₃ | CH | CH | O | [104-105] |
| 4-66 | 2-OnPr-4-CF₃ | C—NO₂ | CH | C—CF₃ | CH | CH | O | vis |
| 4-67 | 2-OnPr-4-CF₃ | C—F | CH | C—CF₃ | CH | CH | O | vis |
| 4-68 | 2-OnPr-4-CF₃ | C—N(SO₂Me)₂ | CH | C—CF₃ | CH | CH | O | amor |
| 4-69 | 2-OnPr-4-CF₃ | CH | CH | C—Ome | CH | CH | O | [119-120] |
| 4-70 | 2-OnPr-4-CF₃ | CH | C—F | C—CF₃ | CH | CH | O | vis |
| 4-71 | 2-OnPr-4-CF₃ | CH | CH | C—OCF₃ | CH | CH | O | vis |
| 4-72 | 2-OnPr-4-CF₃ | CH | CH | C—NO₂ | CH | CH | O | [114-117] |
| 4-73 | 2-OnPr-4-CF₃ | CH | CH | C—NH₂ | CH | CH | O | vis |
| 4-74 | 2-OnPr-4-CF₃ | CH | CH | C—NHSO₂CF₃ | CH | CH | O | [90-95] |
| 4-75 | 2-OnPr-4-CF₃ | CH | CH | C—Br | CH | CH | O | vis |
| 4-76 | 2-OnPr-4-CF₃ | CH | C—Cl | C—Cl | CH | CH | O | vis |
| 4-77 | 2-OnPr-4-CF₃ | CH | CH | C-tBu | CH | CH | O | [139-141] |
| 4-78 | 2-OnPr-4-CF₃ | CH | CH | C—Ph | CH | CH | O | [40-50] |
| 4-79 | 2-OnPr-4-CF₃ | CH | C—Oet | C—CF₃ | CH | CH | O | vis |
| 4-80 | 2-OnPr-4-CF₃ | CH | C-nPr | C—CF₃ | CH | CH | O | nD20.4-1.4827 |
| 4-81 | 2-OnPr-4-CF₃ | CH | C—C=NOEt | C—CF₃ | CH | CH | O | [103-105] |
| 4-82 | 2-OnPr-4-CF₃ | CH | C—CO₂iPr | C—CF₃ | CH | CH | O | vis |

Note that $R^1_b$, $R^2_b$, $R^3_a$, $R^3_b$, $R^4_a$, $R^4_b$, and $R^5$ represent hydrogen atom, respectively, unless otherwise indicated.

TABLES 10-11

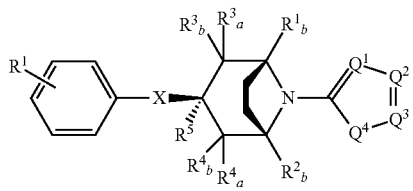

| Compound No. | R$^1$ | Q$^1$ | Q$^2$ | Q$^3$ | Q$^4$ | X | Physical constant [ ]: Melting point ° C. |
|---|---|---|---|---|---|---|---|
| 5-1 | 2-OnPr-4-CF$_3$ | N | N | C—CF$_3$ | S | O | [93-95] |
| 5-2 | 2-OCH$_2$cPr-4-CF$_3$ | N | N | C—CF$_3$ | S | O | [110-112] |
| 5-3 | 2-CO$_2$iPr-4-CF$_3$ | N | N | C—CF$_3$ | S | O | [112-114] |
| 5-4 | 2-ON=C(Me)$_2$-4-CF$_3$ | N | N | C—CF$_3$ | S | O | [121-124] |
| 5-5 | 2-OiBu-4-CF$_3$ | N | N | C—CF$_3$ | S | O | [147-150] |
| 5-6 | 2-OCH$_2$C(Me)=CH$_2$-4-CF$_3$ | N | N | C—CF$_3$ | S | O | [121-124] |
| 5-7 | 2-OCH$_2$CH(Me)OMe-4-CF$_3$ | N | N | C—CF$_3$ | S | O | [98-102] |
| 5-8 | 2-OCH$_2$CH(F)Me-4-CF$_3$ | N | N | C—CF$_3$ | S | O | [105-108] |
| 5-9 | 2-OnPr-4-CF$_3$ | C—CN | C—CF$_3$ | N | N—Me | O | [91-92] |
| 5-10 | 2-OnPr-4-CF$_3$ | C—C(O)NH$_2$ | C—CF$_3$ | N | N—Me | O | [180-181] |
| 5-11 | 4-CF$_3$ | CH | CH | CH | O | S | |
| 5-12 | 2-CF$_3$-3-Cl | N | CH | Cme | O | S | |
| 5-13 | 4-CF$_3$ | CH | N | CH | O | S | |
| 5-14 | 4-CF$_3$-2-OnPr | N | N | CH | O | S | |
| 5-15 | 3-CF$_3$ | N | N | CH | O | S | |
| 5-16 | 3-Me | O | CH | CH | NH | SO$_2$ | |
| 5-17 | 3-F | CH | CH | CH | NH | SO$_2$ | |
| 5-18 | 2-CN | CH | O | CH | NH | SO$_2$ | |
| 5-19 | 3-NO$_2$ | N | CH | C—CF$_3$ | NH | SO$_2$ | |
| 5-20 | 4-CHO | N | CH | CH | NH | SO$_2$ | |
| 5-21 | 4-Ome | CH | CH | CH | S | SO$_2$ | |
| 5-22 | 4-cPr | N | CH | CH | S | SO$_2$ | |
| 5-23 | 2-OcHex | N | CH | CH | S | NH | |
| 5-24 | 3-CH$_2$CH$_2$cPr | N | CH | CH | S | NH | |
| 5-25 | 4-OCH$_2$cPr | N | CH | CH | S | NH | |
| 5-26 | 2-CHO | N | CH | CH | O | NH | |
| 5-27 | 3-OCH=CHMe | N | Cme | CH | O | Nme | |
| 5-28 | 2-CO$_2$Et | CH | CH | CH | O | Nme | |

Note that R$^1_b$, R$^2_b$, R$^3_a$, R$^3_b$, R$^4_a$, R$^4_b$, and R$^5$ represent hydrogen atom, respectively, unless otherwise indicated.

TABLE 12

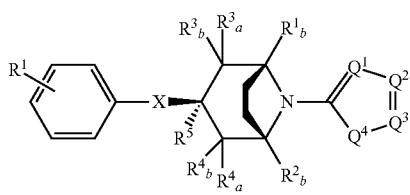

| Compound No. | R$^1$ | Q$^1$ | Q$^2$ | Q$^3$ | Q$^4$ | X | Physical constant [ ]: Melting point ° C. |
|---|---|---|---|---|---|---|---|
| 6-1 | 2-OnPr-4-CF$_3$ | N | NH | C—CF$_3$ | C | O | vis |
| 6-2 | 2-OnPr-4-CF$_3$ | N | NMe | C—CF$_3$ | S | O | |
| 6-3 | 2-OCH$_2$cPr-4-CF$_3$ | N | NH | C—CF$_3$ | S | O | |
| 6-4 | 2-CO$_2$iPr-4-CF$_3$ | N | NH | C—CF$_3$ | S | S | |
| 6-5 | 2-ON=C(Me)$_2$-4-CF$_3$ | N | NH | C—CF$_3$ | S | S | |
| 6-6 | 2-OiBu-4-CF$_3$ | N | Net | C—CF$_3$ | S | SO$_2$ | |
| 6-7 | 2-OCH$_2$C(Me)=CH$_2$-4-CF$_3$ | N | Nac | C—CF$_3$ | S | Nac | |
| 6-8 | 2-OCH$_2$CH(Me)Ome-4-CF$_3$ | N | NH | C—CF$_3$ | S | NH | |
| 6-9 | 2-OCH$_2$CH(F)Me-4-CF$_3$ | N | NH | C—CF$_3$ | S | NH | |
| 6-10 | 2-OnPr-4-CF$_3$ | C—CN | CH—CF$_3$ | N | N—Me | O | |
| 6-11 | 2-OnPr-4-CF$_3$ | C—C(O)NH$_2$ | Cme$_2$ | N | N—Me | O | |

Note that R$^1_b$, R$^2_b$, R$^3_a$, R$^3_b$, R$^4_a$, R$^4_b$, and R$^5$ represent hydrogen atom, respectively, unless otherwise indicated.

TABLES 13-14

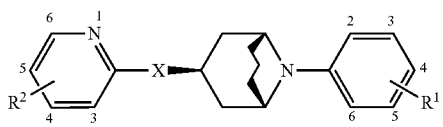

| Compound No. | R² | X | R¹ | Physical constant [ ]: Melting point ° C. |
|---|---|---|---|---|
| 7-1 | 5-CF₃ | O | 2-OnPr-4-CF₃ | amor |
| 7-2 | 5-CF₃ | O | 2-CHO-4-CF₃ | nD22.2-1.5330 |
| 7-3 | 5-CF₃ | O | 2-CH₂OH-4-CF₃ | nD22.3-1.5194 |
| 7-4 | 5-CF₃ | O | 2-CH₂OEt-4-CF₃ | nD22.3-1.5003 |
| 7-5 | 3-Me | O | 2-OnPr-4-CF₃ | |
| 7-6 | 4-Ph | O | 4-CF₃ | |
| 7-7 | 3-OnPr | O | 2-CF₃-3-Cl | |
| 7-8 | 3-OCH₂cPr | O | 4-CF₃ | |
| 7-9 | 4-tBu | O | 4-CF₃-2-OnPr | |
| 7-10 | 4-OCH₂CHFMe | O | 3-CF₃ | |
| 7-11 | — | S | 3-Me | |
| 7-12 | 3-Br | S | 3-F | |
| 7-13 | 4-CO₂tBu | S | 2-CN | |
| 7-14 | 3-CO₂Et | S | 3-NO₂ | |
| 7-15 | 2-OCF=CH₂ | S | 4-CHO | |
| 7-16 | 5-OCH=CHMe | S | 4-Ome | |
| 7-17 | 3-OCH₂cPr | SO₂ | 4-cPr | |
| 7-18 | 4-CH₂CH₂cPr | SO₂ | 2-OcHex | |
| 7-19 | 3-OcPr | SO₂ | 3-CH₂CH₂cPr | |
| 7-20 | 4-cPr | NH | 4-OCH₂cPr | |
| 7-21 | 5-OCF₃ | NH | 2-OnPr-4-CF₃ | |
| 7-22 | 3,5-Me₂ | NH | 4-CF₃ | |
| 7-23 | 6-Cl | NH | 2-CF₃-3-Cl | |
| 7-24 | 5-NO₂ | Nme | 4-CF₃ | |
| 7-25 | 4-CHO | Nac | 4-CF₃-2-OnPr | |

TABLES 15-16

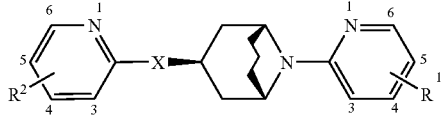

| Compound No. | R² | X | R¹ | Physical constant [ ]: Melting point ° C. |
|---|---|---|---|---|
| 8-1 | 5-CF₃ | O | 5-CF₃ | nD22.7-1.5174 |
| 8-2 | 5-CF₃ | O | 3-Cl-5-CF₃ | nD23.0-1.5266 |
| 8-3 | 3-Me | O | 5-CF₃ | |
| 8-4 | 3-F | O | 4-cPr | |
| 8-5 | 5-CN | S | 3-OcPr | |
| 8-6 | 5-NO₂ | S | 3,5-Me₂ | |
| 8-7 | 5-CHO | S | 4-CF₃ | |
| 8-8 | 4-OMe | S | 5-CO₂Et | |
| 8-9 | 4-cPr | S | 4-CH=CF₂ | |
| 8-10 | 5-OcHex | SO₂ | 5-CH=Cme₂ | |
| 8-11 | 3-CH₂CH₂cPr | SO₂ | 3-OCH₂CH₂cPr | |
| 8-12 | 4-OCH₂cPr | SO₂ | 4-CH₂cPr | |
| 8-13 | 4-OCH=CH₂ | SO₂ | 3-Oet-4-cPr | |
| 8-14 | 5-OCF₃ | SO₂ | 4-CHO | |
| 8-15 | 4-OCH=CHCH₂CF₃ | NH | 5-NO₂ | |
| 8-16 | 4-CO₂Et | NH | 5-CF₃ | |
| 8-17 | 6-F | NH | 4-cPr | |
| 8-18 | 6-CN | Nme | 4-CO₂Et | |
| 8-19 | 6-NO₂ | Nac | 3-Me | |
| 8-20 | 6-OcPr | Nme | 5-OCF₃ | |
| 8-21 | 3-Me | O | 4-Ome | |
| 8-22 | 3-F | O | 5-Cl | |
| 8-23 | 4-OCH=CF₂ | S | 3-nBu | |

TABLES 17-18

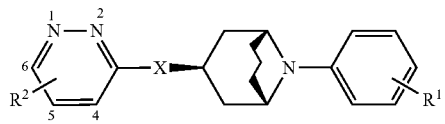

| Compound No. | R² | X | R¹ | Physical constant [ ]: Melting point ° C. |
|---|---|---|---|---|
| 9-1 | 6-CF₃ | O | 2-OnPr-4-CF₃ | vis |
| 9-2 | 6-CF₃ | O | 4-CF₃ | nD22.3-1.5245 |
| 9-3 | 5-Me | O | 2-CH₂OEt-4-CF₃ | |
| 9-4 | 6-CF₃ | O | 2-Cl-4-CF₃ | |
| 9-5 | 6-CF₃ | O | 2-C(O)OiPr-4-CF₃ | |
| 9-6 | 4-cPr | O | 2,6-(NO₂)₂-4-CF₃ | |
| 9-7 | 6-CF₃ | S | 2-C(O)NHCH(Me)CH₂OH-4-CF₃ | |
| 9-8 | 6-OCH₂CH₂cPr | S | 2-CH=NOEt-4-CF₃ | |
| 9-9 | 5-OCH=Cme₂ | S | (E)-2-CH=NoiPr-4-CF₃ | |
| 9-10 | 6-CF₃ | S | 2-CH=NO-propargyl-4-CF₃ | |
| 9-11 | 4-NO₂ | S | 2-(5-Me-oxazoline-2-yl)-4-CF₃ | |
| 9-12 | 5-CHO | S | 2-CH₂Oet-4-CF₃ | |
| 9-13 | 5-Me | SO₂ | 2-Ome-4-CF₃ | |
| 9-14 | 6-CF₃ | SO₂ | (Z)-2-CH=NoiPr-4-CF₃ | |
| 9-15 | 6-CF₃ | SO₂ | 2-C(O)Oet-4-CF₃ | |
| 9-16 | 4-CN | SO₂ | 2-C(O)OtBu-4-CF₃ | |
| 9-17 | 5-Br | NH | 2-C(O)OiPr-4-CF₃ | |
| 9-18 | 4-OcPr | NH | 6-Cl-2-C(O)OiPr-4-CF₃ | |
| 9-19 | 5-OtBu | NH | 3-Br | |
| 9-20 | 5-OCH=CHMe | NH | 4-Me | |
| 9-21 | 4-OCH=CHF | Nme | — | |
| 9-22 | 6-CO₂Me | Nac | 2-Cl | |

TABLES 19-20

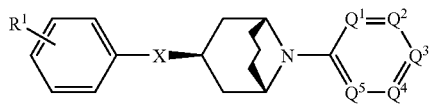

| Compound No. | R¹ | Q¹ | Q² | Q³ | Q⁴ | Q⁵ | X | Physical constant [ ]: Melting point ° C. |
|---|---|---|---|---|---|---|---|---|
| 10-1 | 2-OnPr-4-CF₃ | N | N | C—CF₃ | CH | CH | O | [116-117] |
| 10-2 | 2-OCH₂cPr-4-CF₃ | N | N | C—CF₃ | CH | CH | O | [112-113] |
| 10-3 | 2-OiBu-4-CF₃ | N | N | C—CF₃ | CH | CH | O | [148-149] |
| 10-4 | 2-CH₂OEt-4-CF₃ | N | N | C—CF₃ | CH | CH | O | nD22.1-1.5088 |
| 10-5 | 4-CF₃ | N | N | C—CF₃ | CH | CH | O | [130-131] |
| 10-6 | 2-OCH₂CH(F)Me-4-CF₃ | N | CH | CH | N | C—Me | O | |
| 10-7 | 2-OnPr-4-CF₃ | N | CH | CH | N | CH | O | |
| 10-8 | 2-OnPr-4-CF₃ | N | CH | C—CF₃ | N | CH | S | |
| 10-9 | 4-CF₃ | N | C—Br | CH | N | CH | S | |
| 10-10 | 2-CF₃-3-Cl | N | CH | CH | CH | N | S | |
| 10-11 | 4-CF₃ | N | CH | C—CN | CH | CH | S | |
| 10-12 | 4-CF₃-2-OnPr | N | C—CN | CH | CH | CH | S | |
| 10-13 | 3-CF₃ | N | CH | N | C—CF₃ | C—CF₃ | S | |
| 10-14 | 3-Me | CH | N | C—CN | CH | CH | S | |
| 10-15 | 3-F | N | CH | CH | CH | N | SO₂ | |
| 10-16 | 2-CN | C—Me | N | CH | CH | CH | SO₂ | |
| 10-17 | 3-NO₂ | N | C—F | CH | CH | N | NH | |
| 10-18 | 4-CHO | N | C—Cl | CH | CH | N | NH | |
| 10-19 | 4-Ome | N | CH | N | CH | CH | NH | |
| 10-20 | 4-cPr | CH | C—Me | N | C—Me | CH | NiPr | |
| 10-21 | 2-OcHex | CH | CH | N | CH | CH | Nme | |
| 10-22 | 3-CH₂CH₂cPr | CH | CH | N | CH | CH | Nme | |

TABLE 21

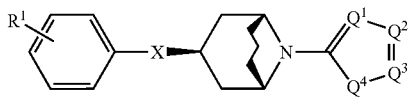

| Compound No. | R¹ | Q¹ | Q² | Q³ | Q⁴ | X | Physical constant [ ]: Melting point ° C. | Remark |
|---|---|---|---|---|---|---|---|---|
| 11-1 | 2-OnPr-4-CF₃ | N | N | C—CF₃ | S | O | | vis |
| 11-2 | 3-F | CH | CH | CH | S | O | | |
| 11-3 | 2-CN | CH | CH | CH | O | O | | |
| 11-4 | 3-NO₂ | N | CH | C—Me | S | S | | |
| 11-5 | 4-CHO | N | C—F | CH | O | S | | |
| 11-6 | 4-OMe | N | N | CH | NH | S | | |
| 11-7 | 4-cPr | N | CH | CH | CH | SO₂ | | |
| 11-8 | 2-OcHex | N | CH | CH | Nme | SO₂ | | |
| 11-9 | 3-CH₂CH₂cPr | N | N | CH | S | NH | | |
| 11-10 | 4-OCH₂cPr | N | CH | CH | NH | NH | | |
| 11-11 | 2-CHO | CH | N | CH | NH | Nme | | |

TABLE 22

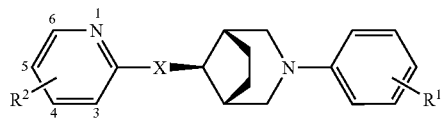

| Compound No. | Q | X | R¹ | Physical constant [ ]: Melting point ° C. |
|---|---|---|---|---|
| 12-1 | 5-CF₃ | O | 2-NO₂-4-CF₃ | [92-94] |
| 12-2 | 5-CF₃ | O | 2-NH₂-4-CF₃ | [120-122] |
| 12-3 | 5-CF₃ | O | 2-NHAc-4-CF₃ | [145-147] |
| 12-4 | 5-CF₃ | O | 2-OnPr-4-CF₃ | [104-106] |

TABLE 22-continued

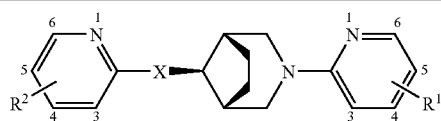

| Compound No. | Q | X | R¹ | Physical constant [ ]: Melting point ° C. |
|---|---|---|---|---|
| 12-5 | 5-CF₃ | O | 2-C(O)OiPr-4-CF₃ | nD21.8-1.5008 |
| 12-6 | 3-Cl | O | 2-CH=NOEt-4-CF₃ | |
| 12-7 | 4-CHO | O | (E)-2-CH=NOiPr-4-CF₃ | |
| 12-8 | 6-NO₂ | S | 2-CH=NO-propargyl-4-CF₃ | |
| 12-9 | 4-OCH=CH₂ | S | 2-(5-Me-oxazoline-2-yl)-4-CF₃ | |
| 12-10 | 5-OCF₃ | S | 2-CH₂Oet-4-CF₃ | |
| 12-11 | 4-OCH=CHCH₂CF₃ | S | 2-Ome-4-CF₃ | |
| 12-12 | 4-CO₂Et | S | (Z)-2-CH=NOiPr-4-CF₃ | |
| 12-13 | 6-OCF₃ | SO₂ | 2-C(O)Oet-4-CF₃ | |
| 12-14 | 6-CN | SO₂ | 2-C(O)OtBu-4-CF₃ | |
| 12-15 | 6-NO₂ | SO₂ | 2-C(O)OiPr-4-CF₃ | |
| 12-16 | 6-OcPr | NH | 6-Cl-2-C(O)OiPr-4-CF₃ | |
| 12-17 | 3-Me | NH | 3-Br | |
| 12-18 | 3-F | Net | 4-cPr | |

TABLE 23

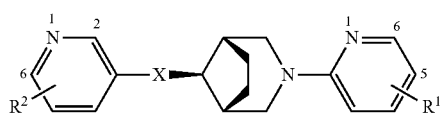

| Compound No. | R² | X | R¹ | Physical constant [ ]: Melting point ° C. |
|---|---|---|---|---|
| 13-1 | 5-CF₃ | O | 5-CF₃ | [79-81] |
| 13-2 | 6-OnPr-5-CF₃ | O | 5-CF₃ | [70-72] |
| 13-3 | 6-Cl-5-CF₃ | O | 5-CF₃ | [100-102] |
| 13-4 | 4-NO₂ | O | 4-cPr | |
| 13-5 | 3-CO₂iPr | O | 3-OcPr | |
| 13-6 | 4-OCH=CHF | S | 3,5-Me₂ | |
| 13-7 | 3-CH=CH₂ | S | 4-CF₃ | |
| 13-8 | 4-OCH₂cPr | S | 5-CO₂Et | |
| 13-9 | 5-CH₂cPr | S | 4-CH=CF₂ | |
| 13-10 | 3-OcPr | S | 5-CH=Cme₂ | |
| 13-11 | 4-cPr | SO₂ | 3-OCH₂CH₂cPr | |
| 13-12 | 4-OCHF₂ | NH | 4-CH₂cPr | |
| 13-13 | 3-Ome | NH | 3-Oet-4-cPr | |
| 13-14 | 4-CN | NH | 4-CHO | |
| 13-15 | 3-CHO | NH | 5-NO₂ | |
| 13-16 | 5-NO₂ | Nme | 5-CF₃ | |
| 13-17 | 4-F | Nac | 4-cPr | |
| 13-18 | 3,5-Me₂ | Nac | 4-CO₂Et | |

TABLE 24

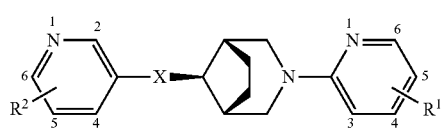

| Compound No. | R² | X | R¹ | Physical constant [ ]: Melting point ° C. |
|---|---|---|---|---|
| 14-1 | 2-OiBu-6-CF₃ | O | 5-CF₃ | nD22.5-1.5074 |
| 14-2 | 5-CF₃-6-OnPr | O | 5-CF₃ | [70-72] |
| 14-3 | 5-CHO | O | 5-CF₃ | |
| 14-4 | 4-OMe | O | 4-cPr | |
| 14-5 | 4-cPr | S | 3-OcPr | |
| 14-6 | 5-OcHex | S | 3,5-Me₂ | |
| 14-7 | 4-CH₂CH₂cPr | S | 4-CF₃ | |
| 14-8 | 4-OCH₂cPr | S | 5-CO₂Et | |
| 14-9 | 4-OCH=CH₂ | S | 4-CH=CF₂ | |
| 14-10 | 5-OCF₃ | SO₂ | 5-CH=Cme₂ | |
| 14-11 | 4-OCH=CHCH₂CF₃ | SO | 3-OCH₂CH₂cPr | |
| 14-12 | 4-CO₂Et | SO | 4-CH₂cPr | |
| 14-13 | 6-F | NH | 3-Oet-4-cPr | |
| 14-14 | 6-CN | NH | 4-CHO | |
| 14-15 | 6-NO₂ | NH | 4-Ome | |
| 14-16 | 6-OcPr | Nme | 3-F | |
| 14-17 | 2-Me | Nac | 4-CO₂Me | |
| 14-18 | 2-F | Nac | 5-CH₂CH₂cPr | |

TABLE 25

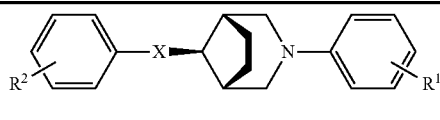

| Compound No. | R² | X | R¹ | Physical constant [ ]: Melting point ° C. |
|---|---|---|---|---|
| 15-1 | 2-OCH₂cPr-4-CF₃ | O | 4-CF₃ | vis |
| 15-2 | 2-OCH₂CH(F)Me-4-CF₃ | O | 2-F | |
| 15-3 | 2-OnPr-4-CF₃ | O | 3,4-Me₂ | |
| 15-4 | 2-OnPr-4-CF₃ | S | 3-OMe | |
| 15-5 | 4-CF₃ | S | 3-CHO | |

TABLE 25-continued

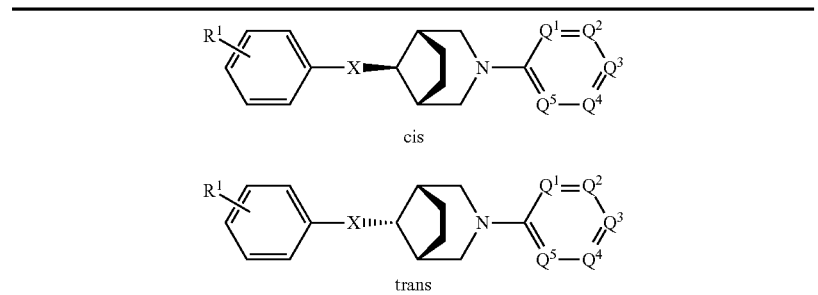

| Compound No. | R² | X | R¹ | Physical constant [ ]: Melting point ° C. |
|---|---|---|---|---|
| 15-6 | 2-CF₃-3-Cl | S | 4-NO₂ | |
| 15-7 | 4-CF₃ | SO | 2-CO₂Et | |
| 15-8 | 4-CF₃-2-OnPr | SO | 3-CH=CHEt | |
| 15-9 | 3-CF₃ | SO | 4-OCH=CHMe | |
| 15-10 | 3-Me | SO₂ | 3-OCF₃ | |
| 15-11 | 3-F | SO₂ | 4-OCH=CF₂ | |
| 15-12 | 2-CN | NH | 2-CF₃-3-Cl | |
| 15-13 | 3-NO₂ | NH | 4-CF₃ | |
| 15-14 | 2-CH=Cme₂ | NH | 4-CF₃-2-OnPr | |
| 15-15 | 3-OCH=CF₂ | Nac | 3-CF₃ | |
| 15-16 | 4-CH₂CH₂CH₂cPr | Nme | 3-Me | |
| 15-17 | 2-OcPr-4-CF₃ | O | 4-CF₃ | vis |

TABLES 26-29

| Compound No. | R¹ | Q¹ | Q² | Q³ | Q⁴ | Q⁵ | X | Physical constant [ ]: Melting point ° C. | Remark |
|---|---|---|---|---|---|---|---|---|---|
| 16-1 | 2-OnPr-4-CF₃ | CH | N | C—CF₃ | CH | CH | O | [79-80] | cis |
| 16-2 | 2-OnPr-4-CF₃ | N | CH | C—CF₃ | N | CH | O | vis | cis |
| 16-3 | 2-OnPr-4-CF₃ | N | N | C—CF₃ | CH | CH | O | [100-103] | cis |
| 16-4 | 2-CO₂iPr-4-CF₃ | N | N | C—CF₃ | CH | CH | O | vis | cis |
| 16-5 | 2-CH₂OEt-4-CF₃ | N | N | C—CF₃ | CH | CH | O | [99-102] | cis |
| 16-6 | 2-OCH₂CH(Me)Ome-4-CF₃ | N | N | C—CF₃ | CH | CH | O | [103-105] | cis |
| 16-7 | 2-OnPr-4-CF₃ | N | N | C—Cl | CH | CH | O | [103-105] | cis |
| 16-8 | 2-OCH₂cPr-4-CF₃ | N | N | C—CN | CH | CH | O | [106-108] | cis |
| 16-9 | 2-OCH₂CH(Me)Ome-4-CF₃ | N | N | C—CN | CH | CH | O | [130-131] | cis |
| 16-10 | 2-CH₂OCH(Me)Ome-4-CF₃ | N | N | C—CF₃ | CH | CH | O | [132-135] | cis |
| 16-11 | 2-OCH₂cPr-4-CF₃ | N | N | C—CF₃ | CH | CH | O | [107-110] | cis |
| 16-12 | 2-ON=C(Me)₂-4-CF₃ | N | N | C—CF₃ | CH | CH | O | [121-124] | cis |
| 16-13 | 2-ON=C(Me)Ome-4-CF₃ | N | N | C—CF₃ | CH | CH | O | [108-111] | cis |
| 16-14 | 2-CO₂iPr-4-CF₃ | N | N | C—CN | CH | CH | O | [153-155] | cis |
| 16-15 | 2-ON=C(Me)2-4-CF₃ | N | N | C—CN | CH | CH | O | [132-134] | cis |
| 16-16 | 2-OCH₂C(Me)=CH₂-4-CF₃ | N | N | C—CF₃ | CH | CH | O | [121-124] | cis |
| 16-17 | 2-OiBu-4-CF₃ | N | N | C—CF₃ | CH | CH | O | [107-110] | cis |
| 16-18 | 2-CH(OH)CH₂iPr-4-CF₃ | N | N | C—CF₃ | CH | CH | O | [72-75] | cis |
| 16-19 | 2-OCH₂CH(F)Me-4-CF₃ | N | N | C—CF₃ | CH | CH | O | [98-102] | cis |
| 16-20 | 2-O(allyl)-4-CF₃ | N | N | C—CF₃ | CH | CH | O | [101-104] | cis |
| 16-21 | 2-O(propargyl)-4-CF₃ | N | N | C—CF₃ | CH | CH | O | [107-111] | cis |
| 16-22 | 2-OnPr-4-CF₃ | N | N | C—CF₃ | CH | CH | O | [206-209] | Sulfate cis |
| 16-23 | 2-OnPr-4-CF₃ | N | N | C—CF₃ | CH | CH | O | [220up] | Borate cis |
| 16-24 | 2-OCH₂cPr-4-CF₃ | CH | N | C—CN | CH | CH | O | nD23.3-1.5840 | cis |
| 16-25 | 2-OnPr-4-NO₂ | N | N | C—CF₃ | CH | CH | O | [128-132] | cis |
| 16-26 | 2-OnPr-4-Cl | N | N | C—CF₃ | CH | CH | O | nD23.4-1.5447 | cis |
| 16-27 | 4-CF₃ | N | N | C—CF₃ | CH | CH | O | [155-156] | cis |
| 16-28 | 4-OCF₃ | N | N | C—CF₃ | CH | CH | O | | cis |
| 16-29 | 2-OCH₂CH(Cl)Me-4-CF₃ | N | N | C—CF₃ | CH | CH | O | [101-105] | cis |
| 16-30 | 2-OCH₂cPr-4-CN | N | N | C—CF₃ | CH | CH | O | [136-138] | cis |
| 16-31 | 2-NHnPr-4-CF₃ | N | N | C—CF₃ | CH | CH | O | [129-130] | cis |
| 16-32 | 2-NHCH₂cPr-4-CF₃ | N | N | C—CF₃ | CH | CH | O | [131-132] | cis |
| 16-33 | 2-Br-4-CF₃ | N | N | C—CF₃ | CH | CH | O | [126-127] | cis |
| 16-34 | 2-CF₃-3-Cl | N | CH | CH | N | CH | S | | cis |
| 16-35 | 4-CF₃ | N | CH | CH | N | CH | S | | cis |

TABLES 26-29-continued

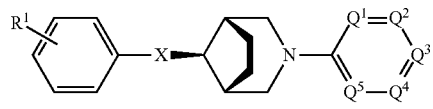

cis

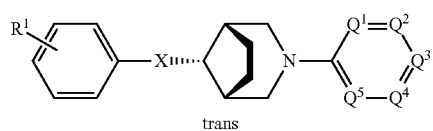

trans

| Compound No. | R¹ | Q¹ | Q² | Q³ | Q⁴ | Q⁵ | X | Physical constant [ ]: Melting point ° C. | Remark |
|---|---|---|---|---|---|---|---|---|---|
| 16-36 | 4-CF₃-2-OnPr | N | CH | C—CF₃ | CH | N | S | | cis |
| 16-37 | 3-CF₃ | N | C—Br | CH | CH | N | SO | | cis |
| 16-38 | 3-Me | N | CH | N | CH | N | SO₂ | | cis |
| 16-39 | 3-F | N | CH | C—CN | CH | N | NH | | cis |
| 16-40 | 2-CN | N | C—CN | CH | CH | N | Nme | | cis |
| 16-41 | 4-CF₃ | N | N | C—CF₃ | CH | CH | O | [159-160] | trans |
| 16-42 | 2-OniPr-4-CF₃ | N | N | C—CF₃ | CH | CH | O | [131-133] | trans |
| 16-43 | 2-OCH₂cPr-4-CF₃ | N | N | C—CF₃ | CH | CH | O | [112-114] | trans |
| 16-44 | 2-CF₃-3-Cl | N | N | C—CF₃ | CH | CH | S | | trans |
| 16-45 | 4-CF₃ | N | CH | CH | N | CH | S | | trans |
| 16-46 | 4-CF₃-2-OnPr | N | CH | CH | N | CH | S | | trans |
| 16-47 | 3-CF₃ | N | CH | C—CF₃ | CH | N | SO | | trans |
| 16-48 | 3-Me | N | C—Br | CH | CH | N | SO | | trans |
| 16-49 | 3-F | N | CH | N | CH | N | SO | | trans |
| 16-50 | 2-CN | N | CH | C—CN | CH | N | SO₂ | | trans |
| 16-51 | 3-NO₂ | N | C—CN | CH | CH | N | SO₂ | | trans |
| 16-52 | 4-CHO | N | N | C—CF₃ | CH | CH | SO₂ | | trans |
| 16-53 | 4-Ome | N | N | C—CF₃ | CH | CH | SO₂ | | trans |
| 16-54 | 4-cPr | N | N | C—CF₃ | CH | CH | NH | | trans |
| 16-55 | 2-OcHex | N | N | C—CF₃ | CH | CH | NH | | trans |
| 16-56 | 3-CH₂CH₂cPr | N | CH | CH | N | CH | NH | | trans |
| 16-57 | 4-OCH₂cPr | N | CH | CH | N | CH | Nme | | trans |
| 16-58 | 2-CHO | N | CH | CH | N | CH | Nme | | trans |
| 16-59 | 3-OCH=CHMe | N | CH | CH | N | CH | Nac | | trans |
| 16-60 | 2-CO₂Et | N | CH | CH | N | CH | Nac | | trans |
| 16-61 | 4-CF₃ | N | CH | C—CF₃ | CH | CH | NH | [99-100] | cis |
| 16-62 | 4-CF₃ | N | CH | C—CF₃ | CH | CH | Nac | [116-119] | cis |
| 16-63 | 4-CF₃ | N | CH | C—CF₃ | CH | CH | Nme | [142-143] | cis |
| 16-64 | 2-NO₂-4-CF₃ | N | CH | C—CF₃ | CH | CH | NH | [140-143] | cis |
| 16-65 | 2-NO₂-4-CF₃ | N | CH | C—CF₃ | CH | CH | Nme | [124-127] | cis |
| 16-66 | 2-NO₂-4-CF₃ | N | CH | C—CF₃ | CH | CH | NnPr | amor | cis |
| 16-67 | 2-NO₂-4-CF₃ | N | CH | C—CF₃ | CH | CH | NnPr | amor | cis |
| 16-68 | 2-NO₂-4-CF₃ | N | CH | C—CF₃ | CH | CH | Net | [112-114] | cis |
| 16-69 | 2-Me-4-OCF₃ | N | CH | C—CF₃ | CH | CH | NH | [89-90] | cis |
| 16-70 | 2-Me-4-OCF₃ | N | CH | C—CF₃ | CH | CH | Nme | nD24.6-1.5115 | cis |
| 16-71 | 2-Oet-4-tBu | N | CH | C—CF₃ | CH | CH | NH | vis | cis |
| 16-72 | 2-Oet-4-tBu | N | CH | C—CF₃ | CH | CH | Nme | vis | cis |
| 16-73 | 2-OnPr-4-CF₃ | N | CH | C—CF₃ | CH | CH | NH | [85-87] | cis |
| 16-74 | 2-OnPr-4-CF₃ | N | CH | C—CF₃ | CH | CH | Nme | [101-103] | cis |
| 16-75 | 2-nBu-4-CF₃ | N | CH | C—CF₃ | CH | CH | NH | [70-73] | cis |
| 16-76 | 2,6-nBu₂-4-CF₃ | N | CH | C—CF₃ | CH | CH | NH | nD22.0-1.5080 | cis |
| 16-77 | 5-Cl-2-OnPr-4-CF₃ | N | CH | C—CF₃ | CH | CH | NH | vis | cis |
| 16-78 | 2,6-Me₂-4-OCF₃ | N | CH | C—CF₃ | CH | CH | NH | [70-73] | cis |
| 16-79 | 2-OnPr-4-CF₃ | N | CH | C—CF₃ | CH | CH | NH | [103-104] | cis |
| 16-80 | 2-OnPr-4-CF₃ | N | CH | C—CF₃ | CH | CH | NH | [107-109] | cis |
| 16-81 | 2-OnPr-4-C(O)OtBu | N | CH | C—CF₃ | CH | CH | NH | [152-154] | cis |
| 16-82 | 2-OnPr-4-CF₃ | N | CH | C—CN | CH | CH | O | [95-99] | cis |
| 16-83 | 2-OCH₂cPr-4-CF₃ | N | CH | C—CN | CH | CH | O | [87-89] | cis |
| 16-84 | 2-OCH₂Ome-4-CF₃ | N | CH | C—CN | CH | CH | O | [117-119] | cis |
| 16-85 | 2-OCH₂CH₂Ome-4-CF₃ | N | CH | C—CN | CH | CH | O | [90-92] | cis |
| 16-86 | 2-OCH₂CH(Ome)Me-4-CF₃ | N | CH | C—CN | CH | CH | O | [78-81] | cis |
| 16-87 | 2-CO₂CHMe₂-4-CF₃ | N | CH | C—CN | CH | CH | O | [142-145] | cis |
| 16-88 | 2-CH₂OCH(Me)Ome-4-CF₃ | N | CH | C—CN | CH | CH | O | [119-122] | cis |
| 16-89 | 2-ON=Cme₂-4-CF₃ | N | CH | C—CN | CH | CH | O | [120-122] | cis |
| 16-90 | 2-ON=C(Ome)Me-4-CF₃ | N | CH | C—CN | CH | CH | O | [124-127] | cis |
| 16-91 | 2-ON=C(NH₂)Me-4-CF₃ | N | CH | C—CN | CH | CH | O | [142-145] | cis |

TABLE 30-31

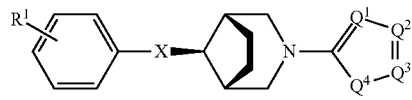

| Compound No. | R¹ | Q¹ | Q² | Q³ | Q⁴ | X | Physical constant [ ]: Melting point °C. |
|---|---|---|---|---|---|---|---|
| 17-1 | 2-OnPr-4-CF₃ | N | C—CF₃ | C—Br | S | O | vis |
| 17-2 | 2-OniPr-4-CF₃ | N | C—CF₃ | CH | S | O | vis |
| 17-3 | 2-OnPr-4-CF₃ | N | CH | C—CO₂Me | S | O | [90-91] |
| 17-4 | 2-OnPr-4-CF₃ | N | CH | C—CH₂OH | S | O | [135-137] |
| 17-5 | 2-OnPr-4-CF₃ | N | CH | C—CHO | S | O | [107-109] |
| 17-6 | 2-OnPr-4-CF₃ | N | CH | C—CF₂H | 5 | O | vis |
| 17-7 | 2-OCH₂cPr-4-CF₃ | N | N | C—CF₃ | S | O | vis |
| 17-8 | 2-CO₂iPr-4-CF₃ | N | N | C—CF₃ | S | O | nD22.3-1.5038 |
| 17-9 | 2-OnPr-4-CF₃ | N | N | C—CF₃ | S | O | nD22.4-1.5148 |
| 17-10 | 2-ON=C(Me)2-4-CF₃ | N | N | C—CF₃ | S | O | [113-115] |
| 17-11 | 2-OnPr-4-CF₃ | CH | CH | CH | CH₂ | O | [140-142] |
| 17-12 | 2-CF₃-3-Cl | CH | CH | CH | NH | S | |
| 17-13 | 4-CF₃ | N | C—Cl | CH | NH | S | |
| 17-14 | 4-CF₃-2-OnPr | N | CH | CH | NH | S | |
| 17-15 | 3-CF₃ | N | C—CN | CH | NH | S | |
| 17-16 | 3-Me | CH | CH | CH | O | SO | |
| 17-17 | 3-F | C—Cl | CH | C—Cl | O | SO | |
| 17-18 | 2-CN | N | CH | CH | O | SO | |
| 17-19 | 3-NO₂ | N | CH | CH | O | SO | |
| 17-20 | 4-CHO | CH | N | CH | O | SO | |
| 17-21 | 4-OMe | CH | N | CH | O | SO₂ | |
| 17-22 | 4-cPr | N | CH | CH | Nme | SO₂ | |
| 17-23 | 2-OcHex | N | CH | CH | Nme | NH | |
| 17-24 | 3-CH₂CH₂cPr | CH | N | CH | Nme | NH | |
| 17-25 | 4-OCH₂cPr | CH | N | CH | Nme | NH | |
| 17-26 | 2-CHO | CH | N | CH | Nme | Nme | |

TABLE 32

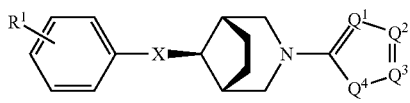

| Compound No. | R¹ | Q¹ | Q² | Q³ | Q⁴ | X | Physical constant [ ]: Melting point °C. |
|---|---|---|---|---|---|---|---|
| 18-1 | 2-OnPr-4-CF₃ | N | NH | C—CF₃ | CH | O | [140-142] |
| 18-2 | 2-OnPr-4-CF₃ | N | CH₂ | C—Br | CH | O | |
| 18-3 | 2-OnPr-4-CF₃ | N | CMe₂ | CH | CH | O | |
| 18-4 | 2-OnPr-4-CF₃ | N | O | C—CO₂Me | CH | S | |
| 18-5 | 2-OnPr-4-CF₃ | N | O | C—CH₂OH | CH | S | |
| 18-6 | 2-OnPr-4-CF₃ | N | S | C—CHO | CH | SO₂ | |
| 18-7 | 2-OnPr-4-CF₃ | N | S | C—CF₂H | C—Cl | NH | |
| 18-8 | 2-OCH₂cPr-4-CF₃ | N | NH | C—CF₃ | Cme | NH | |
| 18-9 | 2-CO₂iPr-4-CF₃ | N | Nme | C—CF₃ | C—CF₃ | NH | |
| 18-10 | 2-OnPr-4-CF₃ | N | Nme | C—CF₃ | C—CF₃ | Nme | |
| 18-11 | 2-ON=C(Me)₂-4-CF₃ | N | Nme | C—CF₃ | C—CF₃ | O | |
| 18-12 | 2-OnPr-4-CF₃ | CH | Nme | CH | CH | O | |

TABLES 33-34

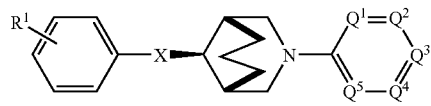

| Compound No. | R¹ | Q¹ | Q² | Q³ | Q⁴ | Q⁵ | X | Physical constant [ ]: Melting point ° C. |
|---|---|---|---|---|---|---|---|---|
| 19-1 | 2-OnPr-4-CF$_3$ | N | N | C—CF$_3$ | CH | CH | O | [125-127] |
| 19-2 | 2-OCH$_2$cPr-4-CF$_3$ | N | N | C—CF$_3$ | CH | CH | O | [115-118] |
| 19-3 | 2-OEt-4-CF$_3$ | N | N | C—CF$_3$ | CH | CH | O | [141-143] |
| 19-4 | 2-OCH$_2$OMe-4-CF$_3$ | N | N | C—CF$_3$ | CH | CH | O | [118-121] |
| 19-5 | 2-OiBu-4-CF$_3$ | N | N | C—CF$_3$ | CH | CH | O | [130-133] |
| 19-6 | 2-CO$_2$iPr-4-CF$_3$ | N | N | C—CF$_3$ | CH | CH | O | amor |
| 19-7 | 2-CH$_2$OEt-4-CF$_3$ | N | N | C—CF$_3$ | CH | CH | O | [144-146] |
| 19-8 | 2-OCH$_2$CH(Me)OMe-4-CF$_3$ | N | N | C—CF$_3$ | CH | CH | O | [114-115] |
| 19-9 | 2-OCH$_2$cPr-4-CF$_3$ | CH | CH | CH | CH | CH | O | vis |
| 19-10 | 2-OnPr-4-CF$_3$ | N | N | C—CF$_3$ | CH | CH | O | |
| 19-11 | 2-OnPr-4-CF$_3$ | N | N | C—CF$_3$ | CH | CH | O | |
| 19-12 | 4-CF$_3$ | N | CH | CH | N | C—Me | S | |
| 19-13 | 2-CF$_3$-3-Cl | N | CH | CH | N | CH | S | |
| 19-14 | 4-CF$_3$ | N | CH | C—CF$_3$ | N | CH | S | |
| 19-15 | 4-CF$_3$-2-OnPr | N | C—Br | CH | N | CH | S | |
| 19-16 | 3-CF$_3$ | N | CH | CH | N | CH | S | |
| 19-17 | 3-Me | N | CH | C—CN | CH | CH | SO | |
| 19-18 | 3-F | N | C—CN | CH | CH | CH | SO | |
| 19-19 | 2-CN | N | CH | N | CH | CH | SO | |
| 19-20 | 3-NO2 | CH | N | C—CN | CH | CH | SO$_2$ | |
| 19-21 | 2-CH=CMe$_2$ | N | CH | CH | CH | N | SO$_2$ | |
| 19-22 | 3-OCH=CF$_2$ | C—Me | N | CH | CH | CH | SO$_2$ | |
| 19-23 | 4-CH$_2$CH$_2$CH$_2$cPr | N | C—F | CH | CH | N | NH | |
| 19-24 | 2-OnPr-4-CF$_3$ | N | C—Cl | CH | CH | N | NH | |
| 19-25 | 2-OnPr-4-CF$_3$ | N | CH | N | CH | CH | NH | |
| 19-26 | 4-CHO | CH | C—Me | N | C—Me | CH | NMe | |
| 19-27 | 3-OCF$_3$ | N | N | C—CF$_3$ | CH | CH | NMe | |
| 19-28 | 2-CO$_2$Et | N | N | CH | CH | CH | NAc | |

TABLE 35

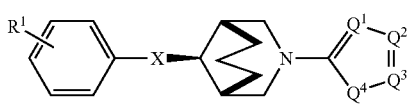

| Compound No. | R¹ | Q¹ | Q² | Q³ | Q⁴ | X | Physical constant [ ]: Melting point ° C. |
|---|---|---|---|---|---|---|---|
| 20-1 | 2-OcPr-4-CF$_3$ | N | N | C—CF$_3$ | S | O | [116-119] |
| 20-2 | 2-CO$_2$iPr-4-CF$_3$ | N | N | C—CF$_3$ | S | O | vis |
| 20-3 | 4-CF$_3$ | N | CH | C—Br | CH$_2$ | O | |
| 20-4 | 4-CF$_3$-2-OnPr | N | CMe | CH | CH$_2$ | O | |
| 20-5 | 3-CF$_3$ | N | N | C—CO$_2$Me | CH$_2$ | O | |
| 20-6 | 3-Me | N | N | C—CH$_2$OH | CH$_2$ | S | |
| 20-7 | 3-F | N | CH | C—CHO | CH$_2$ | S | |
| 20-8 | 2-CN | N | CH | C—CF$_2$H | CH$_2$ | S | |
| 20-9 | 3-NO$_2$ | N | N | C—CF$_3$ | Cme$_2$ | S | |
| 20-10 | 2-CH=Cme$_2$ | N | N | C—CF$_3$ | Cme$_2$ | SO | |
| 20-11 | 3-OCH=CF$_2$ | N | N | C—CF$_3$ | Cme$_2$ | SO | |
| 20-12 | 4-CH$_2$CH$_2$CH$_2$cPr | N | N | C—CF$_3$ | CH$_2$ | SO$_2$ | |
| 20-13 | 2-OnPr-4-CF$_3$ | CH | N | CH | CH$_2$ | SO$_2$ | |
| 20-14 | 2-OnPr-4-CF$_3$ | N | CH | C—Br | CH$_2$ | SO$_2$ | |
| 20-15 | 4-CHO | N | Cme | CH | CH$_2$ | NH | |
| 20-16 | 3-OCF$_3$ | N | Cme | C—CO$_2$Me | CH$_2$ | NH | |
| 20-17 | 4-cPr | CH | CH | N | NH | Nme | |

TABLES 36-39

| Compound No. | Cy¹ | X | Y | Cy¹ | Physical constant [ ]: Melting point °C. | cis/trans |
|---|---|---|---|---|---|---|
| 21-1 | cyclopropylmethoxy-4-CF₃-phenyl | O | NH | 2-pyridyl-5-CF₃ | vis | Cis |
| 21-2 | cyclopropylmethoxy-4-CF₃-phenyl | O | NH | 2-pyridyl-5-CF₃ | 165-167 | Trans |
| 21-3 | cyclopropylmethoxy-4-CF₃-phenyl | O | NMe | 2-pyridyl-5-CF₃ | vis | Cis |
| 21-4 | cyclopropylmethoxy-4-CF₃-phenyl | O | NCO₂Me | 2-pyridyl-5-CF₃ | 120-122 | Cis |
| 21-5 | cyclopropylmethoxy-4-CF₃-phenyl | O | S | 2-pyridyl-5-CF₃ | nD22.2-1.5418 | Cis |
| 21-6 | cyclopropylmethoxy-4-CF₃-phenyl | O | SO₂ | 2-pyridyl-5-CF₃ | 155-158 | Cis |
| 21-7 | 5-CF₃-2-pyridyl | O | O | 5-CF₃-1,3,4-thiadiazol-2-yl | 156-157 | Trans |
| 21-8 | 5-CF₃-2-pyridyl | O | O | 5-CF₃-1,3,4-thiadiazol-2-yl | 124-125 | Cis |

TABLES 36-39-continued

| Compound No. | Cy¹ | X | Y | Cy¹ | Physical constant [ ]: Melting point °C. | cis/trans |
|---|---|---|---|---|---|---|
| 21-9 | 5-CF₃-pyridin-2-yl | O | O | 6-CF₃-pyridazin-3-yl | 125-126 | Trans |
| 21-10 | 5-CF₃-3-Cl-pyridin-2-yl | O | O | 5-CF₃-1,3,4-thiadiazol-2-yl | vis | Cis |
| 21-11 | 4-CF₃-phenyl | O | O | 5-CF₃-1,3,4-thiadiazol-2-yl | 127-128 | Trans |
| 21-12 | 4-CF₃-phenyl | O | O | 5-CF₃-1,3,4-thiadiazol-2-yl | 146-147 | Cis |
| 21-13 | 4-CF₃-phenyl | O | O | 6-CF₃-pyridazin-3-yl | 102-103 | trans |
| 21-14 | 4-CF₃-2-(cyclopropylmethoxy)phenyl | O | S | 6-CF₃-pyridazin-3-yl | 125-128 | Cis |
| 21-15 | 4-CF₃-2-(cyclopropylmethoxy)phenyl | O | S | 5-CF₃-1,3,4-thiadiazol-2-yl | 52-55 | Cis |
| 21-16 | 4-CF₃-2-(cyclopropylmethoxy)phenyl | O | S | 5-CN-pyridin-2-yl | 136-138 | Cis |
| 21-17 | 4-CF₃-2-(cyclopropylmethoxy)phenyl | O | SO₂ | 5-CN-pyridin-2-yl | 200up | Cis |

TABLES 36-39-continued

| Compound No. | Cy¹ | X | Y | Cy¹ | Physical constant [ ]: Melting point °C. | cis/trans |
|---|---|---|---|---|---|---|
| 21-18 | cyclopropylmethoxy-CF₃-phenyl | O | O | 3-CF₃-pyridazin-6-yl | 93-95 | Cis |
| 21-19 | 4-F₃CO-naphthalen-1-yl | O | SO₂ | 6-Cl-pyrazin-2-yl | | Cis |
| 21-20 | 3-vinyl-furan-2-yl | O | SO₂ | 3-CF₃-pyridazin-6-yl | | Trans |
| 21-21 | 5-Me₂N-thiophen-2-yl | S | NH | 2-OMe-3-CN-pyridin-6-yl | | Cis |
| 21-22 | 5-vinyloxy-1H-pyrrol-2-yl | S | S | 5-CO₂Et-1H-pyrrol-2-yl | | Cis |
| 21-23 | 4-F₃CO-oxazol-2-yl | S | S | 5-Ph-1H-imidazol-2-yl | | Trans |
| 21-24 | 4-EtO₂C-1H-imidazol-2-yl | S | O | 5-vinyl-furan-2-yl | | Trans |
| 21-25 | 4-MeCONH-thiazol-2-yl | SO | NMe | 3-F₃CO-pyrazin-2-yl | | Cis |
| 21-26 | 2-NC-1,3,4-thiadiazol-5-yl | SO₂ | NH | 6-(N=C(Me)₂-oxy)-pyridazin-3-yl | | Trans |
| 21-27 | 2-OHC-1,3,4-oxadiazol-5-yl | NH | SO₂ | 6-SMe-pyridin-2-yl | | Cis |

TABLES 36-39-continued

| Compound No. | Cy¹ | X | Y | Cy¹ | Physical constant [ ]: Melting point ° C. | cis/trans |
|---|---|---|---|---|---|---|
| 21-28 | 3-cyclopropyl-1H-1,2,4-triazol-5-yl | NH | S | 5-nitro-1,3,4-thiadiazol-2-yl | | Trans |
| 21-29 | 6-phenylpyridazin-3-yl | Nme | O | 2-OMe-3-CN-pyridin-6-yl | | Cis |

TABLES 40-42

| Compound No. | R² | X | R¹ | Physical constant [ ]: Melting point ° C. | Remark |
|---|---|---|---|---|---|
| 22-1 | 5-CF₃ | O | 2-OnPr-4-CF₃ | nD21.8-1.5022 | |
| 22-2 | 5-CF₃ | O | 2-CHO-4-CF₃ | vis | |
| 22-3 | 5-CF₃ | O | 2-CH₂OH-4-CF₃ | vis | |
| 22-4 | 5-CF₃ | O | 2-CH₂OCH(OMe)-4-CF₃ | 90-92 | |
| 22-5 | 5-CF₃ | O | 2-CH₂Oet-4-CF₃ | nD22.4-1.4919 | |
| 22-6 | 5-CF₃ | O | 2-C(O)OiPr-4-CF₃ | vis | $R^3_a$ = Et, trans |
| 22-7 | 5-CF₃ | O | 2-C(O)OiiPr-4-CF₃ | vis | $R^3_a$ = Et, cis |
| 22-8 | 5-CF₃ | O | 2-C(O)OiPr-4-CF₃ | 84-86 | |
| 22-9 | 5-CF₃ | O | 2-OnPr-4-CF₃ | vis | $R^1_a$ = Et, trans |
| 22-10 | 5-CF₃ | O | 2-OnPr-4-CF₃ | vis | $R^1_a$ = Et, cis |
| 22-11 | 5-CF₃ | O | 4-CF₃ | nD22.3-1.5079 | $R^1_a$ = Et, cis |
| 22-12 | 5-CF₃ | O | 4-CF₃ | nD22.2-1.5089 | $R^1_a$ = Et, trans |
| 22-13 | 5-CN | O | 2-OnPr-4-CF₃ | | |
| 22-14 | 5-CF₃ | O | 2-CHO-4-CF₃ | | |
| 22-15 | 3-Me | O | 2-CH₂OH-4-CF₃ | | |
| 22-16 | 3-F | O | 2-CH₂OCH(Ome)Me-4-CF₃ | | $R^1_a$ = OH, trans |
| 22-17 | 5-CN | O | 2-CH₂Oet-4-CF₃ | | $R^1_a$ = F, cis |
| 22-18 | 5-NO₂ | O | 2-Cl-4-CF₃ | | |
| 22-19 | 5-CHO | S | 2-C(O)OiPr-4-CF₃ | | |
| 22-20 | 4-Ome | S | 2,6-(NO₂)₂-4-CF₃ | | |
| 22-21 | 4-cPr | S | 2-C(O)NHCH(Me)CH₂OhiPr-4-CF₃ | | $R^3_a$ = Nme₂, trans |
| 22-22 | 5-OcHex | S | 2-CHNOEt-4-CF₃ | | $R^1_a$ = NO₂, cis |
| 22-23 | 3-CH₂CH₂cPr | S | 2-CH=NoiPr-4-CF₃ | | |
| 22-24 | 4-OCH₂cPr | S | 2-CH=NO-propargyl-4-CF₃ | | |
| 22-25 | 4-OCH=CH₂ | S | 2-(5-Me-oxazoline-2-yl)-4-CF₃ | | $R^3_a$ = CN, trans |
| 22-26 | 5-OCF₃ | S | 2-CH₂Oet-4-CF₃ | | |
| 22-27 | 4-OCH=CHCH₂CF₃ | S | 2-Ome-4-CF₃ | | |
| 22-28 | 4-CO₂Et | SO | 2-CHNoiPr-4-CF₃ | | |
| 22-29 | 6-F | SO | 2-C(O)Oet-4-CF₃ | | $R^3_a$ = CHO, trans |
| 22-30 | 6-CN | SO | 2-C(O)OtBu-4-CF₃ | | $R^1_a$ = Ome, cis |

TABLES 40-42-continued

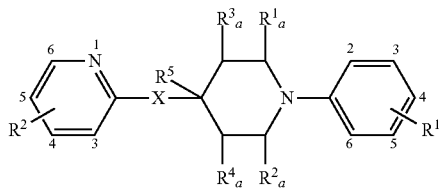

| Compound No. | R² | X | R¹ | Physical constant [ ]: Melting point ° C. | Remark |
|---|---|---|---|---|---|
| 22-31 | 6-NO₂ | SO₂ | 2-C(O)OiPr-4-CF₃ | | |
| 22-32 | 6-OcPr | SO₂ | 6-Cl-2-C(O)OiPr-4-CF₃ | | $R^3_a$ = OCF₃, trans |
| 22-33 | 5-CN | SO₂ | 2-CH=NOMe-4-CF₃ | | $R^1_a$ = CF3, cis |
| 22-34 | 5-CF₃ | SO₂ | 2-CH=NOMe-4-CF₃ | | |
| 22-35 | 3-Me | SO₂ | 2-C(O)OCH₂cPr-4-CF₃ | | |
| 22-36 | 3-F | SO₂ | 2-C(O)OCH₂CF₃-4-CF₃ | | |
| 22-37 | 5-CN | SO₂ | 2-C(O)OiBu-4-CF₃ | | |
| 22-38 | 5-NO₂ | SO₂ | 2-C(O)OnPr-4-CF₃ | | |
| 22-39 | 5-CHO | NH | 2-CH(OH)CH₂CH(Me)2-4-CF₃ | | $R^1_a$ = Sme, cis |
| 22-40 | 4-Ome | NH | 2-C(O)OCH(Me)CH=CH₂-4-CF₃ | | |
| 22-41 | 5-CF₃ | NH | 2-C(O)OcPen-4-CF₃ | | $R^3_a$ = CO₂Et, trans |
| 22-42 | 4-CF₃-6-Cl | NH | 2-C(O)ON=C(Me)2-4-CF₃ | | |
| 22-43 | 5-CF₃ | NH | 2-OCH₂cPr-4-CF₃ | | |
| 22-44 | 5-CF₃-6-OnPr | NH | 2-Oet-4-CF₃ | | |
| 22-45 | 5-CF₃ | NH | 2-C(O)OCH₂CHF₂-4-CF₃ | | |
| 22-46 | 3-Me | NH | 2-OnBu-4-CF₃ | | |
| 22-47 | 3-F | NH | 2-OnPr-4-CN | | |
| 22-48 | 5-CN | NH | 2-C(O)OCH₂Ome-4-CF₃ | | $R^1_a$ = C(S)Ome, cis |
| 22-49 | 5-NO₂ | NH | 2-C(O)OCH₂tBu-4-CF₃ | | |
| 22-50 | 5-CHO | NH | 2-C(O)N(Me)₂-4-CF₃ | | |
| 22-51 | 4-Ome | NH | 2-C(O)OCH(Me)CH(Me)₂-4-CF₃ | | |
| 22-52 | 4-cPr | NH | 2-C(O)OCH(Et)₂-4-CF₃ | | |
| 22-53 | 5-OcHex | Nme | 2-C(O)OtBu-4-CF₃ | | $R^3_a$ = NHSO₂Me, trans |
| 22-54 | 3-CH₂CH₂cPr | Nme | 2-C(O)OiPr-4-CF₃ | | $R^1_a$ = Ph, cis |
| 22-55 | 4-OCH₂cPr | Nme | 2-C(O)O(CH₂)₂Ome-4-CF₃ | | |
| 22-56 | 6-Me | Nac | 2-C(O)OCH(Me)CH₂Ome-4-CF₃ | | |
| 22-57 | 5-OcHex | Nac | 2-C(O)OCH(CN)Me-4-CF₃ | | |
| 22-58 | 3-CH₂CH₂cPr | NAC | 2-C(O)OCH(Cl)Et-4-CF₃ | | |
| 22-59 | 4-OCH=CH₂ | NCO₂Me | 2-C(O)SiPr-4-CF₃ | | |
| 22-60 | 5-OCF₃ | NCO₂Me | 2-Obn-4-CF₃ | | $R^3_a$ = N(SO₂Me)₂, trans |
| 22-61 | 4-OCH=CHCH₂CF₃ | NCO₂Me | 2-OH-4-CF₃ | | $R^1_a$ = Et, cis |
| 22-62 | 4-CO₂Et | NCO₂Me | 2-OCH₂CH(Me)Ome-4-CF₃ | | |
| 22-63 | 4-CF₃-5-Cl | NCO₂Me | 2-CH(OH)CH₂CN-4-CF₃ | | |
| 22-64 | 4-OCH=CHCH₂CF₃ | NCO₂Me | 2-OnPr-4-CF₃ | | |
| 22-65 | — | NCO₂Me | 2-OCH₂cPr-4-C₃F₇ | | |
| 22-66 | 6-Me | NCO₂Me | 4-Ph | | |
| 22-67 | 5-OcHex | NCO₂Me | 2,3,4,5,6-F₅ | | |

Note that R1b, R2b, $R^3_a$, R3b, $R^4_a$, R4b, and R⁵ represent hydrogen atom, respectively, unless otherwise indicated.

Cis and trans represent positional relationship between X and ($R^1_a$, $R^2_a$, $R^3_a$, $R^4_a$, or R⁵).

TABLES 43-45

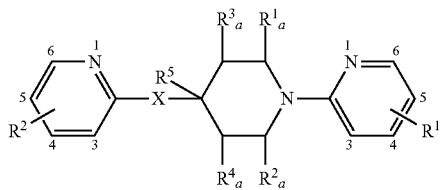

| Compound No. | R² | X | R¹ | Physical constant [ ]: Melting point °C. | Remark |
|---|---|---|---|---|---|
| 23-1 | 5-CF₃ | O | 5-CF₃ | 84-86 | |
| 23-2 | 5-CF₃-6-Cl | O | 5-CF₃ | nD22.0-1.5150 | |
| 23-3 | 5-CF₃ | O | 5-CF₃ | nD22.0-1.5150 | R³ₐ = Et, cis |
| 23-4 | 3-Cl-5-CF₃ | O | 5-CF₃ | nD22.3-1.5149 | R³ₐ = Et, trans |
| 23-5 | 5-CF₃ | O | 5-CF₃ | nD22.4-1.5055 | R³ₐ = Et, trans |
| 23-6 | 5-CF₃ | O | 3-C(O)OiPr-4-CF₃ | | R³ₐ = Et, trans |
| 23-7 | 5-CF₃ | O | 3-C(O)OiPr-4-CF₃ | | R³ₐ = Et, cis |
| 23-8 | 5-CF₃ | O | 3-C(O)OiPr-4-CF₃ | | |
| 23-9 | 5-CF₃ | O | 6-OnPr-4-CF₃ | | R¹ₐ = Et, trans |
| 23-10 | 5-CF₃ | O | 6-OnPr-4-CF₃ | | R¹ₐ = Et, cis |
| 23-11 | 5-CF₃ | O | 4-CF₃ | | R¹ₐ = Et, cis |
| 23-12 | 5-CF₃ | O | 4-CF₃ | | R¹ₐ = Et, trans |
| 23-13 | 5-CN | O | 5-OnPr-4-CF₃ | | |
| 23-14 | 5-CF3 | O | 3-CHO-4-CF₃ | | |
| 23-15 | 3-Me | O | 3-CH₂OH-4-CF₃ | | |
| 23-16 | 3-F | O | 3-CH₂OCH(OMe)Me-4-CF₃ | | R¹ₐ = OH, trans |
| 23-17 | 5-CN | O | 3-CH₂Oet-4-CF₃ | | R¹ₐ = F, cis |
| 23-18 | 5-NO₂ | O | 6-Cl-4-CF₃ | | |
| 23-19 | 5-CHO | S | 5-C(O)OiPr-4-CF₃ | | |
| 23-20 | 4-Ome | S | 5,6-(NO₂)₂-4-CF₃ | | |
| 23-21 | 4-cPr | S | 3-C(O)NHCH(Me)CH₂OH-4-CF₃ | | R³ₐ = Nme₂, trans |
| 23-22 | 5-OcHex | S | 3-CHNOEt-4-CF₃ | | R¹ₐ = NO₂, cis |
| 23-23 | 3-CH₂CH₂cPr | S | 3-CH=NoiPr-4-CF₃ | | |
| 23-24 | 4-OCH₂cPr | S | 3-CH=NO-propargyl-4-CF₃ | | |
| 23-25 | 4-OCH=CH₂ | S | 3-(5-Me-oxazoline-2-yl)-4-CF₃ | | R³ₐ = CN, trans |
| 23-26 | 5-OCF₃ | S | 5-CH₂Oet-4-CF₃ | | |
| 23-27 | 4-OCH=CHCH₂CF₃ | S | 5-Ome-4-CF₃ | | |
| 23-28 | 4-CO₂Et | SO | 5-CH=NoiPr-4-CF₃ | | |
| 23-29 | 6-F | SO | 5-C(O)Oet-4-CF₃ | | R³ₐ = CHO, trans |
| 23-30 | 6-CN | SO | 3-C(O)OtBu-4-CF₃ | | R¹ₐ = Ome, cis |
| 23-31 | 6-NO₂ | SO₂ | 3-C(O)OiPr-4-CF₃ | | |
| 23-32 | 6-OcPr | SO₂ | 6-Cl-2-C(O)OiPr-4-CF₃ | | R³ₐ = OCF₃, trans |
| 23-34 | 5-CN | SO₂ | 3-CH=NOMe-4-CF₃ | | R¹ₐ = CF3, cis |
| 23-35 | 5-CF3 | SO₂ | 3-CH=NOMe-4-CF₃ | | |
| 23-36 | 3-Me | SO₂ | 3-C(O)OCH₂cPr-4-CF₃ | | |
| 23-37 | 3-F | SO₂ | 5-C(O)OCH₂CF₃-4-CF₃ | | |
| 23-37 | 5-CN | SO₂ | 5-C(O)OiBu-4-CF₃ | | |
| 23-38 | 5-NO₂ | SO₂ | 5-C(O)OnPr-4-CF₃ | | |
| 23-39 | 5-CHO | NH | 5-CH(OH)CH₂CH(Me)2-4-CF₃ | | R¹ₐ = Sme, cis |
| 23-40 | 4-Ome | NH | 5-C(O)OCH(Me)CH=CH₂-4-CF₃ | | |
| 23-41 | 5-CF₃ | NH | 5-C(O)OcPen-4-CF₃ | | R³ₐ = CO₂Et, trans |
| 23-42 | 4-CF₃-6-Cl | NH | 5-C(O)ON=C(Me)₂-4-CF₃ | | |
| 23-43 | 5-CF3 | NH | 5-OCH₂cPr-4-CF₃ | | |
| 23-44 | 5-CF₃-6-OnPr | NH | 5-Oet-4-CF₃ | | |
| 23-45 | 5-CF₃ | NH | 6-C(O)OCH₂CHF₂-4-CF₃ | | |
| 23-46 | 3-Me | NH | 6-OnBu-4-CF₃ | | |
| 23-47 | 3-F | NH | 6-OnPr-4-CN | | |
| 23-48 | 5-CN | NH | 6-C(O)OCH₂Ome-4-CF₃ | | R¹ₐ = C(S)Ome, cis |
| 23-49 | 5-NO₂ | NH | 6-C(O)OCH₂tBu-4-CF₃ | | |
| 23-50 | 5-CHO | NH | 6-C(O)N(Me)₂-4-CF₃ | | |
| 23-51 | 4-Ome | NH | 6-C(O)OCH(Me)CH(Me)₂-4-CF₃ | | |
| 23-52 | 4-cPr | NH | 3-C(O)OCH(Et)₂-4-CF₃ | | |
| 23-53 | 5-OcHex | Nme | 3-C(O)Ome-4-CF₃ | | R³ₐ = NHSO₂Me, trans |
| 23-54 | 3-CH₂CH₂cPr | Nme | 3-C(O)OiPr-4-CF₃ | | R¹ₐ = Ph, cis |
| 23-55 | 4-OCH₂cPr | Nme | 3-C(O)O(CH₂)₂Ome-4-CF₃ | | |
| 23-56 | 6-Me | Nac | 3-C(O)OCH(Me)CH₂Ome-4-CF₃ | | |
| 23-57 | 5-OcHex | Nac | 3-C(O)OCH(CN)Me-4-CF₃ | | |
| 23-58 | 3-CH₂CH₂cPr | NAC | 3-C(O)OCH(Cl)Et-4-CF₃ | | |
| 23-59 | 4-OCH=CH₂ | NCO₂Me | 3-C(O)S(iPr)-4-CF₃ | | |
| 23-60 | 5-OCF₃ | NCO₂Me | 3-Obn-4-CF₃ | | R³ₐ = N(SO₂Me)₂, trans |

TABLES 43-45-continued

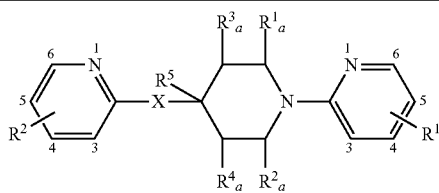

| Compound No. | $R^2$ | X | $R^1$ | Physical constant [ ]: Melting point °C. | Remark |
|---|---|---|---|---|---|
| 23-61 | 4-OCH=CHCH$_2$CF$_3$ | NCO$_2$Me | 3-OH-4-CF$_3$ | | $R^1_a$ = Et, cis |
| 23-62 | 4-CO$_2$Et | NCO$_2$Me | 5-OCH$_2$CH(Me)Ome-4-CF$_3$ | | |
| 23-63 | 6-F | NCO$_2$Me | 5-C(O)OiPr-4-CF$_3$ | | |
| 23-64 | 6-CN | NCO$_2$Me | 5-CH(OTMS)CH$_2$CN-4-CF$_3$ | | |
| 23-65 | 4-CF$_3$-5-Cl | NCO$_2$Me | 5-CH(OH)CH$_2$CN-4-CF$_3$ | | |
| 23-66 | 4-OCH=CHCH$_2$CF$_3$ | NCO$_2$Me | 5-OnPr-4-CF$_3$ | | |
| 23-67 | — | NCO$_2$Me | 5-OCH$_2$cPr-4-C$_3$F$_7$ | | |
| 23-68 | 6-Me | NCO$_2$Me | 4-Ph | | |
| 23-69 | 5-OcHex | NCO$_2$Me | 3,4,5,6-F$_4$ | | |

Note that R1b, R2b, $R^3_a$, R3b, $R^4_a$, R4b, and $R^5$ represent hydrogen atom, respectively, unless otherwise indicated.
Cis and trans represent positional relationship between X and ($R^1_a$, $R^2_a$, $R^3_a$, $R^4_a$, or $R^5$).

TABLES 46-50

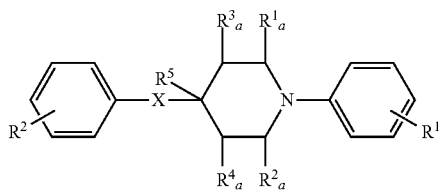

| Compound No. | $R^2$ | X | $R^1$ | Physical constant [ ]: Melting point °C. | Remark |
|---|---|---|---|---|---|
| 24-1 | 4-CF$_3$ | O | 2-NO$_2$-4-CF$_3$ | vis | |
| 24-2 | 4-CF$_3$ | O | 2-NH$_2$-4-CF$_3$ | 80-82 | |
| 24-3 | 4-OCF$_3$ | O | 2-NO$_2$-4-CF$_3$ | nD23.0-1.5210 | |
| 24-4 | 4-CF$_3$ | O | 2-Br-4-CF$_3$ | nD23.0-1.5225 | |
| 24-5 | 4-CF$_3$ | O | 2-Cl-4-CF$_3$ | 61-64 | |
| 24-6 | 4-CF$_3$ | O | 2-F-4-CF$_3$ | 56-58 | |
| 24-7 | 4-CF$_3$ | O | 4-CF$_3$ | 102-105 | |
| 24-8 | 2-Cl-4-CF$_3$ | O | 4-CF$_3$ | vis | |
| 24-9 | 2-Cl-4-CF$_3$ | O | 2-F-4-CF$_3$ | nD22.5-1.5076 | |
| 24-10 | 4-CF$_3$ | O | 4-CF$_3$ | nD22.4-1.5111 | $R^3_a$ = Et, cis |
| 24-11 | 4-CF$_3$ | O | 4-CF$_3$ | nD22.5-1.5055 | $R^3_a$ = Et, trans |
| 24-12 | 5-CF$_3$ | O | 4-CF$_3$ | | |
| 24-13 | 4-CN | O | 2-OnPr-4-CF$_3$ | | |
| 24-14 | 5-CF$_3$ | O | 3-CHO-4-CF$_3$ | | |
| 24-15 | 4-Me | O | 3-CH$_2$OH-4-CF$_3$ | | |
| 24-16 | 3-F | O | 3-CH$_2$OCH(OMe)Me-4-CF$_3$ | | $R^1_a$ = OH, trans |
| 24-17 | 5-CN | O | 2-CH$_2$Oet-4-CF$_3$ | | $R^1_a$ = F, cis |
| 24-18 | 5-NO$_2$ | O | 6-Cl-4-CF$_3$ | | |
| 24-19 | 5-CHO | S | 5-C(O)OiPr-4-CF$_3$ | | |
| 24-20 | 4-Ome | S | 5,6-(NO$_2$)$_2$-4-CF$_3$ | | |
| 24-21 | 4-cPr | S | 3-C(O)NHCH(Me)CH$_2$OH-4-CF$_3$ | | $R^3_a$ = Nme$_2$, trans |
| 24-22 | 5-OcHex | S | 3-CH=NOEt-4-CF$_3$ | | $R^1_a$ = NO$_2$, cis |
| 24-23 | 3-CH$_2$CH$_2$cPr | S | 3-CH=NoiPr-4-CF$_3$ | | |
| 24-24 | 4-OCH$_2$cPr | S | 3-CH=NO-propargyl-4-CF$_3$ | | |
| 24-25 | 4-OCH=CH$_2$ | S | 3-(5-Me-oxazoline-2-yl)-4-CF$_3$ | | |
| 24-26 | 5-OCF$_3$ | S | 5-CH$_2$Oet-4-CF$_3$ | | |
| 24-27 | 4-OCH=CHCH$_2$CF$_3$ | S | 2-Ome-4-CF$_3$ | | $R^3_a$ = CN, trans |
| 24-28 | 4-CO$_2$Et | SO | 5-CH=NoiPr-4-CF$_3$ | | |
| 24-29 | 6-F | SO | 5-C(O)Oet-4-CF$_3$ | | $R^3_a$ = CHO, trans |
| 24-30 | 6-CN | SO | 3-C(O)OtBu-4-CF$_3$ | | $R^1_a$ = Ome, cis |
| 24-31 | 6-NO$_2$ | SO$_2$ | 3-C(O)OiPr-4-CF$_3$ | | |

TABLES 46-50-continued

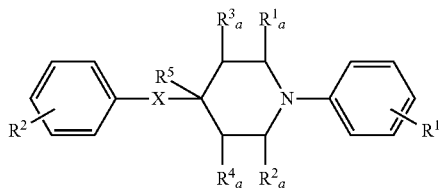

| Compound No. | R² | X | R¹ | Physical constant [ ]: Melting point ° C. | Remark |
|---|---|---|---|---|---|
| 24-32 | 6-OcPr | SO₂ | 6-Cl-2-C(O)OiPr-4-CF₃ | | $R^3_a$ = OCF3, trans |
| 24-33 | 5-CN | SO₂ | 3-CH=NOMe-4-CF₃ | | $R^1_a$ = CF3, cis |
| 24-34 | 5-CF₃ | SO₂ | 3-CH=NOMe-4-CF₃ | | |
| 24-35 | 3-Me | SO₂ | 3-C(O)OCH₂cPr-4-CF₃ | | |
| 24-36 | 3-F | SO₂ | 5-C(O)OCH₂CF₃-4-CF₃ | | |
| 24-37 | 5-CN | SO₂ | 5-C(O)OiBu-4-CF₃ | | |
| 24-38 | 5-NO₂ | SO₂ | 5-C(O)OnPr-4-CF₃ | | |
| 24-39 | 5-CHO | NH | 5-CH(OH)CH₂CH(Me)₂-4-CF₃ | | $R^1_a$ = Sme, cis |
| 24-40 | 4-Ome | NH | 5-C(O)OCH(Me)CH=CH₂-4-CF₃ | | |
| 24-41 | 5-CF₃ | NH | 5-C(O)OcPen-4-CF₃ | | $R^3_a$ = CO2Et, trans |
| 24-42 | 4-CF₃-6-Cl | NH | 5-C(O)ON=C(Me)2-4-CF₃ | | |
| 24-43 | 5-CF₃ | NH | 5-OCH₂cPr-4-CF₃ | | |
| 24-44 | 5-CF₃-6-OnPr | NH | 5-Oet-4-CF₃ | | |
| 24-45 | 5-CF₃ | NH | 6-C(O)OCH₂CHF₂-4-CF₃ | | |
| 24-46 | 3-Me | NH | 6-OnBu-4-CF₃ | | |
| 24-47 | 3-F | NH | 6-OnPr-4-CN | | |
| 24-48 | 5-CN | NH | 6-C(O)OCH₂Ome-4-CF₃ | | $R^1_a$ = C(S)Ome, cis |
| 24-49 | 5-NO₂ | NH | 6-C(O)OCH₂tBu-4-CF₃ | | |
| 24-50 | 5-CHO | NH | 6-C(O)N(Me)₂-4-CF₃ | | |
| 24-51 | 4-Ome | NH | 6-C(O)OCH(Me)CH(Me)₂-4-CF₃ | | |
| 24-52 | 4-cPr | NH | 3-C(O)OCH(Et)₂-4-CF₃ | | |
| 24-53 | 5-OcHex | Nme | 3-C(O)Ome-4-CF₃ | | $R^3_a$ = NHSO2Me, trans |
| 24-54 | 3-CH₂CH₂cPr | Nme | 3-C(O)OiPr-4-CF₃ | | $R^1_a$ = Ph, cis |
| 24-55 | 4-OCH₂cPr | Nme | 3-C(O)O(CH₂)₂Ome-4-CF₃ | | |
| 24-56 | 6-Me | Nac | 3-C(O)OCH(Me)CH₂Ome-4-CF₃ | | |
| 24-57 | 5-OcHex | Nac | 3-C(O)OCH(CN)Me-4-CF₃ | | |
| 24-58 | 3-CH₂CH₂cPr | NAC | 3-C(O)OCH(Cl)Et-4-CF₃ | | |
| 24-59 | 4-OCH=CH₂ | NCO₂Me | 3-C(O)SiPr-4-CF₃ | | |
| 24-60 | 5-OCF₃ | NCO₂Me | 3-Obn-4-CF₃ | | $R^3_a$ = N(SO2Me)2, trans |
| 24-61 | 4-OCH=CHCH₂CF₃ | NCO₂Me | 3-OH-4-CF₃ | | $R^1_a$ = Et, cis |
| 24-62 | 4-CO₂Et | NCO₂Me | 5-OCH₂CH(Me)Ome-4-CF₃ | | |
| 24-63 | 6-F | NCO₂Me | 5-C(O)OiPr-4-CF₃ | | |
| 24-64 | 6-CN | NCO₂Me | 5-CH(OTMS)CH₂CN-4-CF₃ | | |
| 24-65 | 4-CF₃-5-Cl | NCO₂Me | 5-CH(OH)CH₂CN-4-CF₃ | | |
| 24-66 | 4-OCH=CHCH₂CF₃ | NCO₂Me | 5-OnPr-4-CF₃ | | |
| 24-67 | — | NCO₂Me | 5-OCH₂cPr-4-C₃F₇ | | |
| 24-68 | 6-Me | NCO₂Me | 4-Ph | | |
| 24-69 | 5-OcHex | NCO₂Me | 3,4,5,6-F₄ | | |

Note that R1b, R2b, $R^3_b$, R3b, $R^4_a$, R4b, and R⁵ represent hydrogen atom, respectively, unless otherwise indicated.

Cis and trans represent positional relationship between X and ($R^1_a$, $R^2_a$, $R^3_a$, $R^4_a$, or R⁵).

TABLES 50-53

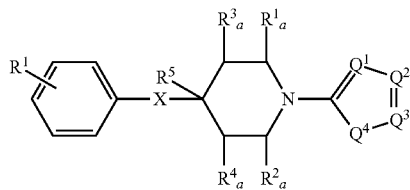

| Compound No. | R¹ | X | Q¹ | Q² | Q³ | Q⁴ | Physical constant [ ]: Melting point ° C. | Remark |
|---|---|---|---|---|---|---|---|---|
| 25-1 | 2-OnPr-4-CF$_3$ | O | N | N | C—CF$_3$ | S | nD22.2-1.4992 | R$^3_a$ = Et, cis |
| 25-2 | 2-OnPr-4-CF$_3$ | O | N | N | C—CF$_3$ | S | nD22.2-1.4998 | R$^3_a$ = Et, trans |
| 25-3 | 4-CF$_3$ | O | N | N | C—CF$_3$ | S | nD22.5-1.5041 | R$^3_a$ = Et, trans |
| 25-4 | 4-CF$_3$ | O | N | N | C—CF$_3$ | S | nD22.5-1.5034 | R$^3_a$ = Et, cis |
| 25-5 | 4-CF$_3$ | O | N | N | C—CF$_3$ | S | [85-86] | |
| 25-6 | 4-Cl | O | N | N | C—CF$_3$ | S | nD22.8-1.5354 | R$^3_a$ = Et, trans |
| 25-7 | 4-CF$_3$ | O | N | C—Cl | N | S | [61-62] | |
| 25-8 | 3-Cl | O | N | N | C—CF$_3$ | S | nD25.9-1.5374 | R$^3_a$ = Et, cis |
| 25-9 | 3-Cl | O | N | N | C—CF$_3$ | S | nD26.3-1.5368 | R$^3_a$ = Et, trans |
| 25-10 | 4-Cl | O | N | N | C—CF$_3$ | S | nD26.3-1.5368 | R$^3_a$ = Et, cis |
| 25-11 | 2-Cl | O | N | N | C—CF$_3$ | S | nD25.1-1.5414 | R$^3_a$ = Et, cis |
| 25-12 | 2-Cl | O | N | N | C—CF$_3$ | S | nD25.5-1.5266 | R$^3_a$ = Et, trans |
| 25-13 | 5-CN | O | N | CH | C—Br | CH$_2$ | | |
| 25-14 | 5-NO$_2$ | O | N | CMe | CH | CH$_2$ | | |
| 25-15 | 5-CHO | O | N | N | C—CO$_2$Me | CH$_2$ | | |
| 25-16 | 4-Ome | O | N | N | C—CH$_2$OH | CH$_2$ | | |
| 25-17 | 4-cPr | O | N | CH | C—CHO | CH$_2$ | | |
| 25-18 | 5-OcHex | O | N | CH | C—CF$_2$H | CH$_2$ | | R$^1_a$ = CHO, trans |
| 25-19 | 3-CH$_2$CH$_2$cPr | O | N | N | C—CF$_3$ | Cme$_2$ | | R$^1_a$ = CN, trans |
| 25-20 | 4-OCH$_2$cPr | O | N | N | C—CF$_3$ | Cme$_2$ | | |
| 25-21 | 4-OCH=CH$_2$ | S | N | N | C—CF$_3$ | Cme$_2$ | | |
| 25-22 | 5-OCF$_3$ | S | N | N | C—CF$_3$ | CH$_2$ | | R$^3_a$ = CO$_2$Me, trans |
| 25-23 | 4-OCH=CHCH$_2$CF$_3$ | S | CH | N | CH | CH$_2$ | | R$^3_a$ = Br, trans |
| 25-24 | 4-CO$_2$Et | S | N | CH | C—Br | CH$_2$ | | |
| 25-25 | 6-F | S | N | Cme | CH | CH$_2$ | | |
| 25-26 | 6-CN | S | N | Cme | C—CO$_2$Me | CH$_2$ | | |
| 25-27 | 6-NO$_2$ | S | CH | CH | N | NH | | |
| 25-28 | 6-OcPr | S | N | CH | C—Br | CH$_2$ | | |
| 25-29 | 5-CN | S | N | Cme | CH | CH$_2$ | | |
| 25-30 | 5-CF$_3$ | S | N | N | C—CO$_2$Me | CH$_2$ | | |
| 25-31 | 3-Me | S | N | N | C—CH$_2$OH | CH$_2$ | | |
| 25-32 | 3-F | S | N | CH | C—CHO | CH$_2$ | | |
| 25-33 | 5-CN | SO | N | CH | C—CF$_2$H | CH$_2$ | | |
| 25-34 | 5-NO$_2$ | SO | N | N | C—CF$_3$ | Cme$_2$ | | |
| 25-35 | 5-CHO | SO | N | N | C—CF$_3$ | Cme$_2$ | | |
| 25-36 | 4-Ome | SO | N | N | C—CF$_3$ | Cme$_2$ | | |
| 25-37 | 5-CF$_3$ | SO | N | N | C—CF$_3$ | CH$_2$ | | |
| 25-38 | 4-CF$_3$-6-Cl | SO$_2$ | CH | N | CH | CH$_2$ | | |
| 25-39 | 5-CF$_3$ | SO$_2$ | N | CH | C—Br | CH$_2$ | | |
| 25-40 | 5-CF$_3$-6-OnPr | SO$_2$ | N | Cme | CH | CH$_2$ | | R$^1_a$ = CF$_3$, cis |
| 25-41 | 5-CF$_3$ | SO$_2$ | N | Cme | C—CO$_2$Me | CH$_2$ | | R$^1_a$ = Ome, cis |
| 25-42 | 3-Me | SO$_2$ | CH | CH | N | NH | | R$^3_a$ = Nme$_2$, trans |
| 25-43 | 3-F | SO$_2$ | N | CH | C—Br | CH$_2$ | | |
| 25-44 | 5-CN | SO$_2$ | N | Cme | CH | CH$_2$ | | |
| 25-45 | 5-NO$_2$ | SO$_2$ | N | N | C—CO$_2$Me | CH$_2$ | | |
| 25-46 | 5-CHO | SO$_2$ | N | N | C—CH$_2$OH | CH$_2$ | | |
| 25-47 | 4-Ome | SO$_2$ | N | CH | C—CHO | CH$_2$ | | |
| 25-48 | 4-cPr | SO$_2$ | N | CH | C—CF$_2$H | CH$_2$ | | |
| 25-49 | 5-OcHex | NH | N | N | C—CF$_3$ | Cme$_2$ | | |
| 25-50 | 3-CH$_2$CH$_2$cPr | NH | N | N | C—CF$_3$ | Cme$_2$ | | R$^3_a$ = NO$_2$, trans |
| 25-51 | 4-OCH$_2$cPr | NH | N | N | C—CF$_3$ | Cme$_2$ | | R$^3_a$ = Me, cis |
| 25-52 | 6-Me | NH | N | N | C—CF$_3$ | CH$_2$ | | |
| 25-53 | 5-OcHex | NH | CH | N | CH | CH$_2$ | | |
| 25-54 | 3-CH$_2$CH$_2$cPr | NH | N | CH | C—Br | CH$_2$ | | |
| 25-55 | 4-OCHCH$_2$ | NH | N | Cme | CH | CH$_2$ | | |
| 25-56 | 5-OCF$_3$ | NH | N | Cme | C—CO$_2$Me | CH$_2$ | | |
| 25-57 | 4-OCH=CHCH$_2$CF$_3$ | NH | CH | CH | N | NH | | |
| 25-58 | 4-CO$_2$Et | NH | N | CH | C—Br | CH$_2$ | | |
| 25-59 | 6-F | NH | N | Cme | CH | CH$_2$ | | |
| 25-60 | 6-CN | Nme | N | N | C—CO$_2$Me | CH$_2$ | | R$^3_a$ = F, cis |
| 25-61 | 4-CF$_3$-5-Cl | Nme | N | N | C—CH$_2$OH | CH$_2$ | | R$^3_a$ = Et, trans |
| 25-62 | 4-OCH=CHCH$_2$CF$_3$ | Nme | N | CH | C—CHO | CH$_2$ | | |
| 25-63 | — | Nme | N | CH | C—CF$_2$H | CH$_2$ | | |
| 25-64 | 6-Me | Nme | N | N | C—CF$_3$ | Cme$_2$ | | |
| 25-65 | 5-OcHex | Nme | N | N | C—CF$_3$ | Cme$_2$ | | |

TABLES 50-53-continued

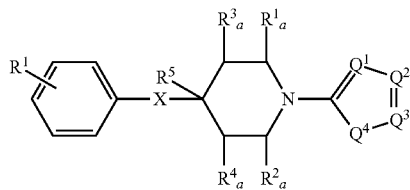

| Compound No. | R¹ | X | Q¹ | Q² | Q³ | Q⁴ | Physical constant [ ]: Melting point ° C. | Remark |
|---|---|---|---|---|---|---|---|---|
| 25-66 | 5-CN | Nme | N | N | C—CF$_3$ | Cme$_2$ | | |
| 25-67 | 5-NO$_2$ | Nac | N | N | C—CF$_3$ | CH$_2$ | | R$^1{}_a$ = SO$_2$Me, trans |
| 25-68 | 5-CHO | Nac | CH | N | CH | CH$_2$ | | R$^1{}_a$ = Et, cis |
| 25-69 | 4-Ome | Nac | N | CH | C—Br | CH$_2$ | | |
| 25-70 | 4-cPr | Nac | N | Cme | CH | CH$_2$ | | |

Note that R1b, R2b, R$^3{}_a$, R3b, R$^4{}_a$, R4b, and R$^5$ represent hydrogen atom, respectively, unless otherwise indicated.
Cis and trans represent positional relationship between X and (R$^1{}_a$, R$^2{}_a$, R$^3{}_a$, R$^4{}_a$, or R$^5$).

TABLES 54-57

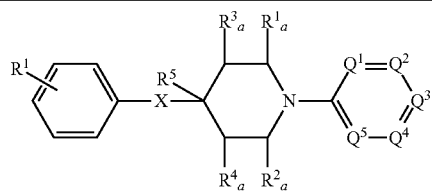

| Compound No. | R¹ | X | Q¹ | Q² | Q³ | Q⁴ | Q⁵ | Physical Constant [ ]: Melting point ° C. | Remark |
|---|---|---|---|---|---|---|---|---|---|
| 26-1 | 2-OEt-4-CF$_3$ | O | N | C—OiPr | N | C—CF$_3$ | CH | vis | |
| 26-2 | 2-OnPr-4-CF$_3$ | O | N | N | C—CF$_3$ | CH | CH | [106-109] | |
| 26-3 | 2-OnPr-4-CF$_3$ | O | N | N | C—CF$_3$ | CH | CH | vis | R$^3{}_a$ = Me, cis |
| 26-4 | 2-OnPr-4-CF$_3$ | O | N | N | C—CF$_3$ | CH | CH | vis | R$^3{}_a$ = Me, trans |
| 26-5 | 2-OnPr-4-CF$_3$ | O | N | N | C—CF$_3$ | CH | CH | nD22.3-1.4992 | R$^3{}_a$ = Et, cis |
| 26-6 | 2-OnPr-4-CF$_3$ | O | N | N | C—CF$_3$ | CH | CH | amorphous | R$^3{}_a$ = Et, trans |
| 26-7 | — | O | N | N | C—Cl | CH | CH | vis | R$^3{}_a$ = Et, cis |
| 26-8 | 4-CF$_3$ | O | N | N | C—Cl | CH | CH | nD26.3-1.5522 | R$^3{}_a$ = Et, trans |
| 26-9 | 4-CF$_3$ | O | N | N | C—CN | CH | CH | amorphous | R$^3{}_a$ = Et, cis |
| 26-10 | 4-CF$_3$ | O | N | N | C—CN | CH | CH | vis | R$^3{}_a$ = Et, trans |
| 26-11 | 4-CF$_3$ | O | N | N | C—CF$_3$ | CH | CH | [108-109] | |
| 26-12 | 4-CF$_3$ | O | N | CH | N | C—CF$_3$ | CH | nD26.1-1.5093 | R$^3{}_a$ = Et, cis |
| 26-13 | 4-CF$_3$ | O | N | CH | N | C—CF$_3$ | CH | nD26.2-1.5088 | R$^3{}_a$ = Et, trans |
| 26-14 | 4-CF$_3$ | O | N | C—CF$_3$ | N | CH | CH | nD22.4-1.5071 | R$^3$ = Et, trans |
| 26-15 | 4-CF$_3$ | O | N | N | C—Cl | CH | CH | [120-121] | |
| 26-16 | 4-CF$_3$ | O | N | N | C—CF$_3$ | CH | CH | nD25.5-1.5148 | R$^3{}_a$ = Et, cis |
| 26-17 | 4-CF$_3$ | O | N | N | C—CF$_3$ | CH | CH | [89-90] | R$^3{}_a$ = Et, trans |
| 26-18 | 4-CF$_3$ | O | H | N | C—Cl | CH | CH | nD25.2-1.5471 | R$^3{}_a$ = Et, cis |
| 26-19 | 4-CF$_3$ | O | N | N | C—CF$_3$ | CH | CH | [89-90] | R$^3{}_a$ = Et, trans |
| 26-20 | 2-OnPr-4-CF$_3$ | O | CH | CH | CH | CH | CH | | |
| 26-21 | 4-CF$_3$ | O | N | N | C—CF$_3$ | CH | CH | | R$^3{}_a$ = F, trans |
| 26-22 | 2-OnPr-4-CF$_3$ | O | N | N | C—CF$_3$ | CH | CH | | R$^1{}_a$ = Nme$_2$, cis |
| 26-23 | 4-CF$_3$ | O | N | CH | CH | N | C—Me | | |
| 26-24 | 2-CH$_2$OEt-4-CF$_3$ | O | N | CH | CH | N | CH | | |
| 26-25 | 4-CF$_3$ | S | N | CH | C—CF$_3$ | N | CH | | |
| 26-26 | 2,6-Me$_2$ | S | N | C—Br | CH | N | CH | | |
| 26-27 | 4-OMe | S | N | CH | CH | CH | N | | |
| 26-28 | 3-NO$_2$ | S | N | CH | C—CN | CH | CH | | |
| 26-29 | 2-F | S | N | C—CN | CH | CH | CH | | R$^3{}_a$ = CN, cis |
| 26-30 | 3-CHO | S | N | CH | N | CH | CH | | R$^3{}_a$ = NO$_2$, trans |
| 26-31 | 3-OiPr | S | CH | N | C—CN | CH | CH | | |
| 26-32 | 4-Me | S | N | CH | CH | CH | N | | |
| 26-33 | 4-cPr | S | C—Me | N | CH | CH | CH | | |
| 26-34 | 3-OcPr | SO | N | C—F | CH | CH | N | | R$^1{}_a$ = CHO, cis |
| 26-35 | 4-CH$_2$cPr | SO | N | C—Cl | CH | CH | N | | R$^1{}_a$ = OCF$_3$, trans |
| 26-36 | 2-OCH$_2$CH$_2$cPr | SO | N | CH | N | CH | CH | | |

TABLES 54-57-continued

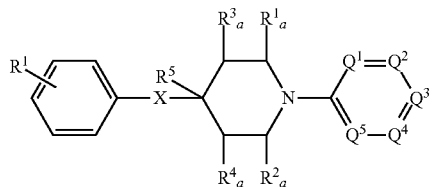

| Compound No. | R¹ | X | Q¹ | Q² | Q³ | Q⁴ | Q⁵ | Physical Constant [ ]: Melting point ° C. | Remark |
|---|---|---|---|---|---|---|---|---|---|
| 26-38 | 3-OCH=CMe₂ | SO | CH | C—Me | N | C—Me | CH | | |
| 26-39 | 4-OCF₃ | SO | N | N | C—CF₃ | CH | CH | | |
| 26-40 | 4-OCF₃ | SO₂ | N | N | CH | CH | CH | | $R^1_a$ = OMe, cis |
| 26-41 | 3-CO₂Me | SO₂ | CH | CH | CH | CH | CH | | $R^1_a$ = CO₂Et, trans |
| 26-42 | 3-Me | SO₂ | N | N | C—CF₃ | CH | CH | | |
| 26-43 | 4-tBu | SO₂ | N | N | C—CF₃ | CH | CH | | |
| 26-44 | 2-CH=CHMe | SO₂ | N | CH | CH | N | C—Me | | |
| 26-45 | 2-OCH₂cPr-4-CF₃ | SO₂ | N | CH | CH | N | CH | | |
| 26-46 | 2-OCH₂cPr-4-CF₃ | SO₂ | N | CH | C—CF₃ | N | CH | | |
| 26-47 | 2-CO₂iPr-4-CF₃ | SO₂ | N | C—Br | CH | N | CH | | |
| 26-48 | 2-OnBu-4-CF₃ | SO₂ | N | CH | CH | CH | N | | |
| 26-49 | 2-OiBu-4-CF₃ | NH | N | CH | C—CN | CH | CH | | |
| 26-50 | 2-OEt-4-CF₃ | NH | N | C—CN | CH | CH | CH | | |
| 26-51 | 2-CO₂iPr-4-CF₃ | NH | N | CH | N | CH | CH | | |
| 26-52 | 2-OnPr-4-CF₃ | NH | CH | N | C—CN | CH | CH | | |
| 26-53 | 4-CF₃ | NH | N | CH | CH | CH | N | | $R^3_a$ = Et, trans |
| 26-54 | 2-OnPr-4-CF₃ | NH | C—Me | N | CH | CH | CH | | $R^1_a$ = C(S)OMe, cis |
| 26-55 | 4-CF₃ | NH | N | C—F | CH | CH | N | | |
| 26-56 | 2-CH₂OEt-4-CF₃ | NH | N | C—Cl | CH | CH | N | | |
| 26-57 | 4-CF₃ | NH | N | CH | CH | CH | CH | | |
| 26-58 | 2,6-Me₂ | NH | CH | C—Me | N | C—Me | CH | | |
| 26-59 | 3-OCH=CMe₂ | NMe | CH | CH | CH | CH | CH | | $R^1_a$ = tBu, trans |
| 26-60 | 4-OCF₃ | NMe | N | N | C—CF₃ | CH | CH | | $R^3_a$ = CH₂cPr, cis |
| 26-61 | 4-OCF₃ | NMe | N | N | C—CF₃ | CH | CH | | |
| 26-62 | 3-CO₂Me | NMe | N | CH | CH | N | C—Me | | |
| 26-63 | 4-tBu | Nme | N | CH | C—CF₃ | N | CH | | |
| 26-64 | 2-CH=CHMe | NAc | N | C—Br | CH | N | CH | | |
| 26-65 | 2-OCH₂cPr-4-CF₃ | NAc | N | CH | CH | CH | N | | $R^1_a$ = Et, trans |
| 26-66 | 3-OCH=CMe₂ | NAc | N | CH | C—CN | CH | CH | | $R^3_a$ = OMe, cis |
| 26-67 | 4-OCF₃ | NAc | N | C—CN | CH | CH | CH | | |
| 26-68 | 2-OCH₂CH₂OMe-4-CF₃O | | N | CH | C—CN | CH | CH | [57-60] | |

Note that R1b, R2b, $R^3_a$, R3b, $R^4_a$, R4b, and R⁵ represent hydrogen atom, respectively, unless otherwise indicated.
Cis and trans represent positional relationship between X and ($R^1_a$, $R^2_a$, $R^3_a$, $R^4_a$, or R⁵).

FORMULATION EXAMPLES

[Insecticides/Acaricides]

Although a few examples regarding compositions of the present invention are shown next, additives and proportions added are changeable over a wide range without being limited to these examples. Parts in Formulation Examples show parts by weight.

Formulation Example 1

Wettable Powder

| | |
|---|---|
| Compound of the present invention | 40 parts |
| Diatomaceous earth | 53 parts |
| Higher alcohol sulfate ester | 4 parts |
| Alkylnaphthalenesulfonate salt | 3 parts |

The above components were mixed homogenously and ground finely to obtain a wettable powder with 40% of active ingredient.

Formulation Example 2

Emulsion

| | |
|---|---|
| Compound of the present invention | 30 parts |
| Xylene | 33 parts |
| Dimethylformamide | 30 parts |
| Polyoxyethylene alkyl allyl ether | 7 parts |

The above components were mixed and dissolved to obtain an emulsion with 30% of active ingredient.

Formulation Example 3

Dusting Powder

| | |
|---|---|
| Compound of the present invention | 10 parts |
| Talc | 89 parts |
| Polyoxyethylene alkyl allyl ether | 1 part |

The above components were mixed homogenously and ground finely to obtain a dusting powder with 10% of active ingredient.

Formulation Example 4

Granules

| | |
|---|---|
| Compound of the present invention | 5 parts |
| Clay | 73 parts |
| Bentonite | 20 parts |
| Sodium dioctylsulfosuccinate salt | 1 part |
| Sodium phosphate | 1 part |

The above components were mixed and ground well and, after adding water thereto and kneading together, granulated and dried to obtain granules with 5% of active ingredient.

Formulation Example 5

Suspending Agent

| | |
|---|---|
| Compound of the present invention | 10 parts |
| Sodium lignin sulfonate | 4 parts |
| Sodium dodecylbenzenesulfonate | 1 part |
| Xanthan gum | 0.2 parts |
| Water | 84.8 parts |

The above components were mixed and subjected to wet-grinding until the grain size of 1 μm or less was achieved to obtain a suspending agent with 10% of active ingredient.

Next, usefulness of the compounds of the present invention as active ingredients of acaricides and insecticides are shown by Test Examples.

Test Example 1

Effectiveness Against *Tetranychus urticae*

17 adult female *Tetranychus urticae*, which were resistant to organophosphorus pesticides, were inoculated on the first true leaf of a common bean, which was seeded in a pot with a diameter of 9 cm, where 7 to 10 days had passed after the germination. After the inoculation, the drug solution, which was prepared by following the method of the wettable powder shown in Example 1 of the drugs and by diluting with water to achieve the compound concentration of 125 ppm, was applied. The pot was placed in a temperature-controlled room where the temperature and humidity were set to 25° C. and 65% respectively, and the adulticidal rate was examined 3 days after the application. The test was repeated twice.

As a result, the compounds below showed the insecticidal rate of 100%. 1-1, 1-4 to 1-7, 1-10, 1-13, 1-17, 1-18, 1-21 to 1-29, 1-31 to 1-36, 1-39 to 1-47, 1-50, 1-51, 1-54, 2-3, 3-1, 4-5, 4-7, 4-9, 4-13, 4-16, 4-18 to 4-20, 4-53 to 4-55, 4-58 to 4-61, 4-64, 4-70, 4-71, 5-1 to 5-8, 10-1, 11-1, 13-2, 15-1, 15-7 16-1 to 16-26, 16-61, 16-65, 16-69, 16-73 to 16-75, 16-78, 16-82 to 16-91, 17-2, 17-3, 17-7 to 17-10, 19-1 to 19-3, 21-1, 21-3, 21-5, 21-6, 21-14 to 21-16, 22-1, 22-4, 22-5, 23-2, 25-1, 25-2, 26-3 to 26-6

Test Example 2

Effectiveness Against *Panonychus citri*

10 adult female *Panonychus citri* were inoculated on the leaf of a mandarin orange, which was placed in a petri dish. After the inoculation, the drug solution, which was prepared by following the method of the emulsion shown in Example 2 of the drugs and by diluting with water to achieve the compound concentration of 125 ppm, was applied using a rotary spreading tower. The dish was placed in a temperature-controlled room where the temperature and humidity were set to 25° C. and 65% respectively, adults were removed 3 days after the application, and whether eggs laid during these 3 days could grow to become adults was examined on the 11th day.

As a result, the compounds below showed the insecticidal rate of 100%. 1-1, 1-5, 1-7, 1-13, 1-17, 1-24, 1-31, 1-32, 1-47, 1-50, 3-1, 4-5, 4-53, 4-54, 4-58 to 4-61, 4-64, 4-70, 4-71, 5-1, 5-2, 5-4, 5-8, 10-1, 12-4, 16-1 to 16-13, 16-15 to 16-20, 16-22, 16-23, 16-26, 16-61, 16-73, 16-83, 16-84, 16-89 to 16-91, 17-7, 17-9, 17-10, 19-1 to 19-3, 21-5, 21-6, 21-13, 22-1, 22-4, 23-2, 26-3, 26-5, 26-6

Test Example 3

Effectiveness Test Against *Pseudaletia separata*

0.2 ml of a commercially available artificial diet (Insecta LFS manufactured by Nihon Nosan-Kogyo Co., Ltd) was put into a plastic test tube with a volume of 1.4 ml and was used as a test diet. The compound was adjusted to prepare 1% solution using dimethylsulfoxide containing 0.5% tween 20 and this solution was applied by adding dropwise onto the surface of the diet in an amount equivalent to 10 μg of the compound. 2 second-instar larvae of *Pseudaletia* separate were inoculated to each test tube and the tubes were sealed with plastic lids. The tubes were left at 25° C. and the insecticidal rate and amount of food ingested were examined after 5 days. The test was repeated twice.

In the present test, the compounds below were effective by showing the insecticidal rate of 100%, or the amount of food ingested was 10% or less compared to the solvent control group.
4-3, 4-4, 16-1, 16-2, 17-3, 17-7 to 17-9, 25-4

Test Example 4

Effectiveness Test Against *Culex pipiens molestus*

10 larvae of *Culex pipiens molestus*, which were hatched 1 day before, and 0.225 ml of distilled water containing 0.5 mg of feed for aquarium fish (TetraMin® manufactured by Tetra Japan Co. Ltd) were put into a polystyrene test vessel with a volume of 0.3 ml. The compound was adjusted to prepare 1% solution using dimethylsulfoxide containing 0.5% tween 20 and further diluted to 0.01% with distilled water. This diluted drug solution was added to the test vessel with *Culex pipiens molestus* and was stirred (final compound concentration 0.001%). The vessels were left at 25° C. and the insecticidal rate was examined after 2 days. The test was repeated twice.

In the present test, the compound below was effective by showing the insecticidal rate of 90% or more.
4-3

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

[Industrial Applicability]

According to the present invention, it is possible to provide agents for pest control with excellent bioactivities especially in terms of insecticidal/acaricidal activities and high safety and furthermore, it is possible to provide cyclic amine compounds with a novel structure, salts thereof, or N-oxides thereof.

What is claimed is:

1. Agents for pest control comprising cyclic amine compounds represented by formula (1)

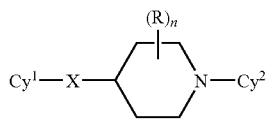

or salts thereof, or N-oxides thereof, as an active ingredient,
wherein $Cy^1$ represents a group represented by formula (a) below,

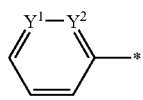

wherein $Y^1$ and $Y^2$ represent a carbon atom and the symbol * represents the bonding positions, the group may be substituted by a halogen atom, a haloalkyl group, a haloalkoxy group, an alkoxy group, or an alkoxycarbonyl group;

X represents oxygen;

R, which does not form a ring, represents a hydroxyl group, a halogen atom, an amino group, a nitro group, or an alkyl group;

n is an integer from 0 to 9 and each R may be the same or different when n is 2 or more; and $Cy^2$ represents a heterocycle which may be substituted by a halogen atom, a haloalkyl group, an alkoxy group, or a cyano group, the heterocycle being furanyl, thiophenyl, pyrrolyl, oxazolyl, thiazolyl, isoxazolyl, isothiazolyl, imidazolyl, pyrazolyl, oxadiazolyl, thiadiazolyl, triazolyl, pyridinyl, pyridazinyl, pyrazinyl, pyrimidinyl, triazinyl, piperidino, piperidyl, tetrahydrofuranyl, tetrahydropyranyl, pyrrolidinyl, piperidinyl, or piperazinyl, with the proviso that when $Cy^2$ is pyridin-2-yl, $Cy^2$ is substituted with at least one cyano group, when $Cy^2$ represents pyridazinyl, $Cy^2$ is substituted with a haloalkyl group, when $Cy^2$ represents piperazinyl, $Cy^2$ is substituted with a halogen atom, a haloalkyl group, an alkoxy group, or a cyano group, when $Cy^2$ represents thiazolyl, $Cy^2$ is substituted with a haloalkyl group, or an alkoxy group, and when $Cy^2$ represents thiadiazolyl, $Cy^2$ is substituted with a halogen atom, a haloalkyl group, or an alkoxy group.

2. Agents for pest control according to claim 1, wherein the agents for pest control are insecticides or acaricides.

3. Cyclic amine compounds represented by formula (2)

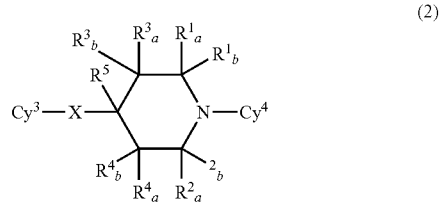

or salts thereof or N-oxides thereof,
wherein $Cy^3$ represents any one of formulae (b) to (d) below,

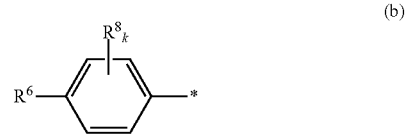

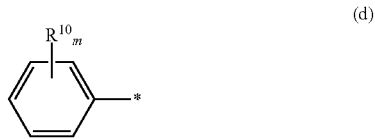

wherein $R^6$ represents haloalkyl or haloalkoxy, $R^7$ represents unsubstituted or substituted alkoxy, or unsubstituted or substituted alkoxycarbonyl;

$R^8$ to $R^{10}$ each independently represents halogen, haloalkyl, haloalkoxy, alkoxy (optionally substituted with $G^1$), or alkoxycarbonyl;

$G^1$ represents hydroxyl, halogen, amino, nitro, or an organic group;

k, and l each independently represents any one of an integer from 0 to 4 and each $R^8$, and each $R^9$ may be the same or different when k, and l, are 2 or more; m is any one of an integer from 0 to 5 and each $R^{10}$ may be the same or different when m is 2 or more;

X represents oxygen;

$R^1_a$, $R^1_b$, $R^2_a$, $R^2_b$, $R^3_a$, $R^3_b$, $R^4_a$, $R^4_b$, and $R^5$ which do not form saturated rings together each independently represents a hydrogen, hydroxyl, halogen, unsubstituted or substituted amino, nitro, or an organic group;

$Cy^4$ represents
pyridin-2-yl substituted with one or more cyano, pyridin-3-yl, pyridazin-3-yl, pyrazinyl, thiazol-2-yl, pyrimidin- 2-yl, or 1,3,4-thiadiazol-2-yl, which are optionally substituted with $G^2$ when $Cy^3$ is a functional group represented by formula (c), pyridin-2-yl substituted with one or more cyano, pyridin-3-yl, pyridazin-3-yl, pyrazinyl, thiazol-2-yl, pyrimidin-2-yl, or 1,3,4-thiadiazol-2-yl, which are optionally substituted with $G^2$ when $Cy^3$ is a functional group represented by formula (b) and pyridin-2-yl substituted with one or more cyano, pyrazinyl, or 1,3,4-thiadiazol-2-yl which are optionally substituted with $G^2$ when $Cy^3$ is a functional group represented by formula (d);

$G^2$ represents halogen, alkoxy (optionally substituted with $G^3$), or haloalkyl;

and $G^3$ represents hydroxyl, cyano, alkoxy, alkoxyalkoxy, or trialkylsilyloxy, and when $Cy^4$ represents thiazol-2-yl, $Cy^4$ is substituted with a haloalkyl group or an alkoxy group, and when $Cy^4$ represents 1,3,4-thiadiazol-2-yl, $Cy^4$ is substituted with a halogen atom, a haloalkyl group, or an alkoxy group.

4. Agents for pest control according to claim 1, wherein the heterocycle is selected from the group consisting of pyrrolyl, pyrazolyl, 1,3,4-thiadiazolyl, pyridinyl, pyridazinyl, pyrazinyl, and pyrimidinyl.

* * * * *